US008716507B2

(12) United States Patent
Mikhailine et al.

(10) Patent No.: US 8,716,507 B2
(45) Date of Patent: May 6, 2014

(54) IRON(II) CATALYSTS CONTAINING DIIMINO-DIPHOSPHINE TETRADENTATE LIGANDS AND THEIR SYNTHESIS

(75) Inventors: Alexandre Mikhailine, Keswick (CA); Friederike Freutel, Mainz (DE); Christine Sui-Seng, Saint Germain en Laye (FR); Nils Meyer, Werne (DE); Robert H. Morris, Toronto (CA); Paraskevi Olympia Lagaditis, Richmond (CA)

(73) Assignee: The Governing Council of University of Toronto, Toronto (CA)

( * ) Notice: Subject to any disclaimer, the term of this patent is extended or adjusted under 35 U.S.C. 154(b) by 490 days.

(21) Appl. No.: 12/609,955

(22) Filed: Oct. 30, 2009

(65) Prior Publication Data

US 2010/0145087 A1 Jun. 10, 2010

Related U.S. Application Data

(60) Provisional application No. 61/193,147, filed on Oct. 31, 2008.

(51) Int. Cl.
C07F 15/02 (2006.01)
B01J 31/00 (2006.01)
B01J 31/18 (2006.01)
C07C 29/145 (2006.01)

(52) U.S. Cl.
CPC ............ *C07F 15/025* (2013.01); *B01J 31/1805* (2013.01); *C07C 29/145* (2013.01)
USPC .................... 556/16; 556/32; 556/36; 556/21; 502/155

(58) Field of Classification Search
USPC ................................. 556/21, 32, 36; 502/155
See application file for complete search history.

(56) References Cited

U.S. PATENT DOCUMENTS

| 6,590,115 B2 | 7/2003 | Boaz et al. |
| 2006/0135804 A1 | 6/2006 | Boaz et al. |
| 2010/0311975 A1 | 12/2010 | Abdur-Rashid et al. |

FOREIGN PATENT DOCUMENTS

WO 2009/055912 A1 7/2009

OTHER PUBLICATIONS

Suzanne C. Bart et al., "Preparation and Molecular and Electronic Structures of Iron(0) Dinitrogen and Silane Complexes and Their Application to Catalytic Hydrogenation and Hydrosilation", *J. Am. Chem. Soc.* 126:13794-13807 (2004), JACS Articles Published on Web Oct. 5, 2004, American Chemical Society.
Claudio Bianchini et al., "Chemoselective Hydrogen-Transfer Reduction of α,β-Unsaturated Ketones Catalyzed by Isostructural Iron(II), Ruthenium(II) and Osmium(II) cis Hydride η²-Dihydrogen Complexes" *Organometallics* 12:3753-3761 (1993), American Chemical Society.
Charles P. Casey et al., "An Efficient and Chemoselective Iron Catalyst for the Hydrogenation of Ketones" *J. Am. Chem. Soc.* 129:5816-5817 (2007) JACS Communications Published on Web Apr. 17, 2007, American Chemical Society.
Jian-Shan Chen et al., "Asymmetric Transfer Hydrogenation of Ketones Catalyzed by Chiral Carbonyl Iron Systems" *Acta Chimica Sinica* 62(18):1745-1750 (2004).
Stephan Enthaler et al., "Biomimetic Transfer Hydrogenation of Ketones with Iron Porphyrin Catalysts", *Tetrahedron Letters* 47:8095-8099 (2006), Elsevier Ltd.
Jing-Xing Gao et al, "New Chiral Catalysts for Reduction of Ketones", *Chirality* 12:383-388 (2000), Wiley-Liss, Inc.
Jing-Xing Gao et al, "A Ruthenium(II) Complex with a $C_2$-Symmetric Diphosphine/Diamine Tetradentate Ligand for Asymmetric Transfer Hydrogenation of Aromatic Ketones", *Organometallics* 15:1087-1089 (1996), American Chemical Society.
Jing-Xing Gao et al, "Synthesis and Characterization of Iron(2+) and Ruthenium(2+) Diimino-, Diamino- and Diamido-Diphosphine Complexes. X-Ray Crystal Structure of *TRANS*-$RuCl_2(P_2N_2C_2H_4)$ · $CHCl_3$", *Polyhedron* 15(8):1241-1251 (1996), Elsevier Science Ltd.
Shohei Hashiguchi et al., "Asymmetric Transfer Hydrogenation of Aromatic Ketones Catalyzed by Chiral Ruthenium(II) Complexes" *J. Am. Chem. Soc.* 117:7562-7563 (1995), American Chemical Society.

(Continued)

*Primary Examiner* — Porfirio Nazario Gonzalez
(74) *Attorney, Agent, or Firm* — Buchanan Ingersoll & Rooney P.C.

(57) ABSTRACT

New hexa-coordinate iron (II) complexes comprising compounds of formula (I) are described. These compounds comprise a tetradentate ligand with donor atoms comprising nitrogen and phosphorus. These complexes are shown for the first time to be useful catalysts for the hydrogenation of ketones, aldehydes, or imines to produce alcohols or amines, and the asymmetric hydrogenation of prochiral ketones or imines to produce non-racemic alcohols or amines. The source of the hydrogen can be hydrogen gas or a hydrogen-donating molecule such as isopropanol or hydrogen-donating mixture such as formic acid and an amine depending on the structure of the catalyst. In certain embodiments, the axial ligands on the catalyst comprise organonitrile ligands, carbonyl ligands, isonitrile ligands, or combinations thereof. The catalysts and the preparation thereof are disclosed. A reaction using phosphine and diamine precursors that is templated by the iron ion is the preferred route to the catalysts.

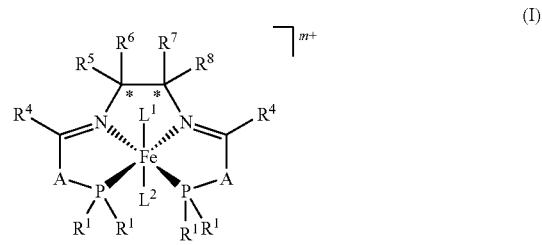

(I)

16 Claims, No Drawings

(56) References Cited

OTHER PUBLICATIONS

Cory A. Jaska et al., "Heterogeneous or Homogeneous Catalysis? Mechanistic Studies of the Rhodium-Catalyzed Dehydrocoupling of Amine-Borane and Phosphine-Borane Adducts", *J. Am. Chem. Soc.* 126:9776-9785 (2004), American Chemical Society, JACS Article Published on Web Jul. 17, 2004.

John C. Jeffery et al., "Metal Complexes of Diiminodiphosphines. Structural and Reactivity Patterns", *Inorg. Chem.* 19:3306-3316 (1980), American Chemical Society.

K. Jothimony et al., "Mechanism for Transfer Hydrogenation of Ketones to Alcohols Catalysed by Hydridotri-Ironundeca-Carbonylate Anion Under Phase Transfer Conditions" *Journal of Molecular Catalysis* 52:301-304 (1989), Elsevier Sequoia.

Alexandre A. Mikhailine et al., "Template Synthesis of Iron(II) Complexes Containing Chiral P-N-N-P and P-N-N Ligands" *Inorganic Chemistry* 47(15):6587-6589 (2008), American Chemical Society.

Valentin Rautenstrauch et al., "Hydrogenation versus Transfer Hydrogenation of Ketones: Two Established Ruthenium Systems Catalyze Both" *Chem. Eur. J.* 9:4954-4967 (2003) Wiley-VCH Verlag GmbH & Co.

Christine Sui-Seng et al., "Highly Efficient Catalyst Systems Using Iron Complexes with a Tetradentate PNNP Ligand for the Asymmetric Hydrogenation of Polar Bonds" *Angew. Chem.* 120:954-957 (2008) Wiley-VCH Verlag GmbH & Co.

Sui-Seng, C. et al., May 29, 2007, 90th Canadian Chemistry Conference and Exhibition, Winnipeg, MB, Canada: poster presentation—"Novel Iron (II) Complexes with Tetradentate P-N-N-P Donor Ligands and Their Application in the Hydrogenation of Ketones".

Sui-Seng, C. et al., Nov. 2, 2007, Inorganic Discussion Weekend, Toronto, ON, Canada : poster presentation—"Highly Efficient Iron Catalysts with Tetradentate P-N-N-P Donor Ligand for the Asymmetric Hydrogenation of Polar Bonds".

Mikhailine, A. et al., Nov. 2, 2007, Inorganic Discussion Weekend, Toronto, ON, Canada : poster presentation—"Iron (II) Complexes with New Tetradentate PNNP and Tridentate PNN Ligands".

Morris, R.H. et al., Jul. 13-15, 2008, International Conference on Organometallic Chemistry, Rennes, France : poster presentation—"Asymmetric Hydrogenation of Ketones using Fe(II) Complexes".

Lagaditis et al. "Template Synthesis of Iron (II) Complexes Containing Tridentate P-N-S, P-N-P, P-N-N, and Tetradentate P-N-N-P Ligands" Inorganic Chemistry (2010) 49:1094-1102, American Chemical Society.

Lagaditis et al., "Iron Complexes for the Catalytic Transfer Hydrogenation of Acetophenone: Steric and Electronic Effects imposed by Alkyl Substituents at Phosphorus" Inorganic. Chemistry (2010) 49:10057-10066, American Chemical Society.

Meyer et al. "Iron (II) Complexes for the Efficient Catalytic Asymmetric Transfer Hydrogenation of Ketones" Chem. Eur. J. (2009) 15:5605-5610, Wiley-VCH Verlag CmbH & Co. KGaA, Weinheim.

Mikhailine et al., "Efficient Asymmetric Transfer Hydrogenation of Ketones Catalyzed by an Iron Complex containing a P-N-N-P Tetradentate Ligand Formed by Template Synthesis" J. Am. Chem. Soc. (2009) 131:1394-1395, American Chemical Society.

Sui-Seng et al., "Synthesis and Characterization of Iron(II) Complexes with Tetradentate Diiminodiphosphine or Diaminodiphosphine Ligands as Precatalysts for the Hydrogenation of Acetophenone" Inorg. Chem. (2009) 48:735-743, American Chemical Society.

Sui-Seng et al, "Highly Efficient Catalyst Systems Using Iron Complexes with a Tetradentate PNNP Ligand for the Asymmetric Hydrogenation of Polar Bonds" Angew. Chem. Int. Ed. (2008) 47:940-943.

Mikhailine et al. "New Cyclic Phosphonium Salts Derived from the Reaction of Phosphine-aldehydes with Acid" Journal of Organometallic Chemistry (2010) 695:1824-1830.

IRON(II) CATALYSTS CONTAINING DIIMINO-DIPHOSPHINE TETRADENTATE LIGANDS AND THEIR SYNTHESIS

This application claims the benefit of the priority date of U.S. Provisional patent application No. 61/193,147, filed Oct. 31, 2008 and entitled Iron(Ii) Catalysts Containing Diimino-Diphosphine Tetradentate Ligands And Their Synthesis, the entire subject matter of which is incorporated herein by reference.

TECHNICAL FIELD

The present invention relates to catalytic materials for hydrogenation or asymmetric hydrogenation. In particular, the invention relates to iron (II) complexes containing tetradentate diimino-diphosphine ($P_2N_2$) ligands for the catalytic hydrogenation or asymmetric hydrogenation of carbonyl groups for use in preparing alcohols or non racemic alcohols, respectively. Imine groups can similarly be hydrogenated or asymmetrically hydrogenated to provide amines, or non-racemic amines, respectively. These alcohols and amine products are important raw materials in the manufacturing of chemical products, pharmaceuticals, fragrance and flavours.

BACKGROUND

Asymmetric hydrogenation is an important method for generating single enantiomer molecules that include intermediates and fine chemicals with applications in the pharmaceuticals, biotechnology, agrochemical, food, flavours, essential oils, personal care and advanced materials industries. Each enantiomer may have quite different properties and effectiveness. The use of a drug molecule as a single enantiomer reduces the risk of negative effects of a racemate, increases efficacy and accuracy of dosage, reduces the dosage compared to racemates by one half, with a subsequent reduction in cost and waste, environmental burden including agricultural and human waste run-off. This is particularly true since the US Food and Drug Administration, the European Committee for Proprietary Medicinal Products and other regulatory authorities have required characterization of enantiomers in proposed marketable drug products. Examples of some of the top selling drug products that are chiral are: Lipitor™, Zocor™, Zyprexa™, Norvasc™, Procrit™, Prevacid™, Nexium™, Plavix™, Advair™ and Zoloft™. In 2003 the total global sales for these products amounted to 48.3 billion dollars.

In the biotechnology sector the ability to synthesize enantiomerically pure amino acids, peptides and proteins is of great value. In the agrochemical business about 25% of the members of several classes of pesticides and herbicides exist as enantiomers. Currently the largest scale asymmetric hydrogenation process is the production of the S enantiomer of Metalochlor™.

Volatile, enantiomerically pure alcohols are particularly valuable in the flavours and fragrances industries where each enantiomer provides a distinctive olfactory sensation. They are playing an increasingly important role in aromatherapy.

Single enantiomer helical molecules impart important optical, electronic and magnetic properties to materials and nanomaterials with applications in switches, motors, sensors, polarizers and displays.

In the hydrogenation of complex molecules, the selectivity and activity of the process is dependent on the catalyst structure. This structure must interact with the substrate to provide the diastereomeric transition state of lower energy that leads to the required enantiomer.

Conventional asymmetric hydrogenation catalysts utilize platinum group metals (PGM) ruthenium, osmium, rhodium, iridium, palladium or platinum (De Vries et al., "Handbook of Homogeneous Hydrogenation" Wiley-VCH, volumes 1-3, 2007). Their ability to activate hydrogen gas toward addition to organic compounds is well known. However, these metals present potential toxicity problems and prolonged usage of pharmaceuticals containing traces of these metals might lead to harmful bio-accumulation. PGM are expensive and thereby add to the cost of the final product. In addition, they are in limited supply and will decrease in availability over time.

The direct hydrogenation of carbonyl and/or imine groups in an organic molecule using hydrogen gas is now becoming the preferred "green" method because no waste is produced and the separation of product is easier. Hydrogen is expected to be an even more abundant feedstock as it is used more as a green fuel. In a complimentary way, the catalytic hydrogenation or asymmetric hydrogenation of carbonyl and/or imine groups in an organic molecule by transfer from a hydrogen-donating molecule or mixture has the advantage of operational simplicity by avoiding the use of pressurized hydrogen (Gladiali et al., "Asymmetric transfer hydrogenation: chiral ligands and applications," Chem. Soc. Rev. 35 (2006) pp 226-236).

The reduction of ketones is one of the fundamental reactions in the chemistry field and is used in many chemical transformations towards various products. Asymmetric reduction of the carbonyl group was achieved in the past using chiral catalysts that are based on platinum group metals (PGM) such as ruthenium, rhodium, iridium, palladium or platinum. Usually $^i$PrOH or $H_2$ are used as a reducing agent in those transformations when they are activated by the metal-catalysts. The activation is normally produced via the in situ formation of the catalyst from pre-catalyst by the addition of a strong base.

Reduction catalysis utilizing molecular hydrogen is more attractive compared to the reduction with $^i$PrOH because of the low price of hydrogen gas, product purification simplicity and waste elimination. Reduction catalysis by hydrogen transfer from $^i$PrOH is preferred when pressurized hydrogen gas is not available or convenient.

Chiral alcohols and amines that are produced by the asymmetric hydrogenation or asymmetric transfer hydrogenation of ketones and imines, respectively, are extensively used in the synthesis of pharmaceuticals, agricultural chemicals, fragrances and materials. A non-limiting list of the examples of such compounds is presented below:

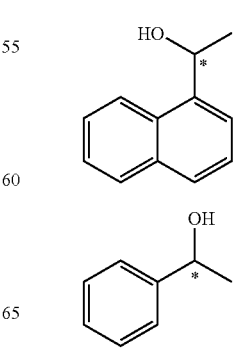

-continued

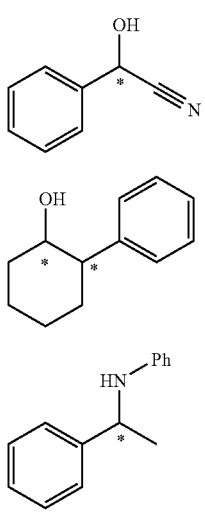

Product 1 can be used in preparation of the (+)-compactin, an HMG-CoA-reductase inhibitor. Product 2 can be used in the synthesis of 2,4-diaminoquinazoline derivatives which are possible SMN2 promoter activators which can be used in the treatment of spinal muscular atrophy. Product 3 may be used as a synthetic building block of the highest selling drug Fluoxetine (Prozac®). Product 4 may be used as a chiral synthetic intermediate in preparation of the benzazepine dopamine antagonist Sch 39 166.

Although some PGM catalytic systems have enzyme-like enantioselectivities and activities, their toxicity and high price make them unattractive for some industrial synthetic transformations.

Attempts have been made to solve this problem. For example, Gao et al. in 1996 in the journal *Polyhedron* (Gao et al. "Synthesis and characterization of iron(2+) and ruthenium (2+) diimino-diphosphine, diamino-diphosphine and diamido-diphosphine complexes," *Polyhedron* 1 (1996), pp. 1241-1251) reported the synthesis of iron complexes with tetradentate ligands. The use and application of their iron complexes towards hydrogenation was not disclosed. They reported the synthesis of two iron complexes with diphosphinediimine ligands 6 and 7: trans-[Fe(NCMe)$_2$(6)](ClO$_4$)$_2$ and trans-[Fe(NCMe)$_2$(7)](ClO$_4$)$_2$.

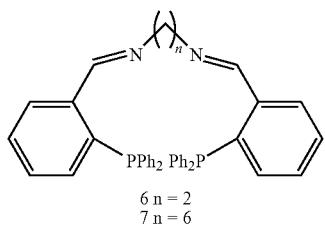

6 n = 2
7 n = 6

They also reported the iron complex with the diphosphinediamine ligand 8.

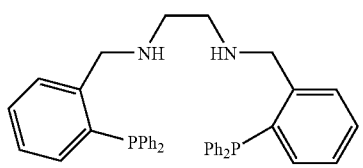

8

Further, Gao et al. in 1996 in the journal *Organometallics* (Gao et al., "A ruthenium(ii) complex with a c-2-symmetrical diphosphine/diamine tetradentate ligand for asymmetric transfer hydrogenation of aromatic ketones," *Organometallics* 15 (1996), pp. 1087-1089) disclosed that ruthenium complexes with the enantiopure ligands 9 ((R,R)-cyP$_2$N$_2$) and 10 are catalysts for the asymmetric transfer hydrogenation of ketones with the latter displaying superior activity and selectivity. Rautenstrauch et al. (Rautenstrauch et al., "Hydrogenation versus Transfer Hydrogenation of Ketones: Two Established Ruthenium Systems Catalyze Both," *Chem. Eur. J.* 9 (2003), pp. 4954-4967; U.S. Pat. No. 6,878,852 B2 5/2005 to Rautenstrauch et al.) showed that similar ruthenium complexes are active for the hydrogenation and asymmetric hydrogenation of ketones.

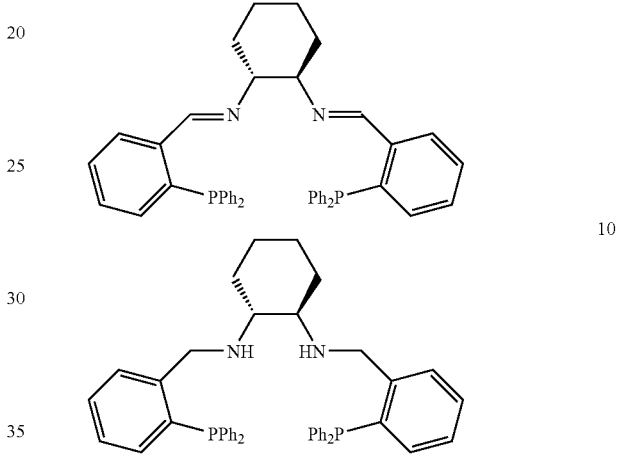

Boaz et al. (U.S. Pat. No. 6,690,115 B2 7/2003 to Boaz et al.; 2006/0135805 A1 to Boaz et al.) made ketone hydrogenation catalysts based on PG metals such as Ru and Rh in complexes of PNNP ligands of the type 11. Here the iron is part of the ferrocenyl substituent on the ligand which is known in the art to provide selectivity and sometimes activity to a PG metal catalyst.

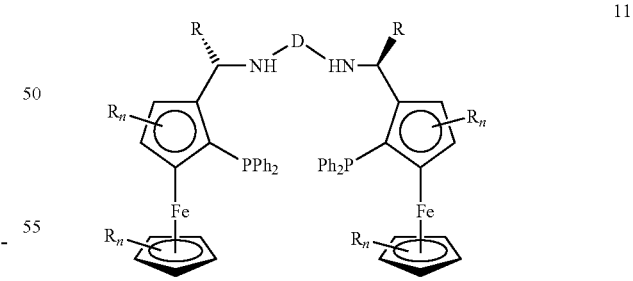

Chen et al. (Chen et al., "Asymmetric transfer hydrogenation of ketones catalyzed by chiral carbonyl iron systems," *Huaxue Xuebao* 62 (2004), pp. 1745-1750) reported an asymmetric transfer hydrogenation system where one of the compounds 10, 12 or 13 of the type P—NH—NH—P are added to [HFe$_3$(CO)$_{11}$]$^-$ to generate in situ catalysts for the transfer of hydrogen from isopropanol to ketones but the activity was low and the nature of the active catalyst was thought to be a cluster containing the three irons. The structure of this catalyst remains unknown. Other iron precursors $Fe(CO)_5$ and $[Fe(C_5H_5)(CO_2]_2$ did not lead to active catalyst mixtures.

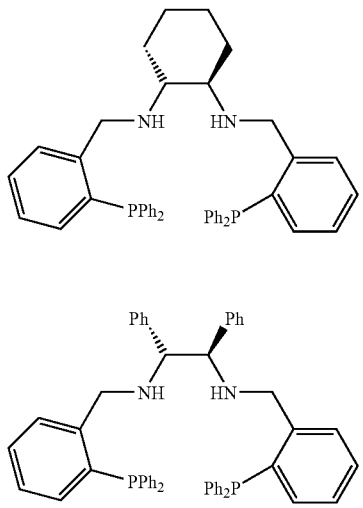

Bianchini et al. (Bianchini et al., "Chemoselective Hydrogen-Transfer Reduction of alpha,beta-Unsaturated Ketones Catalyzed by Isostructural Iron(II), Ruthenium(II), and Osmium(II) cis Hydride eta(2)-Dihydrogen Complexes," *Organometallics* 12 (1993), pp. 3753-3761) reported that iron complexes with a tetradentate $PP_3$ ligand were active for the non-asymmetric hydrogenation of olefins under mild conditions.

Enthaler et al. (Enthaler et al., "Biomimetic transfer hydrogenation of ketones with iron porphyrin catalysts," *Tet. Lett.* 47 (2006), pp. 8095-8099) reported that in situ-generated iron complexes of achiral porphyrin ligands are somewhat active for the hydrogenation of ketones but no asymmetric hydrogenation reaction was possible because of the lack of a chiral ligand.

Casey's group (Casey et al., "An efficient and chemoselective iron catalyst for the hydrogenation of ketones," *J. Am. Chem. Soc.* 129 (2007), pp. 5816-5817) reported that an achiral complex of the type $Fe(arene-OH)H(CO)_2$ is a hydrogenation catalyst but not an asymmetric hydrogenation catalyst for ketones and imines at room temperature. It also catalyzes the hydrogenation of acetophenone by transfer from isopropanol. The complex $[NMe_4][Fe_3H(CO)_{11}]$ catalyzes the complete conversion of ketones to alcohols at 80-100° C. within 1-24 h by using alcohols as the reductant (Jothimony et al. "Mechanism for transfer hydrogenation of ketones to alcohols catalyzed by hydridotriiron undecacarbonylate anion under phase transfer conditions," 52 *J. Molec. Cat.* (1989), pp. 301-304) but this is not an asymmetric reduction. Bart et al. (Bart et al., "Preparation and molecular and electronic structures of iron(0) dinitrogen and silane complexes and their application to catalytic hydrogenation and hydrosilation," *J. Am. Chem. Soc.* 126 (2004), pp. 13794-13795) have reported achiral iron catalysts that hydrogenate olefins under mild conditions.

Thus, there is a need for new catalysts for hydrogenation, asymmetric hydrogenation, transfer hydrogenation, and asymmetric transfer hydrogenation which do not require the use of PGMs.

SUMMARY OF THE INVENTION

In one aspect, there is a provided a hexa-coordinate iron (II) complex comprising a compound of formula (I):

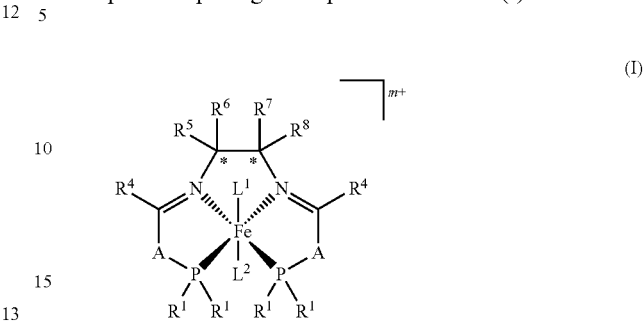

(I)

wherein
each $R^1$ is independently selected from the group consisting of aryl, heteroaryl, $C_1$-$C_8$ alkyl, $C_2$-$C_8$ alkenyl, $C_1$-$C_8$ alkoxy, aryloxy, and cycloalkyl, all of which may be optionally substituted; two geminal $R^1$ groups may combine to form a $C_2$-$C_4$ linear alkyl diradical or $C_3$-$C_8$ branched alkyl diradical, each of which may be optionally substituted, to form a ring together with the phosphorus atom to which they are attached; or two $R^1$ groups, each of which is located on a different phosphorus atom, may combine to form a linker M, wherein M is selected from the group consisting of $C_2$-$C_4$ linear alkyl diradical and $C_3$-$C_8$ branched alkyl diradical, each of which may be optionally substituted, or M may be a diradical ligand with a wide bite angle;

A is selected from:

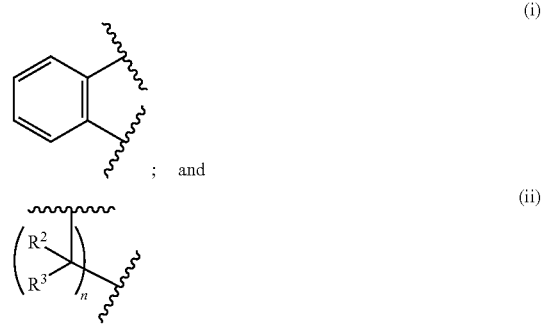

wherein each $R^2$ and $R^3$ are independently selected from the group consisting of H, substituted or unsubstituted $C_1$-$C_8$ alkyl, substituted or unsubstituted $C_2$-$C_8$ alkenyl, substituted or unsubstituted aryl, and substituted or unsubstituted cycloalkyl, and each n is an integer independently selected from 1, 2, and 3;

each $R^4$ is independently selected from the group consisting of H, substituted or unsubstituted $C_1$-$C_8$ alkyl, substituted or unsubstituted $C_2$-$C_8$ alkenyl, substituted or unsubstituted aryl, and substituted or unsubstituted cycloalkyl;

each $R^5$, $R^6$, $R^7$ and $R^8$ is independently selected from the group consisting of H, substituted or unsubstituted $C_1$-$C_8$ alkyl, substituted or unsubstituted $C_2$-$C_8$ alkenyl, substituted or unsubstituted aryl, and substituted or unsubstituted cycloalkyl; $R^5$ and $R^6$, together with the carbon atom to which they are attached, may combine to form a substituted or unsubstituted cycloalkyl ring of size from 5-8 carbons; $R^7$ and $R^8$, together with the carbon atom to which they are attached, may combine to form a substituted or unsubstituted cycloalkyl ring of size from 5-8 carbons; or $R^5$, $R^6$, $R^7$ and $R^8$, together with the carbon atoms to which they are attached, may combine to form a group selected from

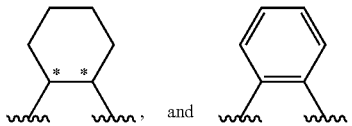 [SMILES: *C1CCCCC1* ; *c1ccccc1*]

each of which may be optionally substituted with one or more substituents selected from the group consisting of $C_1$-$C_8$ alkyl, $C_1$-$C_8$ alkoxy, and halogen atoms;

$L^1$ and $L^2$ are independently selected from the group consisting of CO; hydride; pyridine and derivatives thereof; imidazole and derivatives thereof; halide ion; NCR, CNR and $^-$OR, wherein R is independently selected from the group consisting of aryl, heteroaryl, $C_1$-$C_8$ alkyl, $C_2$-$C_8$ alkenyl and cycloalkyl, all of which may be optionally substituted; $R^aR^bR^cN$ wherein $R^a$, $R^b$, and $R^c$ are independently selected from the group consisting of H and $C_1$-$C_2$ alkyl; and $R^c(CO)R^d$ wherein $R^c$ and $R^d$ are independently selected from the group consisting of $C_1$-$C_8$ alkyl, aryl, and heteroaryl;

m represents the charge of the compound of formula (I) and is 0, +1, or +2; and when m is +1 or +2, the iron (II) complex comprises at least one counter ion to counterbalance the charge of the compound of formula (I);

with the proviso that when A is

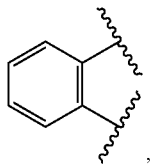 [SMILES: *c1ccccc1*]

then at least one of $L^1$ and $L^2$ must be selected from the group consisting of CO and CNR, wherein R is as defined above.

In another aspect, there is provided a process for the preparation of a hexa-coordinate iron (II) complex of formula (I), the process comprising reacting a phosphinaldehyde precursor of formula (V):

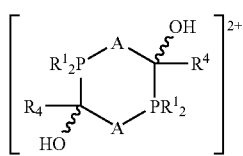

(V)

wherein each $R^1$ is independently selected from the group consisting of aryl, heteroaryl, $C_1$-$C_8$ alkyl, $C_2$-$C_8$ alkenyl, $C_1$-$C_8$ alkoxy, aryloxy, and cycloalkyl, all of which may be optionally substituted; two geminal $R^1$ groups may combine to form a $C_2$-$C_4$ linear alkyl diradical or $C_3$-$C_8$ branched alkyl diradical, each of which may be optionally substituted, to form a ring together with the phosphorus atom to which they are attached; or two $R^1$ groups, each of which is located on a different phosphorus atom, may combine to form a linker M, wherein M is selected from the group consisting of $C_2$-$C_4$ linear alkyl diradical and $C_3$-$C_8$ branched alkyl diradical, each of which may be optionally substituted, or M may be a diradical ligand with a wide bite angle;

A is

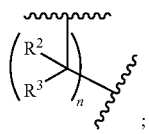

wherein each $R^2$ and $R^3$ are independently selected from the group consisting of H, substituted or unsubstituted $C_1$-$C_8$ alkyl, substituted or unsubstituted $C_2$-$C_8$ alkenyl, substituted or unsubstituted aryl, and substituted or unsubstituted cycloalkyl, and each n is an integer independently selected from 1, 2, and 3;

each $R^4$ is independently selected from the group consisting of H, substituted or unsubstituted $C_1$-$C_8$ alkyl, substituted or unsubstituted $C_2$-$C_8$ alkenyl, substituted or unsubstituted aryl, and substituted or unsubstituted cycloalkyl;

with a diamine of formula (VI):

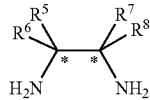

(VI)

wherein each $R^5$, $R^6$, $R^7$ and $R^8$ is independently selected from the group consisting of H, substituted or unsubstituted $C_1$-$C_8$ alkyl, substituted or unsubstituted $C_2$-$C_8$ alkenyl, substituted or unsubstituted aryl, and substituted or unsubstituted cycloalkyl; $R^5$ and $R^6$, together with the carbon atom to which they are attached, may combine to form a substituted or unsubstituted cycloalkyl ring of size from 5-8 carbons; $R^7$ and $R^8$, together with the carbon atom to which they are attached, may combine to form a substituted or unsubstituted cycloalkyl ring of size from 5-8 carbons; or $R^5$, $R^6$, $R^7$ and $R^8$, together with the carbon atoms to which they are attached, may combine to form a group selected from

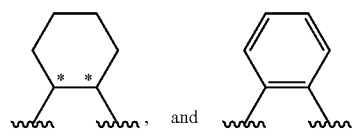

each of which may be optionally substituted with one or more substituents selected from the group consisting of $C_1$-$C_8$ alkyl, $C_1$-$C_8$ alkoxy, and halogen atoms;

in the presence of:

an iron (II) salt;

a ligand selected from the group consisting of $CH_3CN$; pyridine and derivatives thereof; and imidazole and derivatives thereof; and a strong base;

to form the compound of formula (I)

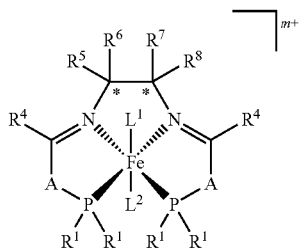

wherein A, $R^1$-$R^8$, and n are as defined above, m is +2, $L^1$ and $L^2$ are both $CH_3CN$; pyridine or a derivative thereof; or imidazole or a derivative thereof;

and adding at least one counter ion to counterbalance the charge of the compound of formula (I).

In another aspect, there is provided, a process for preparing an alcoholic compound wherein said process comprises a step of preparing the alcoholic compound by reducing a ketone or aldehyde with the reaction of hydrogen or a compound donating hydrogen in the presence of a hexa-coordinate iron (II) complex of formula (I), with the proviso that the ketone is not an unsubstituted cycloalkanone.

In still another aspect, there is provided a process for preparing an amine compound wherein said process comprises a step of preparing the amine compound by reducing an imine with the reaction of hydrogen or a compound donating hydrogen in the presence of a hexa-coordinate iron (II) complex of formula (I).

In yet another aspect, there is provided a hydrogenation catalyst comprising a hexa-coordinate iron(II) complex of formula (I)

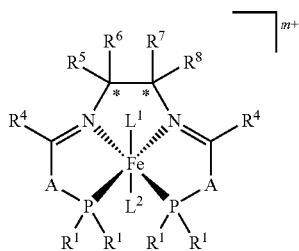

wherein a trans coordination geometry is achieved at iron through nitrogen and phosphorus donor bonds of a tetradentate diimino-diphosphine templated ligand of the formula (II):

$R^1_2P$-A-C($R^4$)=N—C*($R^5R^6$)—C*($R^7R^8$)—N=C($R^4$)-A-$PR^1_2$ (II)

and $L^1$ and $L^2$ are in an axial coordination above and below the templated ligand, respectively, wherein the tetradentate diimino-diphosphine templated ligand is the reaction product of a phosphinaldehyde precursor of formula (V)

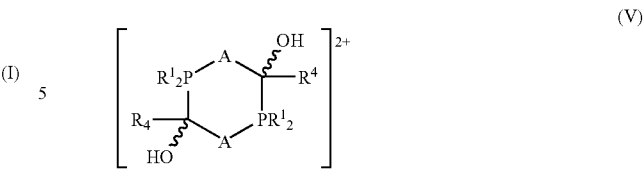

and a diamine precursor of formula (VI)

wherein each $R^1$ is independently selected from the group consisting of aryl, heteroaryl, $C_1$-$C_8$ alkyl, $C_2$-$C_8$ alkenyl, $C_1$-$C_8$ alkoxy, aryloxy, and cycloalkyl, all of which may be optionally substituted; two geminal $R^1$ groups may combine to form a $C_2$-$C_4$ linear alkyl diradical or $C_3$-$C_8$ branched alkyl diradical, each of which may be optionally substituted, to form a ring together with the phosphorus atom to which they are attached; or two $R^1$ groups, each of which is located on a different phosphorus atom, may combine to form a linker M, wherein M is selected from the group consisting of $C_2$-$C_4$ linear alkyl diradical and $C_3$-$C_8$ branched alkyl diradical, each of which may be optionally substituted, or M may be a diradical ligand with a wide bite angle;

A is selected from:

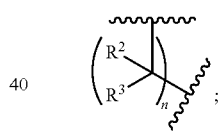

wherein each $R^2$ and $R^3$ are independently selected from the group consisting of H, substituted or unsubstituted $C_1$-$C_8$ alkyl, substituted or unsubstituted $C_2$-$C_8$ alkenyl, substituted or unsubstituted aryl, and substituted or unsubstituted cycloalkyl, and each n is an integer independently selected from 1, 2, and 3;

each $R^4$ is independently selected from the group consisting of H, substituted or unsubstituted $C_1$-$C_8$ alkyl, substituted or unsubstituted $C_2$-$C_8$ alkenyl, substituted or unsubstituted aryl, and substituted or unsubstituted cycloalkyl;

each $R^5$, $R^6$, $R^7$ and $R^8$ is independently selected from the group consisting of H, substituted or unsubstituted $C_1$-$C_8$ alkyl, substituted or unsubstituted $C_2$-$C_8$ alkenyl, substituted or unsubstituted aryl, and substituted or unsubstituted cycloalkyl; $R^5$ and $R^6$, together with the carbon atom to which they are attached, may combine to form a substituted or unsubstituted cycloalkyl ring of size from 5-8 carbons; $R^7$ and $R^8$, together with the carbon atom to which they are attached, may combine to form a substituted or unsubstituted cycloalkyl ring of size from 5-8 carbons; or $R^5$, $R^6$, $R^7$ and $R^8$, together with the carbon atoms to which they are attached, may combine to form a group selected from

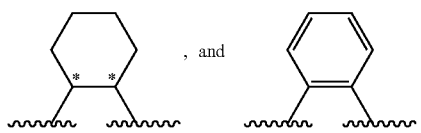 [SMILES: *C1CCCCC1* ; "," ; *c1ccccc1*], and each of which may be optionally substituted with one or more substituents selected from the group consisting of $C_1$-$C_8$ alkyl, $C_1$-$C_8$ alkoxy, and halogen atoms;

$L^1$ and $L^2$ are independently selected from the group consisting of CO; hydride; pyridine and derivatives thereof; imidazole and derivatives thereof; halide ion; NCR, CNR and $^-$OR, wherein R is independently selected from the group consisting of aryl, heteroaryl, $C_1$-$C_8$ alkyl, $C_2$-$C_8$ alkenyl and cycloalkyl, all of which may be optionally substituted; $R^a R^b R^c N$ wherein $R^a$, $R^b$, and $R^c$ are independently selected from the group consisting of H and $C_1$-$C_2$ alkyl; and $R^c(CO)R^d$ wherein $R^c$ and $R^d$ are independently selected from the group consisting of $C_1$-$C_8$ alkyl, aryl, and heteroaryl;

m represents the charge of the compound of formula (I) and is 0, +1, or +2; and when m is +1 or +2, the iron (II) complex comprises at least one counter ion to counterbalance the charge of the compound of formula (I);

with the proviso that when A is

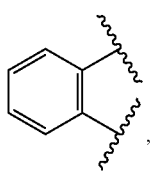, then at least one of $L^1$ and $L^2$ must be selected from the group consisting of CO and CNR, wherein R is as defined above.

In still another aspect, there is provided a process for the preparation of a hexa-coordinate iron (II) complex, the process comprising reacting a phosphinaldehyde precursor of formula (V):

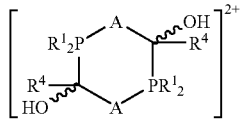

wherein each $R^1$ is independently selected from the group consisting of aryl, heteroaryl, $C_1$-$C_8$ alkyl, $C_2$-$C_8$ alkenyl, $C_1$-$C_8$ alkoxy, aryloxy, and cycloalkyl, all of which may be optionally substituted; two geminal $R^1$ groups may combine to form a $C_2$-$C_4$ linear alkyl diradical or $C_3$-$C_8$ branched alkyl diradical, each of which may be optionally substituted, to form a ring together with the phosphorus atom to which they are attached; or two $R^1$ groups, each of which is located on a different phosphorus atom, may combine to form a linker M, wherein M is selected from the group consisting of $C_2$-$C_4$ linear alkyl diradical and $C_3$-$C_8$ branched alkyl diradical, each of which may be optionally substituted, or M may be a diradical ligand with a wide bite angle;

A is

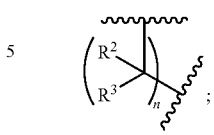;

wherein each $R^2$ and $R^3$ are independently selected from the group consisting of H, substituted or unsubstituted $C_1$-$C_8$ alkyl, substituted or unsubstituted $C_2$-$C_8$ alkenyl, substituted or unsubstituted aryl, and substituted or unsubstituted cycloalkyl, and each n is an integer independently selected from 1, 2, and 3;

each $R^4$ is independently selected from the group consisting of H, substituted or unsubstituted $C_1$-$C_8$ alkyl, substituted or unsubstituted $C_2$-$C_8$ alkenyl, substituted or unsubstituted aryl, and substituted or unsubstituted cycloalkyl;

with a diamine of formula (VI):

wherein each $R^5$, $R^6$, $R^7$ and $R^8$ is independently selected from the group consisting of H, substituted or unsubstituted $C_1$-$C_8$ alkyl, substituted or unsubstituted $C_2$-$C_8$ alkenyl, substituted or unsubstituted aryl, and substituted or unsubstituted cycloalkyl; $R^5$ and $R^6$, together with the carbon atom to which they are attached, may combine to form a substituted or unsubstituted cycloalkyl ring of size from 5-8 carbons; $R^7$ and $R^8$, together with the carbon atom to which they are attached, may combine to form a substituted or unsubstituted cycloalkyl ring of size from 5-8 carbons; or $R^5$, $R^6$, $R^7$ and $R^8$, together with the carbon atoms to which they are attached, may combine to form a group selected from

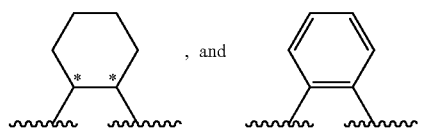 [SMILES: *C1CCCCC1* ; "," ; *c1ccccc1*], and each of which may be optionally substituted with one or more substituents selected from the group consisting of $C_1$-$C_8$ alkyl, $C_1$-$C_8$ alkoxy, and halogen atoms;

in the presence of:

an iron (II) salt;

a ligand selected from the group consisting of $CH_3CN$; pyridine and derivatives thereof; and imidazole and derivatives thereof; and a strong base;

and further reacting the reaction product of the foregoing steps with CO to produce a compound of formula (VIIIa):

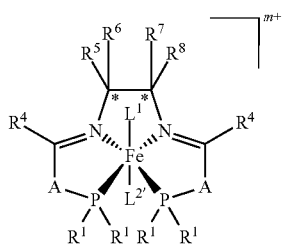

(VIIIa)

wherein A, $R^1$-$R^8$, and n are as defined above, $L_1$ is CO, $L^{2'}$ is Br, and m is +1;
and adding a counter ion to counterbalance the charge of the compound of formula (VIIIa).

A process for preparing a phosphonium dimer of formula (XIII) is provided:

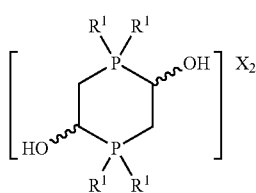

(XIII)

wherein $R^1$ is selected from the group consisting of $C_1$-$C_8$ alkyl, $C_1$-$C_8$ substituted alkyl, cycloalkyl, and substituted cycloalkyl, and X is selected from the group consisting of Br and I, the process comprising:
reacting a compound of formula (XI):

(XI)

wherein $R^1$ is as defined above;
with a compound of formula (XII):

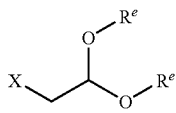

(XII)

wherein X is as defined above, and $R^e$ is $C_1$-$C_8$ alkyl, or the two Re can combine to form a $C_2$-$C_3$ linear alkyl diradical;
and heating the reaction product in the presence of water to form the phosphonium dimer of formula (XIII).

DETAILED DESCRIPTION

Iron (II) complexes with PNNP donor ligands as catalytic materials for the hydrogenation, asymmetric hydrogenation, transfer hydrogenation, and/or asymmetric transfer hydrogenation of ketones and imines are disclosed.

The asymmetric hydrogenation technology described herein that provides a specified enantiomer enables a more economical, safer, efficient, and greener chemical way to generate compounds that are significantly enriched in the required enantiomer.

As noted above, conventional asymmetric hydrogenation catalysts utilize platinum group metals (PGM) ruthenium, osmium, rhodium, iridium, palladium or platinum (De Vries et al., "Handbook of Homogeneous Hydrogenation" Wiley-VCH, volumes 1-3, 2007). PGM are expensive and thereby add to the cost of the final product. In addition, they are in limited supply and not readily available. By contrast, iron is inexpensive, abundant and biocompatible. An unexpected feature of the disclosed catalysts is the high activity that they display in the activation of hydrogen gas toward the hydrogenation of ketones and in the activation of hydrogen-donor molecules such as isopropanol toward the transfer hydrogenation of ketones and imines.

In one embodiment, there is provided a hexa-coordinate iron (II) complex comprising a compound of formula (I):

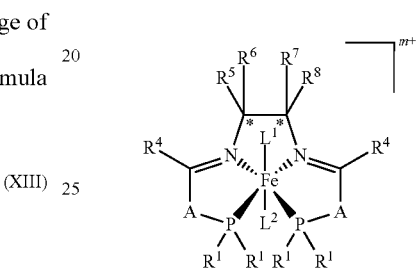

(I)

wherein
each $R^1$ is independently selected from the group consisting of aryl, heteroaryl, $C_1$-$C_8$ alkyl, $C_2$-$C_8$ alkenyl, $C_1$-$C_8$ alkoxy, aryloxy, and cycloalkyl, all of which may be optionally substituted; two geminal $R^1$ groups may combine to form a $C_2$-$C_4$ linear alkyl diradical or $C_3$-$C_8$ branched alkyl diradical, each of which may be optionally substituted, to form a ring together with the phosphorus atom to which they are attached; or two $R^1$ groups, each of which is located on a different phosphorus atom, may combine to form a linker M, wherein M is selected from the group consisting of $C_2$-$C_4$ linear alkyl diradical and $C_3$-$C_8$ branched alkyl diradical, each of which may be optionally substituted, or M may be a diradical ligand with a wide bite angle;
A is selected from:

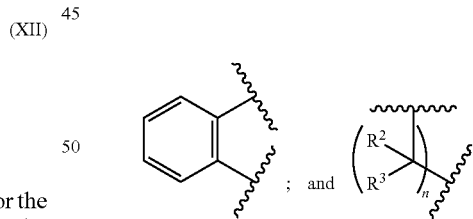

wherein each $R^2$ and $R^3$ are independently selected from the group consisting of H, substituted or unsubstituted $C_1$-$C_8$ alkyl, substituted or unsubstituted $C_2$-$C_8$ alkenyl, substituted or unsubstituted aryl, and substituted or unsubstituted cycloalkyl, and each n is an integer independently selected from 1, 2, and 3;
each $R^4$ is independently selected from the group consisting of H, substituted or unsubstituted $C_1$-$C_8$ alkyl, substituted or unsubstituted $C_2$-$C_8$ alkenyl, substituted or unsubstituted aryl, and substituted or unsubstituted cycloalkyl;
each $R^5$, $R^6$, $R^7$ and $R^8$ is independently selected from the group consisting of H, substituted or unsubstituted $C_1$-$C_8$ alkyl, substituted or unsubstituted $C_2$-$C_8$ alkenyl, substituted or unsubstituted aryl, and substituted or unsubstituted cycloalkyl; $R^5$ and $R^6$, together with the carbon atom to which they are attached, may combine to form a substituted or unsubstituted cycloalkyl ring of size from 5-8 carbons; $R^7$ and $R^8$, together with the carbon atom to which they are attached, may combine to form a substituted or unsubstituted cycloalkyl ring of size from 5-8 carbons; or $R^5$, $R^6$, $R^7$ and $R^8$, together with the carbon atoms to which they are attached, may combine to form a group selected from

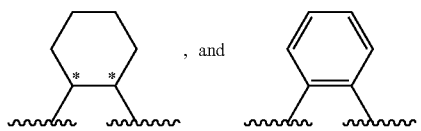 [SMILES: *C1CCCCC1* ; "," ; *c1ccccc1*], and each of which may be optionally substituted with one or more substituents selected from the group consisting of $C_1$-$C_8$ alkyl, $C_1$-$C_8$ alkoxy, and halogen atoms;

$L^1$ and $L^2$ are independently selected from the group consisting of CO; hydride; pyridine and derivatives thereof; imidazole and derivatives thereof; halide ion; NCR, CNR and $^-$OR, wherein R is independently selected from the group consisting of aryl, heteroaryl, $C_1$-$C_8$ alkyl, $C_2$-$C_8$ alkenyl and cycloalkyl, all of which may be optionally substituted; $R^a R^b R^c N$ wherein $R^a$, $R^b$, and $R^c$ are independently selected from the group consisting of H and $C_1$-$C_2$ alkyl; and $R^c(CO)R^d$ wherein $R^c$ and $R^d$ are independently selected from the group consisting of $C_1$-$C_8$ alkyl, aryl, and heteroaryl;

m represents the charge of the compound of formula (I) and is 0, +1, or +2; and when m is +1 or +2, the iron (II) complex comprises at least one counter ion to counterbalance the charge of the compound of formula (I);

with the proviso that when A is

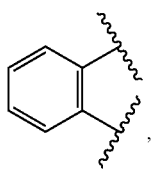 [SMILES: *c1ccccc1* ; ","], then at least one of $L^1$ and $L^2$ must be selected from the group consisting of CO and CNR, wherein R is as defined above.

In another embodiment, a trans coordination geometry is achieved at iron through nitrogen and phosphorus donor bonds of a tetradentate diimino-diphosphine templated ligand of the formula (II):

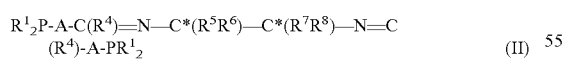 (II)

and $L^1$ and $L^2$ are in an axial coordination above and below the templated ligand, respectively.

In one embodiment, the at least one counter ion is selected from $BF_4^-$; $PF_6^-$; $SbF_6^-$; $ClO_4^-$; $CH_3SO_3^-$; $CF_3SO_3^-$; $C_6H_5SO_3^-$; $p\text{-}CH_3C_6H_4SO_3^-$; $FeCl_4^{2-}$; $FeBr_4^{2-}$; $B(R^*)_4^-$, wherein $R^*$ is selected from phenyl, $C_6H_3(CF_3)_2$ and $C_6F_5$; halides; pseudohalides; $C_1$-$C_8$ alkoxides; and aryloxides. In another embodiment, the at least one counter ion is $BF_4^-$. In another embodiment, the at least one counter ion is $BPh_4^-$.

In another embodiment, $R^1$ is substituted or unsubstituted aryl. In other embodiments, $R^1$ is phenyl.

In another embodiment, A is

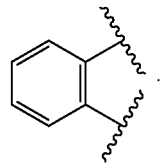

In another embodiment, $R^4$ is H. In yet another embodiment, $R^5$, $R^6$, $R^7$ and $R^8$, together with the carbon atoms to which they are attached, combine to form

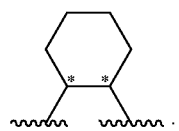

In certain embodiments, the chiral carbon atoms denoted by asterisks both have an R configuration. In other embodiments, the chiral carbon atoms denoted by asterisks both have an S configuration.

In still another embodiment, A is

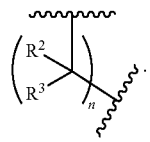

In another embodiment, $R^4$ is H. In another embodiment, $R^2$=$R^3$=H. In yet another embodiment, n=1.

In another embodiment, $R^5$=$R^8$=substituted or unsubstituted aryl and $R^6$=$R^7$=H. In another embodiment, $R^5$=$R^8$=phenyl. In still another embodiment, the chiral carbon atoms bearing the substituents $R^5$ and $R^6$, and $R^7$ and $R^8$, respectively, both have an R configuration. In another embodiment, these chiral carbon atoms have an S configuration.

In another embodiment, $R^4$=$R^5$=$R^6$=$R^7$=$R^8$=H.

In another embodiment, $L^1$ and $L^2$ are $CH_3CN$. In still another embodiment, $L^1$ is $CH_3CN$ and $L^2$ is selected from CO or CNR, wherein R is $C_1$-$C_8$ alkyl. In another embodiment, $L^2$ is CNtBu.

In another embodiment, the hexa-coordinate iron (II) complex comprises a compound having the structure:

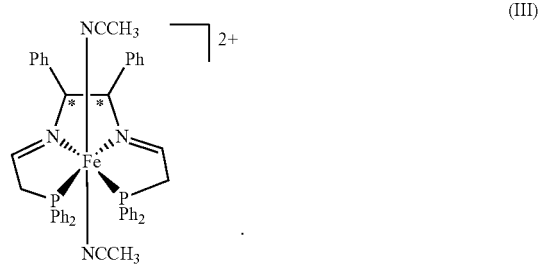

In another embodiment, the chiral carbon atoms denoted by asterisks both have an R configuration. In another embodiment, the chiral carbon atoms denoted by asterisks both have an S configuration.

As noted above, the A symbol represents the bridging group —$(CR^2R^3)_n$. In one embodiment, n is 1, $R^3$ is H and $R^2$ is H. In other embodiments, $R^3$ is H and $R^2$ may be selected from aryl or $C_1$-$C_8$ alkyl, each of which may be optionally substituted. When $R^2 \neq R^3$, the carbon bearing these substituents is chiral and may be enantiopure.

In other embodiments, n may be 2, and A is then —$CR^2R^3CR^2R^3$—. In further embodiments, n may be 3 and A is then —$CR^2R^3CR^2R^3CR^2R^3$—. In one embodiment, all $R^3$ may be H. In another embodiment, each $R^3$ may be different. Likewise, the $R^2$ groups may be the same or different.

In another embodiment, $R^5$, $R^6$, $R^7$ and $R^8$ can be selected to produce enantiopure structures. For instance, the cyclohexyldiyl structure noted above may be present as the (R,R) or (S,S) enantiopure isomer (having regard to the chiral carbon atoms denoted by asterisks).

The various chemical terms used herein are to be given their ordinary meaning as would be understood by persons skilled in the art, unless provided otherwise.

The following chemical terms presently described apply to all compounds and processes disclosed herein, unless provided otherwise.

A "templated ligand" is a molecule that forms from precursor parts that coordinate to a metal ion at geometrically defined positions such as octahedral or square planar, for example, and bond together. The metal ion acts as template for the formation of this ligand. Given the same reaction conditions, but in the absence of the metal template, the precursor parts usually either do not react, or do react but form a mixture of products, none of which have the structure of the templated ligand.

The compounds of formula (I) disclosed herein are referred to herein as "catalysts". However, it will be understood by a person of skill in the art that further study may reveal that these compounds are in theory "pre-catalysts" and are converted to an active form during the hydrogenation reactions.

The term "$C_1$-$C_8$ alkyl" as used herein either alone or in combination with another substituent means acyclic, linear or branched chain alkyl substituent containing from one to eight carbons and includes for example, methyl, ethyl, 1-methylethyl, 1-methylpropyl, 2-methylpropyl, butyl and the like.

The term "$C_2$-$C_8$ alkenyl", as used herein, either alone or in combination with another radical, is intended to mean an unsaturated, acyclic linear chain radical containing from two to eight carbon atoms, at least two of which are bonded to each other by a double bond. Examples of such radicals include, but are not limited to, ethenyl (vinyl), 1-propenyl, 2-propenyl, and 1-butenyl. The alkenyl groups may contain any number of double bonds.

The term "aryl" as used herein, either alone or in combination with another substituent, means an aromatic monocyclic system containing 6 carbon atoms or an aromatic bicyclic system containing 10 carbon atoms. The rings may have substituents including alkyl groups or alkoxy groups. For instance, a phenyl ring may have substituents such as in the 3 and 5 positions, or 2 and 6 positions, or in the 4 position. The term "aryl" includes but is not limited to a phenyl, tolyl (substituted aryl) or naphthyl group.

The term "heteroaryl" as used herein, either alone or in combination with another substituent means a 5, 6, 7, or 8-membered unsaturated heterocycle containing one oxygen or sulfur or from one to 4 nitrogen heteroatoms and which form an aromatic system. For example, the term "heteroaryl" includes a furyl, pyridyl, or quinolinyl group.

The term "cycloalkyl" as used herein, either alone or in combination with another substituent, means a cycloalkyl substituent that includes for example, but is not limited to, cyclopropyl, cyclobutyl, cyclopentyl, cyclohexyl and cycloheptyl The term "alkoxy" as used herein, either alone or in combination with another radical, means the radical —O—$(C_{1-n})$ alkyl wherein the alkyl group contains 1 or more carbon atoms, and includes for example methoxy, ethoxy, propoxy, 1-methylethoxy, butoxy, cyclohexyloxy and 1,1-dimethylethoxy. "Alkoxide" refers to the radial $^-$O—$(C_{1-n})$ alkyl bearing a negative charge.

The term "aryloxy" as used herein, either alone or in combination with another radical, means the radical —O-aryl wherein aryl is defined as above, such as phenyl.

The term "aromatic diradical" includes groups such as benzo, as well as naphthyl diradical, binaphthyl diradical, and bisoxynaphthyl diradical as derived from BINOL. The term "branched alkyl diradical" includes groups such as 1,4-dimethylbutanediyl. In one aspect, the branched alkyl diradical may have between 3 and 8 carbon atoms. Such diradicals may be enantiopure. The term "linear alkyl diradical" includes $C_2$-$C_4$ linear alkyl diradicals such as 1,2-ethylene, 1,3-propylene, and 1,4-butylene.

The term "diradical that spans a wide bite angle" refers to aromatic diradicals such as naphthyl diradicals or tricyclic groups such as the 4,5-diradical of 9,9-dimethylxanthene and other groups described in the article by Kramer et al. Acc. Chem. Res. 2001, 34, 895-904, the contents of which are hereby incorporated herein by reference.

The term "halogen" refers to F, Cl, Br, and I. The term "halide ion" refers to a halogen atom bearing a negative charge.

The term "pseudohalide" refers to anions that behave chemically like halides. These include $OCN^-$, $SCN^-$, $CN^-$ and $NNN^-$.

As noted above, certain of the $R^1$-$R^8$ groups may be optionally substituted. Those of skill in the art will understand that a suitable substituent includes, for example, methyl substituents on aryl groups to generate tolyl or xylyl groups and the like. Suitable substituents for aryl, heteroaryl, and cycloalkyl functionalities include $C_1$-$C_8$ alkyl, branched or linear, alkoxy or halogen atoms. Suitable substituents for each "R" group mentioned in the claims include methyl, isopropyl, tertiary-butyl and phenyl.

It is to be understood that a suitable substituent is a substituent that does not interfere with the formation of the desired product by the claimed processes and methods disclosed herein. It is understood, of course, that the R groups defined herein ($R^1$-$R^8$, etc.) will not contain any substitution or substitution patterns which are sterically impractical and/or synthetically non-feasible.

As noted above, the $L^1$, $L^2$ symbols, taken separately, represent simultaneously or independently CO; hydride; pyridine and derivatives thereof, including but not limited to 4-picoline or 3-picoline; imidazole and derivatives thereof, including but not limited to N-methyl imidazole; halide ion; NCR, CNR and $^-$OR, wherein R is independently selected from aryl, heteroaryl, $C_1$-$C_8$ alkyl, $C_2$-$C_8$ alkenyl and cycloalkyl, all of which may be optionally substituted; $R^a R^b R^c N$ wherein $R^a$, $R^b$, and $R^c$ are independently selected from H and $C_1$-$C_2$ alkyl; and $R^c(CO)R^d$ wherein $R^c$ and $R^d$ are independently selected from $C_1$-$C_8$ alkyl, aryl, and heteroaryl.

The charge on the complex (m) depends on the nature of the P—N—N—P ligand and the ligands $L^1$ and $L^2$ and can vary from 0 to +2. The charge m+ on the metal is 2+ when the ligands $L^1$ and $L^2$ are neutral, 1+ when one of $L^1$ or $L^2$ is anionic, 0 when both $L^1$ and $L^2$ are anionic.

To counterbalance this charge in the metal complex salt, at least one counter ion is present. The term "counter ion" refers to an ion that is associated with the compounds of formula (I) disclosed herein in order to counterbalance the charge of the compound of formula (I) in the iron (II) complex. Such counter ions may include for example anions selected from the group comprising $BF_4^-$; $PF_6^-$; $SbF_6^-$; $ClO_4^-$; $CH_3SO_3^-$; $CF_3SO_3^-$; $C_6H_5SO_3^-$; p-$CH_3C_6H_4SO_3^-$; $FeCl_4^{2-}$; $FeBr_4^{2-}$; $B(R^*)_4^-$, wherein R* is selected from phenyl, $C_6H_3(CF_3)_2$ and $C_6F_5$; halides; pseudohalides; alkoxides such as $C_1$-$C_8$ alkoxides and aryloxides such as phenoxide.

Compounds donating hydrogen include lower alcohols such as methanol, ethanol, propanol, 2-propanol or butanol, and formic acid.

In particular the enantiopure complex (i) is useful for hydrogenation of ketones and imines, asymmetric hydrogenation of prochiral ketones and imines, and is useful as a precursor for the complex (ii). Complex (i) has been crystallized as the $BF_4^-$ and the $BPh_4^-$ salt (see Example 1) and characterized by elemental analyses, NMR, IR, MS and single crystal X-ray diffraction. The (S,S)-enantiomer of complex (i) has also been prepared.

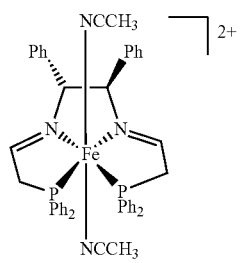
(i)

The performance of the catalyst (i) was tested on 10 different aromatic ketones according to the reaction Scheme 1

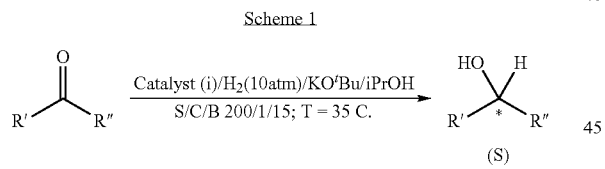

where S:C:B refers to the substrate to catalyst to base ratio. The procedure of the catalytic runs was performed as follows:

TABLE 1

The hydrogenation of ketones catalyzed by (i) and base $KO^tBu$ (S/C/B = 200/1/15) in 9 mL isopropanol at 35° C. under 10 atm $H_2$.[a]

| Entry | Substrate | Time (min) | Conv. (%) | e.e. (S) (%) |
|---|---|---|---|---|
| 1 | Ph-CO-Me | 30 | 40-90 | 81 |
| 2 | Ph-CO-Et | 25 | 35-80 | 92 |
| 3 | Ph-CO-iPr | 30 | 5 | 99 |
| 4 | Ph-$CH_2$—$CH_2$—CO-Me | 25/50 | 45-90/ 56-98 | 1 |
| 5 | (4'-$ClC_6H_4$)—CO-Me | 20 | 55-91 | 91 |
| 6 | (4'-$MeOC_6H_4$)—CO-Me | 20 | 60-94 | 88 |

TABLE 1-continued

The hydrogenation of ketones catalyzed by (i) and base $KO^tBu$ (S/C/B = 200/1/15) in 9 mL isopropanol at 35° C. under 10 atm $H_2$.[a]

| Entry | Substrate | Time (min) | Conv. (%) | e.e. (S) (%) |
|---|---|---|---|---|
| 7 | (3'-$ClC_6H_4$)—CO-Me | 180 | 10-45 | 82 |
| 8 | (3'-$BrC_6H_4$)—CO-Me | 30 | 5-30 | 86 |
| 9 | (2'-$ClC_6H_4$)—CO-Me | 30 | 35-58 | 75 |
| 10 | 1-Acetonaphthone | 360 | 55-96 | 95 |

[a]In the $N_2$ glovebox, the iron complex (10 mg, 0.007 mmol), $KO^tBu$ (12.3 mg, 0.107 mmol) and the substrate were separately dissolved in the 3 mL of 2-propanol, each. The resulting solutions in the order substrate, then base, and then catalyst were injected into a 50 cm³ Parr hydrogenator reactor at the desired pressure and temperature, maintained by use of a Fischer Scientific Isotemp 1016D water bath under a hydrogen atmosphere..

Complex (ii), shown below, has been crystallized as the $BPh_4^-$ salt (see Example 2) and characterized by elemental analyses, NMR, IR, MS and single crystal X-ray diffraction. The (S,S)-enantiomer has also been prepared and completely characterized. Enantiopure complex (ii) is useful for the transfer hydrogenation of ketones and imines and asymmetric transfer hydrogenation of prochiral ketones and imines.

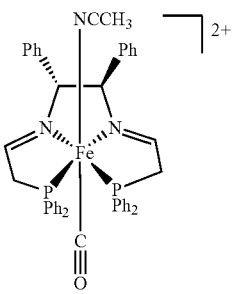
(ii)

TABLE 2

The transfer hydrogenation of ketones to the (S) alcohols catalyzed by (ii) and base $KO^tBu$ (S/C/B = 1600/1/8 unless specified) isopropanol at 22° C.[a]

| Entry | Substrate | Time (min) | Conv. % | ee % |
|---|---|---|---|---|
| 1 | Ph-CO-Me[b] | 30 | 90 | 83 |
| 2 | Ph-CO-Et[c] | 50 | 84 | 93 |
| 3 | (4-$ClC_6H_4$)—CO-Me[c] | 50 | 93 | 70 |
| 4 | (4-MeO—$C_6H_4$)—CO-Me[c] | 50 | 78 | 81 |
| 5 | 1-acetonaphthone[d] | 50 | 93 | 95 |
| 6 | Ph-CO-$^iPr$[c] | 50 | 89 | 91 |

[a]In the $N_2$ glovebox, the iron complex (ii) (2.0 mg, 0.0014 mmol), KOtBu (1.3 mg, 0.0114 mmol) and ketone (2.2 mmol) were separately dissolved in the 5 mL of 2-propanol, each. The resulting solutions were added to a vial charged with a stirring bar in the order: substrate, catalyst followed by base. The samples of the reaction mixture were analyzed by GC.
[b]in 15 mL isopropanol with S/C/B 2000/1/8.
[c]in 12 mL isopropanol.
[d]in 14 mL isopropanol.

The enantiopure complex trans-[Fe(NCMe)(CO)(9)](BF$_4$)$_2$ (iii), wherein 9 is as defined above:

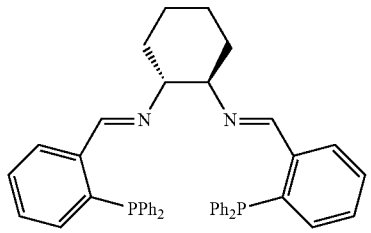

has also been prepared. This complex is inactive for catalytic hydrogenation directly from H$_2$ gas but is useful for the asymmetric transfer hydrogenation of prochiral ketones and is useful for the transfer hydrogenation of ketones and imines. Complex (iii) has been crystallized as the BF$_4^-$ (see Example 4) and the BPh$_4^-$ salt and characterized by elemental analyses, NMR, IR, MS and single crystal X-ray diffraction. The (S,S)-enantiomer of complex (iii) has also been prepared and characterized. The enantiopure complex trans-[Fe(NCMe)(CN$^t$Bu)(9)](BF$_4$)$_2$ (iv) has also been prepared and characterized (see Example 5).

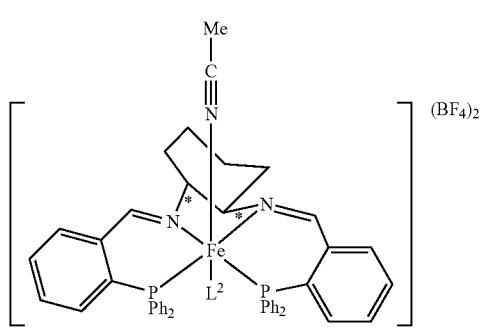

L$^2$ = CO, * = R configuration
L$^2$ = $^t$BuNC, * = R configuration

TABLE 3

Transfer hydrogenation of ketones and imines from 2-propanol catalyzed by (iii) and KOtBu (S/C/B = 200/1/8) at 22° C.[a]

| Entry | Substrate | Time (h) | Conv. (%) | e.e. (%) | TOF[e] (h$^{-1}$) |
|---|---|---|---|---|---|
| 1[b] | Ph-CO-Me | 0.4 | 95 | 29 (S) | 907 |
| 2[c] | Ph-CO-Me | 0.7 | 33 | 39 (S) | 93 |
| 3 | Ph-CO-Me | 0.4 | 95 | 33 (S) | 454 |
| 4 | (2'-Cl—C$_6$H$_4$)—CO-Me | 0.2 | >99 | 18 (S) | 995 |
| 5 | (3'-Cl—C$_6$H$_4$)—CO-Me | 0.4 | 99 | 24 (S) | 495 |
| 6 | (4'-Cl—C$_6$H$_4$)—CO-Me | 0.2 | 94 | 26 (S) | 938 |
| 7 | (4'-Br—C$_6$H$_4$)—CO-Me | 0.2 | 93 | 33 (S) | 930 |
| 8 | (4'-Me-C$_6$H$_4$)—CO-Me | 0.6 | 86 | 33 (S) | 279 |
| 9 | (4'-OMe-C$_6$H$_4$)—CO-Me | 0.5 | 69 | 23 (S) | 260 |
| 10 | Ph-CO-Et | 3.6 | 95 | 61 (S) | 26 |
| 11 | C$_{10}$H$_7$—CO-Me[d] | 0.3 | 94 | 25 (S) | 564 |
| 12 | Ph-CO-Ph | 0.4 | 94 | — | 470 |
| 13 | Ph-(CH$_2$)$_2$—CO-Me | 0.6 | 100 | 29 (S) | 315 |
| 14 | Ph-CHO | 2.4 | 94 | — | 77 |
| 15 | Ph-CH=N-Ph | 17 | 100 | — | 12 |
| 16 | Ph-CMe=N-Ph | 17 | <5 | — | — |
| 17 | Cyclohexanone | 17 | 0 | — | — |

[a] In an Ar or N$_2$ glovebox at 22° C., the iron complex (5 mg, 0.005 mmol, [Cat] = 1.04 mM), KOtBu (5 mg, 0.045 mmol) and the substrate (200 equiv) were stirred in 5 mL of 2-propanol. The conversion and enantiomeric excess of the products were determined by NMR spectroscopy and GC.
[b] S:C:B = 400:1:8, [Cat] = 0.1 mM, 10 mL iPrOH.
[c] S:C:B = 200:1:2, [Cat] = 0.1 mM, 5 mL iPrOH.
[d] C$_{10}$H$_7$—CO-Me = 2-acetonaphthone.
[e] TOF = turn over frequencies.

As can be seen from Table 3, the electronic properties of the substituents on the phenyl ring of the ketone changed the reduction rate but had less effect on the enantioselectivity (18-33%). An acetophenone substituted in the para position by an electron releasing group, such as 4'-methyl and 4'-methoxy, is reduced more slowly than acetophenone (entries 3, 8 and 9). The chloro substituted acetophenones are all reduced faster, especially for the ortho position (entries 3-7). This trend is opposite to the generally observed trend for Noyori's transfer hydrogenation catalysts in which an ortho-Cl substitution decreases the rate of the reduction (S. Hashiguchi, A. Fujii, J. Takehara, T. Ikariya, R. Noyori, J. Am. Chem. Soc. 1995, 117, 7562). The catalyst (iii) with KOtBu is also efficient for the transfer hydrogenation of propiophenone, 2-acetonaphthone, benzophenone, benzylacetone, benzaldehyde and N-benzylideneaniline (entries 11-15). The hydrogenation of propiophenone gave 1-phenylpropanol in 61% e.e (S) (entry 10). The more difficult ketimine N-phenyl-(1-phenylethylidene)amine (Ph-CMe=N-Ph) was only partially reduced (<5%) after 18 h under the same conditions (entry 16), while cyclohexanone was not hydrogenated (entry 17). Transfer hydrogenation of unsaturated ketones was complicated by some reduction of the C=C double bond (Scheme 2).

Scheme 2. Transfer hydrogenation of unsaturated ketones.

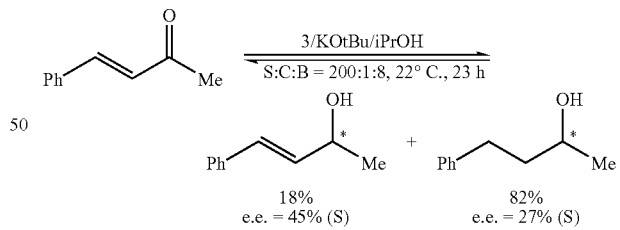

Complex (iv) is useful for the asymmetric transfer hydrogenation of ketones. Complex (iv) was used in the transfer hydrogenation of acetophenone, using the same reaction conditions as noted for complex (iii) (see [a] in Table 3 above). After 2.6 hours the conversion was 34% and the e.e. was 76% (S).

The mechanism of the catalysis is uncertain. The tetradentate ligand complex may be hydrogenated in the reaction medium to produce the amine intermediate [FeH(CO){(R, R)-cyP$_2$(NH)$_2$}]$^+$; however, such a hydride has not yet been synthesized or observed in the catalytic solution. Such a complex might be expected to transfer a hydride from iron and a proton from nitrogen to polar bonds in an outer sphere hydrogenation, the mechanism postulated for the related complexes [RuH$_2${(S,S)-cyP$_2$(NH)$_2$}][15] and [RuH$_2${PPh$_2$(o-C$_6$H$_4$)CH$_2$NHCMe$_2$CMe$_2$NHCH$_2$(o-C$_6$H$_4$)PPh$_2$}] (T. Li, R. Churlaud, A. J. Lough, K. Abdur-Rashid, R. H. Morris, Organometallics 2004, 23, 6239). Since there is poor chemoselectivity for the reduction of the C=O bond versus the C=C during the hydrogenation of trans-4-phenyl-3-buten-2-one, another mechanism might be involved.

During the transfer hydrogenation of acetophenone catalyzed by (iii) (entry 3, Table 3), the $^{31}$P{1H} NMR shows an AB pattern at 56 and 74 ppm (d, $^2J_{P-P}$=28 Hz) due to an, as yet, unidentified intermediate. There is also a singlet for the free ligand 9 (R,R)-cyP$_2$N$_2$, and some other minor, unassigned peaks at 29 and −12.3 ppm. For the reaction catalyzed by (iv), the AB pattern for the intermediate is observed at 54 and 58 ppm (d, $^2J_{P-P}$=31 Hz). This intermediate decomposes upon attempt to isolate it from the catalytic mixture. Without being bound by theory, it is thought that it might be a complex such as [Fe(CO)(X){(R,R)-cyP$_2$N$_2$}](BF$_4$), X=alkoxide or hydride, but further study is required.

The observation of free PNNP ligand in the catalytic solution may suggest the formation of colloidal iron; however, there is evidence that the active catalyst is homogeneous instead of heterogeneous in that the reaction solutions are clear. The e.e. of the product alcohols are reproducible. There is no poisoning of catalysis by mercury when it is added during the reaction (C. A. Jaska, I. Manners, J. Am. Chem. Soc. 2004, 126, 9776).

As it follows from Table 2, TOF (turn over frequencies), TON (turn over numbers) and enantioselectivity of the catalyst (ii) are much higher compared to the catalysts (iii) and (iv). At a certain moment of the reaction when equilibrium between product and a substrate is established, catalytic racemization of the product starts taking place. It is hard to propose a reliable mechanistic explanation for such behavior of the catalyst at this point of investigation, but the conditions of the reduction can be optimized, so the product can be obtained in high yields and enantiopurity. When a smaller amount of the base is used the rate of the reaction is lower and thus the time at which racemization is taking place can be defined. If the reaction is quenched by simple exposure to air at this point of the process, high enantioselectivity and yields of the reaction can be achieved. Those conditions have a disadvantage: the overall rate of the reaction and TOF are reduced. In order to reach high enantioselectivity and conversion of the process the substrate concentration was increased. That increased the time of the reaction enough to determine when the equilibrium is established without reduction of the TOF and product was obtained in good ee, conversion and excellent TOF and TON.

Yellow solutions of complex (iii) are stable to oxidation in air for at least one day. The $^1$H NMR spectrum of (iii) showed the presence of a singlet for the imine protons at 9.11 ppm while the $^{13}$C{1H} NMR spectrum displayed a pseudo-triplet for the carbonyl carbon. The $^1$H NMR spectrum of complex (iv) has two distinct resonances for the imines protons. The $^{31}$P{1H} NMR spectra consist of AB patterns at ca. 51 and 48 ppm ($^2J_{P-P}$~40 Hz) for (iii) and ca. 58 and 48 ppm ($^2J_{P-P}$=51 Hz) for (iv). The IR spectra of (iii) and (iv) proved valuable. The carbonyl ligand of (iii) absorbs at 2000 cm$^{-1}$. Complex (iv) has absorptions at 2151 and 2173 cm$^{-1}$ for the tBuNC and MeCN ligands.

Similarly, the enantiopure complex (v) is useful for asymmetric transfer hydrogenation of prochiral ketones and imines and is useful for the transfer hydrogenation of ketones and imines. Complex (v) has been crystallized as the BF$_4^-$ salt (see Example 7) and characterized by elemental analyses, NMR, IR, MS. The (S,S)-enantiomer of complex (v) has also been prepared and characterized including a single crystal X-ray diffraction study.

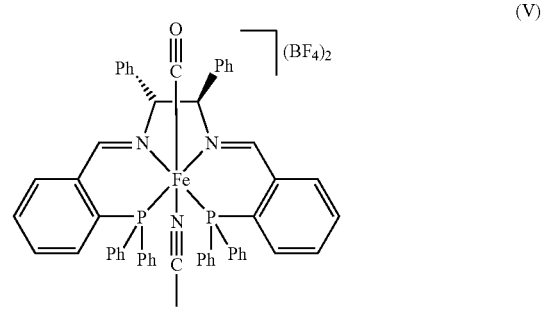

(v)

TABLE 4

Transfer hydrogenation of ketones from 2-propanol (6 mL) catalyzed by (v) and KOtBu (S/C/B = 600/1/8 unless specified) at 24° C. under N$_2$.[a]

| Entry | Substrate | Time (min) | Conv. (%) | e.e. (%) |
|---|---|---|---|---|
| 1 | Ph-CO-Me | 30 | 71 | 63 (S) |
| 2 | Ph-CO-Et | 30 | 75 | 70 (S) |
| 3 | Ph-CO-$^i$Pr | 30 | 58 | 94 (S) |
| 4 | Ph-CO-$^t$Bu[b] | 15 | 93 | 96 (S) |
| 5 | (2'-Cl—C$_6$H$_4$)—CO-Me | 30 | 93 | 29 (S) |
| 6 | (3'-Cl—C$_6$H$_4$)—CO-Me | 30 | 68 | 45 (S) |
| 7 | (4'-Cl—C$_6$H$_4$)—CO-Me | 30 | 81 | 38 (S) |
| 8 | 3-C$_{10}$H$_7$—CO-Me | 30 | 61 | 52 (S) |
| 9 | 2-C$_{10}$H$_7$—CO-Me | 30 | 73 | 61 (S) |
| 10 | Ph-(CH$_2$)$_2$—CO-Me | 15 | 91 | 57 (S) |
| 11 | Me-CO-$^i$Pr | 15 | 63 | 12 (S) |

[a] To a mixture of (v) (0.005 mmol) and KOtBu (0.04 mmol) was added a solution of ketone in 6 ml of iPrOH;
[b] S/C/B = 200/1/8

Other A groups of formula (I) can be envisaged such as the ferrocenyl substituent shown as part of compound 11.

The above complexes can be prepared using an efficient, economical, template synthesis utilizing air stable phosphinoaldehyde precursor. The synthesis of (I) is shown schematically as follows:

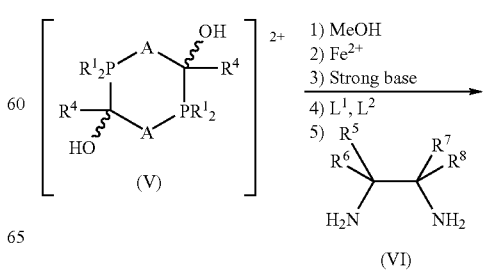

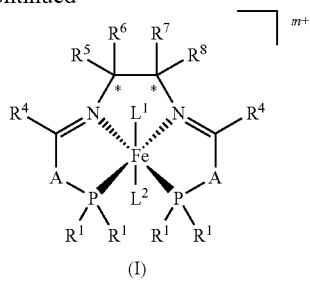

(I)

It is well known that in the process of hydrogenation or transfer hydrogenation, imine groups in the catalyst structure can be reduced to amine groups. These amine-containing catalysts, when they are soluble, are also active catalysts for the transfer hydrogenation of ketones under the same conditions as described for the imine catalysts described here.

In one embodiment, there is provided a process for the preparation of a hexa-coordinate iron (II) complex of formula (I), the process comprising reacting a phosphinaldehyde precursor of formula (V):

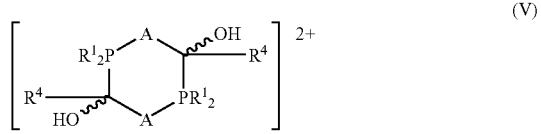

wherein each $R^1$ is independently selected from the group consisting of aryl, heteroaryl, $C_1$-$C_8$ alkyl, $C_2$-$C_8$ alkenyl, $C_1$-$C_8$ alkoxy, aryloxy, and cycloalkyl, all of which may be optionally substituted; two geminal $R^1$ groups may combine to form a $C_2$-$C_4$ linear alkyl diradical or $C_3$-$C_8$ branched alkyl diradical, each of which may be optionally substituted, to form a ring together with the phosphorus atom to which they are attached; or two $R^1$ groups, each of which is located on a different phosphorus atom, may combine to form a linker M, wherein M is selected from the group consisting of $C_2$-$C_4$ linear alkyl diradical and $C_3$-$C_8$ branched alkyl diradical, each of which may be optionally substituted, or M may be a diradical ligand with a wide bite angle;

A is

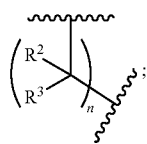

wherein each $R^2$ and $R^3$ are independently selected from the group consisting of H, substituted or unsubstituted $C_1$-$C_8$ alkyl, substituted or unsubstituted $C_2$-$C_8$ alkenyl, substituted or unsubstituted aryl, and substituted or unsubstituted cycloalkyl, and each n is an integer independently selected from 1, 2, and 3;

each $R^4$ is independently selected from the group consisting of H, substituted or unsubstituted $C_1$-$C_8$ alkyl, substituted or unsubstituted $C_2$-$C_8$ alkenyl, substituted or unsubstituted aryl, and substituted or unsubstituted cycloalkyl;

with a diamine of formula (VI):

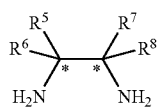

(VI)

wherein each $R^5$, $R^6$, $R^7$ and $R^8$ is independently selected from the group consisting of H, substituted or unsubstituted $C_1$-$C_8$ alkyl, substituted or unsubstituted $C_2$-$C_8$ alkenyl, substituted or unsubstituted aryl, and substituted or unsubstituted cycloalkyl; $R^5$ and $R^6$, together with the carbon atom to which they are attached, may combine to form a substituted or unsubstituted cycloalkyl ring of size from 5-8 carbons; $R^7$ and $R^8$, together with the carbon atom to which they are attached, may combine to form a substituted or unsubstituted cycloalkyl ring of size from 5-8 carbons; or $R^5$, $R^6$, $R^7$ and $R^8$, together with the carbon atoms to which they are attached, may combine to form a group selected from

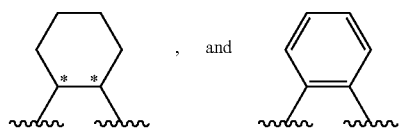 [SMILES: *C1CCCCC1* ; *c1ccccc1*]

each of which may be optionally substituted with one or more substituents selected from the group consisting of $C_1$-$C_8$ alkyl, $C_1$-$C_8$ alkoxy, and halogen atoms;
in the presence of:
an iron (II) salt;
a ligand selected from the group consisting of $CH_3CN$; pyridine and derivatives thereof; and imidazole and derivatives thereof; and
a strong base;
to form the compound of formula (I)

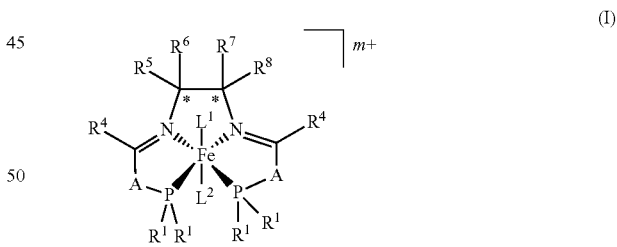

(I)

wherein A, $R^1$-$R^8$, and n are as defined above,
m is +2,
$L^1$ and $L^2$ are both $CH_3CN$; pyridine or a derivative thereof; or imidazole or a derivative thereof;
and adding at least one counter ion to counterbalance the charge of the compound of formula (I).

In one embodiment, the at least one counter ion is selected from $BF_4^-$; $PF_6^-$; $SbF_6^-$; $ClO_4^-$; $CH_3SO_3^-$; $CF_3SO_3^-$; $C_6H_5SO_3^-$; p-$CH_3C_6H_4SO_3^-$; $FeCl_4^{2-}$, $FeBr_4^{2-}$, $B(R^*)_4^-$, wherein $R^*$ is selected from phenyl, $C_6H_3(CF_3)_2$ and $C_6F_5$; halides; pseudohalides; $C_1$-$C_8$ alkoxides; and aryloxides. In another embodiment, the at least one counter ion is $BF_4^-$. In another embodiment, the at least one counter ion is $BPh_4^-$.

In another embodiment, the compound of formula (I), wherein $L^1$ and $L^2$ are both $CH_3CN$, pyridine or a derivative thereof, or imidazole or a derivative thereof, is further reacted with CO; hydride; halide ion; NCR, CNR or —OR, wherein R is independently selected from the group consisting of aryl, heteroaryl, $C_1$-$C_8$ alkyl, $C_2$-$C_8$ alkenyl and cycloalkyl, all of which may be optionally substituted; $R^a R^b R^c N$ wherein $R^a$, $R^b$, and $R^c$ are independently selected from the group consisting of H and $C_1$-$C_2$ alkyl; or $R^c(CO)R^d$ wherein $R^c$ and $R^d$ are independently selected from the group consisting of $C_1$-$C_8$ alkyl, aryl, and heteroaryl, to produce a compound of formula (VIIIa):

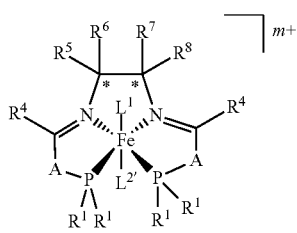

(VIIIa)

wherein A, $R^1$-$R^8$, and n are as defined for formula (I), $L_1$ is $CH_3CN$; pyridine or a derivative thereof; or imidazole or a derivative thereof; and $L^{2'}$ is selected from the group consisting of CO; hydride; halide ion; NCR, CNR or $^-$OR, wherein R is independently selected from the group consisting of aryl, heteroaryl, $C_1$-$C_8$ alkyl, $C_2$-$C_8$ alkenyl and cycloalkyl, all of which may be optionally substituted; $R^a R^b R^c N$ wherein $R^a$, $R^b$, and $R^c$ are independently selected from the group consisting of H and $C_1$-$C_2$ alkyl; or $R^c(CO)R^d$ wherein $R^c$ and $R^d$ are independently selected from the group consisting of $C_1$-$C_8$ alkyl, aryl, and heteroaryl, and m is +1 or +2.

In another embodiment, there is provided a process for the preparation of a hexa-coordinate iron (II) complex, the process comprising reacting a phosphinaldehyde precursor of formula (V):

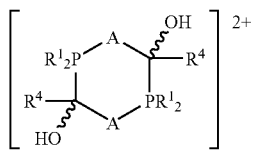

(V)

wherein each $R^1$ is independently selected from the group consisting of aryl, heteroaryl, $C_1$-$C_8$ alkyl, $C_2$-$C_8$ alkenyl, $C_1$-$C_8$ alkoxy, aryloxy, and cycloalkyl, all of which may be optionally substituted; two geminal $R^1$ groups may combine to form a $C_2$-$C_4$ linear alkyl diradical or $C_3$-$C_8$ branched alkyl diradical, each of which may be optionally substituted, to form a ring together with the phosphorus atom to which they are attached; or two $R^1$ groups, each of which is located on a different phosphorus atom, may combine to form a linker M, wherein M is selected from the group consisting of $C_2$-$C_4$ linear alkyl diradical and $C_3$-$C_8$ branched alkyl diradical, each of which may be optionally substituted, or M may be a diradical ligand with a wide bite angle;

A is

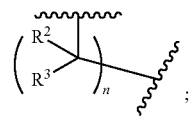

wherein each $R^2$ and $R^3$ are independently selected from the group consisting of H, substituted or unsubstituted $C_1$-$C_8$ alkyl, substituted or unsubstituted $C_2$-$C_8$ alkenyl, substituted or unsubstituted aryl, and substituted or unsubstituted cycloalkyl, and each n is an integer independently selected from 1, 2, and 3;

each $R^4$ is independently selected from the group consisting of H, substituted or unsubstituted $C_1$-$C_8$ alkyl, substituted or unsubstituted $C_2$-$C_8$ alkenyl, substituted or unsubstituted aryl, and substituted or unsubstituted cycloalkyl;

with a diamine of formula (VI):

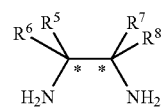

(VI)

wherein each $R^5$, $R^6$, $R^7$ and $R^8$ is independently selected from the group consisting of H, substituted or unsubstituted $C_1$-$C_8$ alkyl, substituted or unsubstituted $C_2$-$C_8$ alkenyl, substituted or unsubstituted aryl, and substituted or unsubstituted cycloalkyl; $R^5$ and $R^6$, together with the carbon atom to which they are attached, may combine to form a substituted or unsubstituted cycloalkyl ring of size from 5-8 carbons; $R^7$ and $R^8$, together with the carbon atom to which they are attached, may combine to form a substituted or unsubstituted cycloalkyl ring of size from 5-8 carbons; or $R^5$, $R^6$, $R^7$ and $R^8$, together with the carbon atoms to which they are attached, may combine to form a group selected from

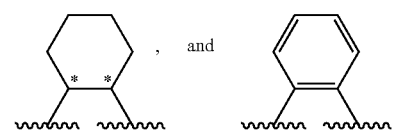 [SMILES: *C1CCCCC1* ; *c1ccccc1*]

each of which may be optionally substituted with one or more substituents selected from the group consisting of $C_1$-$C_8$ alkyl, $C_1$-$C_8$ alkoxy, and halogen atoms;

in the presence of:

an iron (II) salt;

a ligand selected from the group consisting of $CH_3CN$; pyridine and derivatives thereof; and imidazole and derivatives thereof; and a strong base;

and further reacting the reaction product of the foregoing steps with CO to produce a compound of formula (VIIIa):

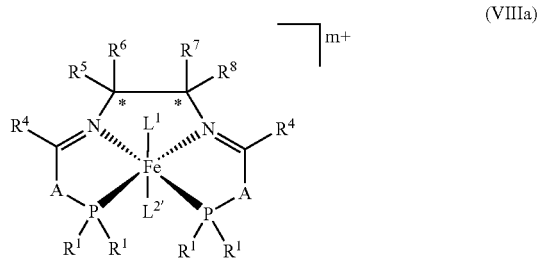

(VIIIa)

wherein A, $R^1$-$R^8$, and n are as defined above, $L_1$ is CO, $L^{2'}$ is Br, and m is +1;

and adding a counter ion to counterbalance the charge of the compound of formula (VIIIa).

The synthesis is conducted in an atmosphere of $N_2$ (1 atm) or Ar (1 atm) or another suitable gas to prevent reaction with atmospheric oxygen.

The concentration of the dimer V for use in forming the complexes disclosed herein can range from 0.5 M to 0.0005 M with a preferred concentration of 0.03M. The concentration of the diamine for use in forming the complexes disclosed herein can range from 0.5 M to 0.0005 M with a preferred concentration of 0.03M.

Suitable iron (II) salts for use in forming the complexes disclosed herein include $[Fe(H_2O)_6]^{2+}$ with counterions as noted herein, namely, $Fe(BF_4)_2$; $Fe(PF_6)_2$; $Fe(SbF_6)_2$; $Fe(ClO_4)_2$; $Fe(MeSO_3)_2$; $Fe(CF_3SO_3)_2$; $Fe(C_6H_5SO_3)_2$; $Fe(p-CH_3C_6H_4SO_3)_2$; $FeCl_4^{2-}$; $FeBr_4^{2-}$; $Fe[B(R^*)_4]_2$, wherein $R^*$ is selected from phenyl, $C_6H_3(CF_3)_2$ and $C_6F_5$; $FeX_2$ wherein X is a halide or pseudohalide; $Fe[O(C_1-C_8\ alkyl)]_2$; $FeSO_4$; $Fe(NO_3)_2$; and $Fe[R^{}C(O)O]_2$, wherein $R^{}$ is $C_1-C_3$ alkyl, $CF_3$, or phenyl, and hydrates thereof. The preferred range of iron concentrations for the template synthesis of complex II is 1 M to 0.001 M with a preferred concentration of 0.05 M Suitable strong bases for use in forming the complexes disclosed herein include alkoxides, such as NaOMe, DBU, a phosphazene, or an alkaline or alkaline-earth metal carbonate salt, carboxylate salt, alkoxide salt or hydroxide salt. In one embodiment, the strong base may be MOR*, wherein M is an alkaline metal selected from Na and K, and R* is $C_1-C_4$ alkyl. The preferred base to iron ratio is 1.3:1.

Suitable solvents for forming the complexes disclosed herein include MeOH, EtOH, PrOH, iPrOH, BuOH, $CH_3CN$, EtCN, pyridine, picoline, imidazole, methylimidazole. The preferred solvents are alcoholic solvents, such as MeOH. The preferred total volume of the solvent in the synthesis ranges from 1 mL to 20,000 mL with a preferred volume of 10 mL.

The temperature for the template synthesis can range between 0° and 120° C. with the preferred temperature being between 20° C. and 40° C.

The catalysts disclosed herein comprising a compound of formula (I) and with $L^1=L^2$=MeCN are surprisingly active and selective for the hydrogenation, by use of hydrogen gas, of ketones to produce valuable chiral and non-chiral alcohols in the presence of a base and an appropriate solvent. The use of complex (i) provides a particularly active and usefully enantioselective catalyst system.

The hydrogenation reaction involving a catalyst disclosed herein may or may not require solvent. When the use of the solvent is preferred for practical reasons, any solvent can be utilized for better performance of the catalyst. Non-limiting examples include primary, secondary and tertiary alcohols with hydrocarbon skeleton containing 2-15 carbons or aromatic solvents or ethers or hydrocarbon solvents.

In the solvent, the catalyst can be used at concentrations of 0.001 mM to 0.1 mM while the substrate ketone or imine can be used in concentrations of 2 mM to 10 M. The pressure of hydrogen gas can range from 0.5 atm to 100 atm with a preferred pressure of 10 atm. Preferred concentrations of catalyst and substrate are 0.8 mM and 0.16 M, respectively, with a ketone to catalyst ratio of 200:1.

In another embodiment, the phosphinaldehyde precursor is:

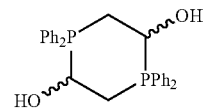

the diamine is:

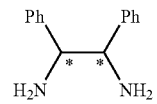

and the product is a compound of formula (I) having the structure:

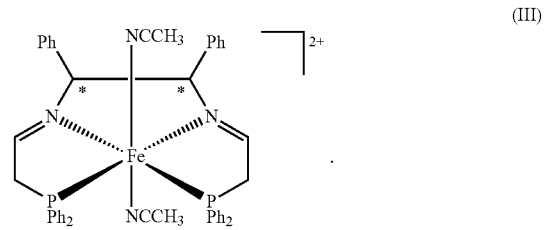

(III)

In one embodiment, the chiral carbon atoms denoted by asterisks in (III) above both have an R configuration. In another embodiment, these chiral carbon atoms both have an S configuration.

The processes outlined herein generates a catalyst with sections derived from the precursor diamine (VI) and phosphine (V) precursor building blocks with the iron ion acting as a template to orient the precursors to ensure a high yield of the compound of formula (I). The sections are shown in structure (VII) below:

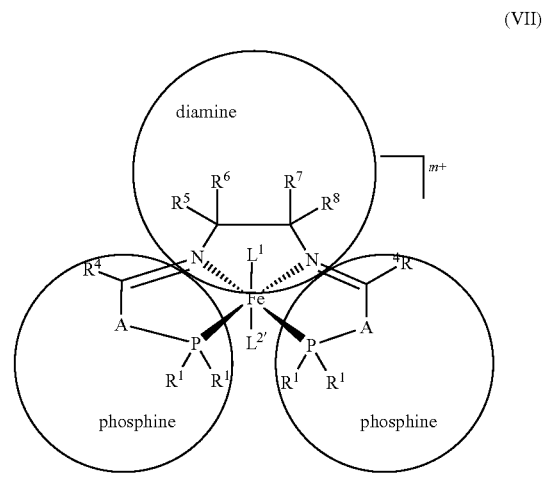

(VII)

This is an advantage since catalysts can be rapidly synthesized from a phosphine precursor and a diamine precursor with a variety of substitutents, providing flexibility to appropriately optimize manufacturing costs and end product quality specifications, such as a high enantiomeric excess. The methods disclosed herein allow for tuning of the coordinating ligand to obtain the easy introduction of chiral elements such as enantiomerically pure diamines into the catalyst because of the modular nature of the coordinating ligand. As a consequence, the iron (II) complex with PNNP ligand is easily modified by introducing substituents to produce a catalyst structure capable of interaction with a substrate and ensuring selectivity. Where both enantiomers of these diamines are available, both enantiomers of an iron catalyst can be easily prepared to hydrogenate a substrate to either enantiomer of the target molecule.

The phosphine-aldehyde precursors (V) are prepared by methods known in the art from commercially available or readily prepared phosphine starting materials $PHR^1_2$ or $PClR^1_2$ and compounds $XCR^2R^3Y$ where X is a halide or tosylate or other good leaving group known in the art and Y is a formyl group —CHO or a protected formyl group —CH(OR)$_2$. In addition, a new method for the synthesis of phosphine-aldehyde precursors of formula (XIII) is outlined below. The diamines $NH_2CR^5R^6CR^7R^8NH_2$ are available from commercial sources.

A most interesting catalyst has the discrete structure (i), shown above (also see Example 1). The chiral ligand can have an (R,R) or (S,S) configuration. To counterbalance the 2+ charge in the metal complex salt, anions such as $BF_4^-$, $PF_6^-$, $SbF_6^-$, $FeCl_4^{2-}$, $FeBr_4^{2-}$, tetraarylborates where the aryl is Ph, $C_6H_3(CF_3)_2$ or $C_6F_5$, or halides or pseudohalides or alkoxides and others noted above may be used.

Catalysts of structure (i), for example the tetraphenylborate salt, are prepared in a similar fashion to that of other iron complexes reported by Mikhailine et al. (Mikhailine et al. "Template Syntheses of Iron(II) Complexes Containing Chiral P—N—N—P and P—N—N Ligands," *Inorg. Chem.* 47 (2008), pp 6587-6589) by the template reaction of the phosphonium salt shown below with (R,R)-dpen as described in Example 1: (S,S)-dpen can alternatively be used to generate the other enantiomer of (i).

The complexes are precipitated as the $BPh_4^-$ salts in high yield and characterized by NMR, electrospray ionization mass spectrometry, and elemental analysis. The detailed procedure of the complex (i) preparation is described as Example 1.

The reaction of complex I where $L^1=L^2$=acetonitrile or another nitrogen donor ligand such as imidazole or pyridine with carbon monoxide yields the monocarbonyl catalysts of formula (VIII).

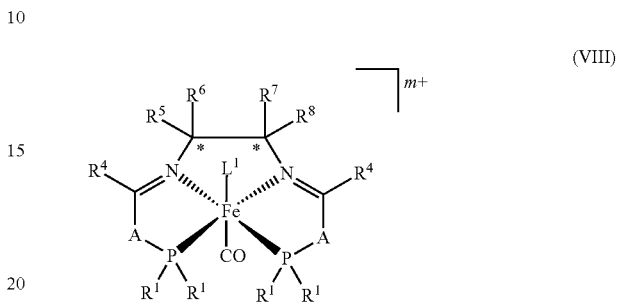

(VIII)

For example when complex (i) in acetone is treated with 5 atm CO, the monocarbonyl complex (ii) is formed (see Example 2). When the complex trans-[Fe(NCMe)$_2$(9)](BF$_4$)$_2$ (Sui-Seng et al., "Highly Efficient Catalyst Systems Using Iron Complexes with a Tetradentate PNNP Ligand for the Asymmetric Hydrogenation of Polar Bonds." *Angew. Chem. Int. Ed. Engl.* 47 (2008), pp. 940-943) in acetone is reacted with 1 atm CO, the carbonyl complex trans-[Fe(NCMe)(CO)(9)](BF$_4$)$_2$ (iii) is formed (see Example 4). Similarly when [Fe(NCMe)$_2$(9)](BF$_4$)$_2$ in acetone is reacted with tertiary-butylisocyanide, the complex [Fe(NCMe)(CN$^t$Bu)(9)](BF$_4$)$_2$ (iv) is formed (see Example 5). The reaction of complex (vi) (Mikhailine et al. "Template Syntheses of Iron(II) Complexes Containing Chiral P—N—N—P and P—N—N Ligands," *Inorg. Chem.* 47 (2008), pp 6587-6589) (Example 8) with CO produces the complex (vii; Example 9).

Scheme 3

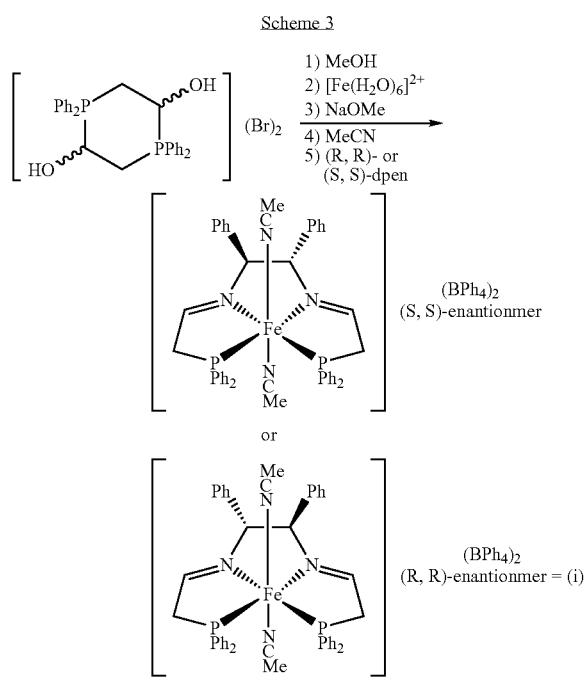

Scheme 4

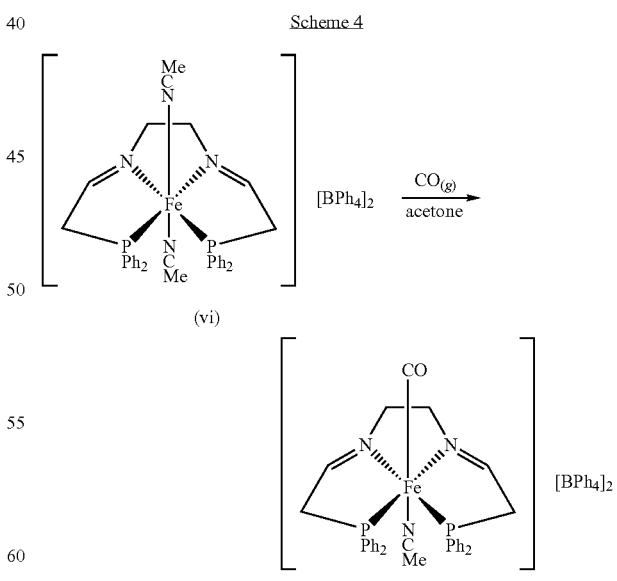

If the compound of formula (I) is reacted with carbon monoxide prior to the addition of a counterion and isolation of the iron (II) complex, this yields the compounds of formula (VIIIa)

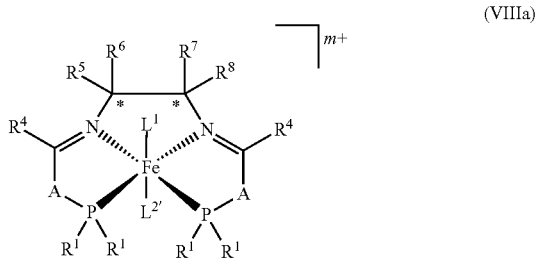

(VIIIa)

wherein A, $R^1$-$R^8$, and n are as defined for formula (I), $L_1$ is CO, $L^{2'}$ is Br, and m is +1. A counter ion is then added to counterbalance the charge of the compound of formula (VIIIa). These iron (II) complexes have been found to be catalytically active.

Complex vi has less than optimum activity (<5% conversion) for the hydrogenation of acetophenone at 35° C., 25 atm $H_2$ with KOtBu in iPrOH, and is inactive for the transfer hydrogenation of ketones in basic isopropanol.

Catalyst (vii) can be used for transfer hydrogenation. In the $N_2$ glovebox, the iron complex (vii) (8.7 mg, 0.007 mmol), KO$^t$Bu (6.3 mg, 0.056 mmol) and acetophenone (168 mg, 1.4 mmol) were separately dissolved in the 3 mL of 2-propanol, each. The resulting solutions were added to a vial charged with a stirring bar in the order: substrate, catalyst followed by base and stirred at room temperature. The samples of the reaction mixture were analyzed by GC. The conversion was 92% after 75 minutes.

Complex trans-[Fe(MeCN)$_2$(6)](BF$_4$)$_2$ (Example 10) wherein 6 is

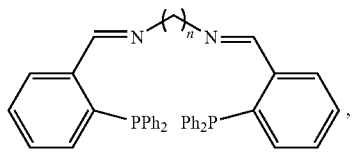

n=2, was prepared and tested. For the hydrogenation of acetophenone with $H_2$ (25 atm) with a catalyst to base to substrate ratio of 1:15:225 in isopropanol the conversion was 4% after 18 h. It was found to be inactive for the transfer hydrogenation of acetophenone in basic isopropanol under the standard conditions.

The iron (II) complex trans-[Fe(MeCN)$_2$(6)](BF$_4$)$_2$, can be reacted with CO to produce

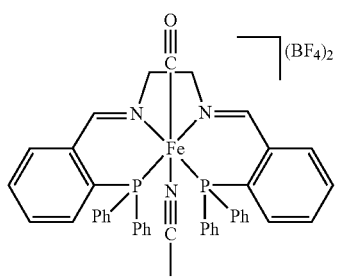

(viii)

(Example 11).

Catalyst (viii) can be used for transfer hydrogenation. To a mixture of (viii) (0.005 mmol) and KOtBu (0.04 mmol) was added a solution of ketone in 6 ml of iPrOH. Catalyst (viii) was found to be highly active for the transformation of acetophenone to 1-phenylethanol at room temperature using a catalyst:base:substrate ratio of 1:8:600 (85% conversion after 60 min).

The bis-acetonitrile complexes trans-[Fe(NCMe)$_2${9}][BF$_4$]$_2$, trans-[Fe(MeCN)$_2$(6)](BF$_4$)$_2$, wherein 6 is

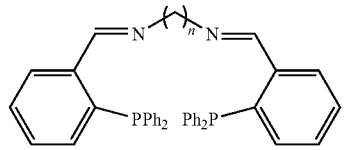

where n=2 and trans-[Fe(NCMe)$_2${(R,R)—PPh$_2$C$_6$H$_4$CHNCHPhCHPhNCHC$_6$H$_4$PPh$_2$}][BF$_4$]$_2$ were prepared by reaction of the known PNNP ligands 6 (Jeffery, J. C.; Rauchfuss, T. B.; Tucker, P. A. *Inorg. Chem.* 1980, 19, 3306-3316) 9, and PPh$_2$C$_6$H$_4$CHNCHPhCHPhNCHC$_6$H$_4$PPh$_2$ (J.-X. Gao et al. *Chirality* 2000, 12, 383) with iron salts such as [Fe(OH$_2$)$_6$](BF$_4$)$_2$ in acetonitrile as described in the examples below.

The iron complexes trans-[Fe(NCMe)(CO)(6)][BF$_4$], (R,R)- or (S,S)-trans-[Fe(NCMe)(CO){9}][BF$_4$]$_2$ and (R,R)- or (S,S)-trans-[Fe(NCMe)(CO)(PPh$_2$C$_6$H$_4$CHNCHPhCHPhNCHC$_6$H$_4$PPh$_2$)][BF$_4$]$_2$ were obtained as orange solids in good yields when the corresponding bis-acetonitrile compounds just mentioned were stirred under a CO atmosphere in acetone. The new compounds are fairly air stable, both as a solid and in solution. They are soluble in acetonitrile and methylenechloride, poorly soluble in acetone, chloroform, 2-propanol and insoluble in tetrahydrofuran, ether and hydrocarbons. The new compounds were characterized by $^1$H and $^{13}$C and $^{31}$P NMR techniques, elemental analysis, mass spectroscopy, IR and the solid state structures were confirmed by X-ray crystallography. The $^{31}$P{$^1$H} NMR spectrum of trans-[Fe(NCMe)(CO)(6)][BF$_4$]$_2$ shows a singlet while those for (R,R)- or (S,S)-trans-[Fe(NCMe)(CO){9}][BF$_4$]$_2$ and (R,R)- or (S,S)-trans-[Fe(NCMe)(CO)(PPh$_2$C$_6$H$_4$CHNCHPhCHPhNCHC$_6$H$_4$PPh$_2$)][BF$_4$]$_2$ show two doublets. Mass spectra (ESI) show the cationic fragment without the acetonitrile and carbonyl ligands.

In one embodiment, there is provided a process for preparing an alcoholic compound wherein said process comprises a step of preparing the alcoholic compound by reducing a ketone or aldehyde with the reaction of hydrogen or a compound donating hydrogen in the presence of a hexa-coordinate iron (II) complex of formula (I), with the proviso that the ketone is not an unsubstituted cycloalkanone.

As can be seen from Table 3, no conversion was observed for the transfer hydrogenation of cyclohexanone catalyzed by (iii). However, it is envisioned that cyclic ketones having substituents such as aromatic groups may be better substrates.

In another embodiment, the hexa-coordinate iron (II) complex comprises a compound of formula (I) having the structure:

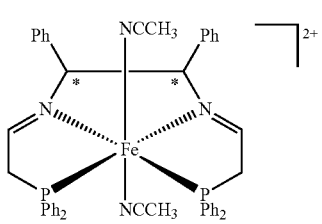

(III)

In another embodiment, the chiral carbons atoms denoted by asterisks both have an R configuration. In another embodiment, the chiral carbons atoms denoted by asterisks both have an S configuration, In another embodiment, the reaction uses hydrogen.

In yet another embodiment, the substrate is a ketone. In another embodiment, the ketone is an aromatic ketone. In yet another embodiment, the ketone is prochiral.

In another embodiment, there is provided a process for preparing an amine compound wherein said process comprises a step of preparing the amine compound by reducing an imine with the reaction of hydrogen or a compound donating hydrogen in the presence of a hexa-coordinate iron (II) complex of formula (I). In another embodiment, the hexa-coordinate iron (II) complex comprises a compound of formula (I) having the structure:

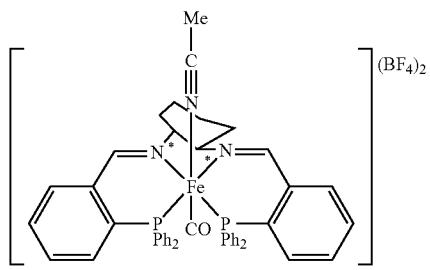

In another embodiment, the chiral carbons atoms denoted by asterisks both have an R configuration. In another embodiment, the chiral carbons atoms denoted by asterisks both have an S configuration. In another embodiment, the reaction uses a compound donating hydrogen. In another embodiment, the imine is not prochiral.

The catalysts I disclosed herein can reduce aldehydes, ketones and imines with general structure (IX):

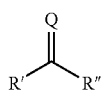

(IX)

where the R', R" symbols, taken separately, represent simultaneously or independently a hydrogen atom, a linear or branched alkyl or alkenyl chain containing 1-8 carbon atoms, possibly substituted, a cycloalkyl radical or an aryl group, possibly substituted. The symbol Q represents simultaneously or independently an oxygen atom or NR''' group, where R''' symbol represent simultaneously or independently a hydrogen atom, a linear or branched alkyl or alkenyl chain containing 1-8 carbon atoms, possibly substituted, a cycloalkyl radical or an aryl group, possibly substituted. Possible substituents include alkyl groups (such as $C_1$-$C_8$ alkyl), aryl groups, halogens, and alkoxy groups.

The reduction of ketones and imines with general structure (IX) produce products, namely alcohols and amines, respectively with general structure (X). When the correct asymmetric hydrogenation or transfer hydrogenation catalyst I is applied, the products are obtained in one enantiomeric form. For example the use of complex (i) in asymmetric hydrogenation gives the S-alcohol in high e.e. while the use of complex (ii) or (v) in asymmetric transfer hydrogenation gives the S-alcohol in high e.e. The correct catalyst I might also be used for other catalytic asymmetric reactions such as the transfer of hydrogen from a hydrogen donor such as isopropanol or ethanol to a ketone or imine. The use of the catalysts disclosed herein for addition of a hydrosilane to a ketone or imine, an asymmetric Michael addition of donor to an acceptor, an asymmetric Diels-Alder reaction of an olefin to a diene or an asymmetric cyclopropanation reaction may also be possible.

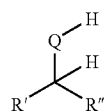

(X)

The catalysts disclosed herein comprising a compound of formula (I) and with $L^1$=$L^2$=MeCN are surprisingly active and selective for the hydrogenation, by use of hydrogen gas, of ketones to produce valuable chiral and non-chiral alcohols in the presence of a base and an appropriate solvent. The use of complex (i) provides a particularly active and usefully enantioselective catalyst system.

The hydrogenation reaction involving a catalyst disclosed herein may or may not require solvent. When the use of the solvent is preferred for practical reasons, any solvent can be utilized for better performance of the catalyst. Non-limiting examples include primary, secondary and tertiary alcohols with hydrocarbon skeleton containing 2-15 carbons or aromatic solvents or ethers or hydrocarbon solvents.

In the solvent, the catalyst can be used at concentrations of 0.001 mM to 0.1 mM while the substrate ketone or imine can be used in concentrations of 2 mM to 10 M. The pressure of hydrogen gas can range from 0.5 atm to 100 atm with a preferred pressure of 10 atm. Preferred concentrations of catalyst and substrate are 0.8 mM and 0.16 M, respectively, with a ketone to catalyst ratio of 200:1.

The base in the hydrogenation process using $H_2$ gas can be substrate (if it has a basic functionality) or a strong neutral base such as DBU or a phosphazene, or an alkaline or alkaline-earth metal carbonate salt, carboxylate salt, alkoxide salt or hydroxide salt. The base in the process can be used in a concentration of between one and fifty times the concentration of the catalyst concentration. The preferred base to catalyst ratio is 15.

The temperature of the direct hydrogenation with hydrogen gas catalyzed by complexes comprising a compound of formula (I) and with $L^1$=$L^2$=MeCN can range between 0° and 120° C. with the preferred temperature being 35° C.

Catalysts such as (ii) are particularly active and selective for the asymmetric transfer hydrogenation of ketones to non racemic alcohols in basic isopropanol solvent or other alcohols or mixtures such as formic acid/triethylamine known in the art to transfer hydrogen. Similarly, complexes (iii), (iv) and (v) can also be used as catalysts for the asymmetric transfer hydrogenation of ketones and the transfer hydrogenation of certain imines. The catalysts (VIII) with the ligand $L^1$=MeCN or another nitrile donor ligand and $L^2$=CO are surprisingly active and selective for the reduction of ketones to non-racemic alcohols by transfer of hydrogen from basic isopropanol or other alcohols or mixtures such as formic acid/triethylamine known in the art to transfer hydrogen.

The conditions for the transfer hydrogenation catalyzed by catalysts (ii), (iii), (iv), (v) and of the type (VIII) are surprising mild. The preferred temperature is room temperature but a range of temperatures is possible from 0° and 150° C. The turnover numbers reported in the examples are unprecedented for non-PGM catalysts that operate at room temperature.

The transfer hydrogenation catalysts (ii), (iii), (iv), (v) and of the type (VIII) can be used at concentrations of 0.001 mM to 1 mM while the substrate ketone or imine can be used in concentrations of 2 mM to 5 M. Preferred concentrations of catalyst and substrate are 0.1 mM and 0.2 M, respectively, with a ketone to catalyst ratio of 1600:1 for catalyst (ii) and 200:1 for catalyst (iii) and 600:1 for catalyst (v) or in general a substrate to catalyst ratio of 500:1.

The base in the transfer hydrogenation process can be substrate (if it has a basic functionality) or a strong neutral base such as DBU or a phosphazene, or an alkaline or alkaline-earth metal carbonate salt, carboxylate salt, alkoxide salt or hydroxide salt. The base in the process can be used in a concentration of between one and fifty times the concentration of the catalyst concentration. The preferred base to catalyst ratio is 8.

A new method of synthesizing phosphonium dimers has been developed. It has been found that such phosphonium dimers can be synthesized by the direct reaction of an alkyl-substituted secondary phosphine with organic compounds containing both a protected aldehyde and a carbon-halogen bond according to the general reaction scheme shown below.

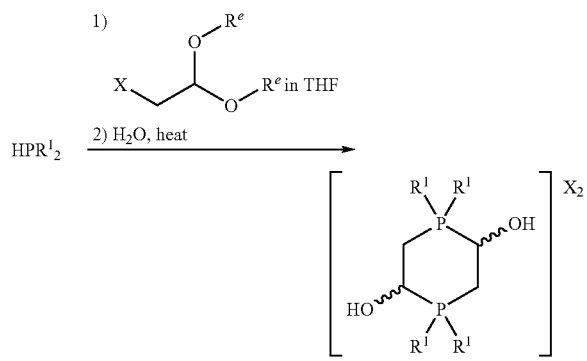

A process for preparing a phosphonium dimer of formula (XIII) is provided:

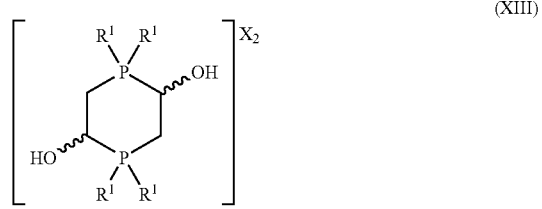

(XIII)

wherein $R^1$ is selected from the group consisting of $C_1$-$C_8$ alkyl, $C_1$-$C_8$ substituted alkyl, cycloalkyl, and substituted cycloalkyl, and X is selected from the group consisting of Br and I, the process comprising:
reacting a compound of formula (XI):

$HPR^1_2$ (XI)

wherein $R^1$ is as defined above;
with a compound of formula (XII):

(XII)

wherein X is as defined above, and $R^e$ is $C_1$-$C_8$ alkyl, or the two Re can combine to form a $C_2$-$C_3$ linear alkyl diradical; and heating the reaction product in the presence of water to form the phosphonium dimer of formula (XIII)

$R^1$ is an electron-donating alkyl substituent, and in one embodiment the two $R^1$ groups on each phosphorus atom may be different. $R^e$ may be, for example, Me, Et, Pr etc. or $(R^e)_2$=—$CH_2CH_2$—.

Cyclic phosphonium dimers V with A=$CH_2$ and $R^4$=H and with $R^1$=cyclohexyl (Example 15) isopropyl (Example 21) or ethyl (Example 22) substituents at the phosphorus atoms were prepared in a new, direct reaction of the secondary phosphine with the protected bromoacetoaldehyde diethyl acetal ($BrCH_2CH(OEt)_2$) in THF, neat or in other organic solvents that dissolve the compounds to give an intermediate phosphonium salt that was then hydrolyzed. The yields of the white solids are 80, 81 and 40%, respectively. The cyclohexyl and isopropyl compounds are air- and moisture-stable white solids that are soluble in methanol or/and water and insoluble in other common organic solvents. They possess similar physical properties to that of the dimer with phenyl groups on phosphorus. The dimer with ethyl groups, on the other hand, adsorbs water on prolonged exposure to atmosphere, and is soluble only in water. However an aqueous solution of this compound is stable toward oxidation by molecular oxygen.

The new dimers were fully characterized by NMR spectroscopy and X-ray diffraction experiments. These compound show two characteristic singlets in the $^{31}P\{^1H\}$ NMR spectra in the region between 11 and 40 ppm and a multiplet in the region between 5.3 and 6.2 ppm for the proton on the carbon with the hydroxyl group —CH(OH)—, a downfield shift of the aldehyde hydrogen resonance which is expected in the 9-10 ppm region. The two singlets observed in the $^{31}P\{^1H\}$ NMR arise from the rac and meso diastereomers.

The invention will now be described in further detail by way of the following examples, wherein the temperatures are indicated in degrees centigrade and the abbreviations have the usual meaning in the art.

EXAMPLES

General Considerations

All preparations and manipulations were carried out under an argon or nitrogen atmosphere using standard Schlenk, vacuum-line, and glove-box techniques. Dry, oxygen-free solvents were prepared by distillation from appropriate drying agents and employed throughout. The synthesis of the ligands (R,R)-cyP$_2$N$_2$ (9) and (R,R)—PPh$_2$C$_6$H$_4$CHNCHPhCHPhNCHC$_6$H$_4$PPh$_2$ have been reported previously (J.-X. Gao, H. Zhang, X.-D. Yi, P.-P. Xu, C.-L. Tang, H.-L. Wan, K.-R. Tsai, T. Ikariya, *Chirality* 2000, 12, 383). All other reagents used in the experiments were obtained from commercial sources and used as received. The mass spectroscopy (ESI+, MeOH) and elemental analyses were performed at the University of Toronto, on sample handled under argon for the EA. Varian Gemini 400 MHz and 300 MHz spectrometers were employed for recording $^1$H (400 MHz and 300 MHz), $^{13}$C{$^1$H} (100 MHz and 75 MHz), and $^{31}$P{1H} (161 MHz and 121 MHz) NMR spectra at ambient temperature. The $^1$H and $^{13}$C NMR spectra were referenced to solvent resonances, as follows: 7.26 and 77.16 ppm for CHCl$_3$ and CDCl$_3$, 1.94 and 1.24 ppm for CH$_3$CN and CD$_3$CN). The $_{31}$P NMR spectra were referenced to 85% H$_3$PO$_4$ (0 ppm). All infrared spectra were recorded on a Nicolet 550 Magna-IR spectrometer.

The samples of hydrogenation reaction mixtures were analyzed by $^1$H NMR spectroscopy and GC using a Perkin Elmer Autosystem XL chromatograph with a chiral column (CP chirasil-Dex CB 25 m×2.5 mm). Hydrogen was used as a mobile phase at a column pressure of 6 psi. The injector temperature was 250° C., and a FID temperature was 275° C. The retention times of the substrates are listed in Table 5.

trans-4-phenyl-3-buten-2-one: the GC analysis were conducted as above, except that for the GC conditions the oven temperature was 140° C. The retention times were trans-4-phenyl-3-buten-2-one 7.8 min, I-4-phenyl-2-butanol 11.1 min, (S)-4-phenyl-2-butanol 11.4 min, trans-4-phenyl-3-buten-2-one 13.4 min, trans-(R)-4-phenyl-3-buten-2-ol 15.9 min, trans-(S)-4-phenyl-3-buten-2-ol 16.2 min. The product was also identified by 1H NMR spectroscopy and the data obtained matches literature values.

N-Benzylideneaniline and benzophenone: the conversion of the product was determined by 1H NMR spectroscopy and the data matches those of the commercial samples.

General procedure for the iron catalyzed H$_2$-hydrogenation of polar bonds: In an Ar or N$_2$ glovebox, the iron complex (8 mg, 0.008 mmol) was suspended in 2 mL of 2-propanol and acetophenone (225 equiv) in 1 mL of 2-propanol. The solution of base was prepared by dissolution of KOtBu (15 equiv) in 2 mL of 2-propanol. The solution containing the substrate and then the one with base, followed by the suspension of catalyst were injected into a 50 cm$^3$ Parr hydrogenator reactor filled with hydrogen at the desired pressure and temperature, maintained by use of a Fischer Scientific Isotemp 1016D water bath.

The procedures for the iron catalyzed transfer hydrogenation of polar bonds are found in the footnotes of the Tables above.

TABLE 5

GC analytical data for the reduced substrates (t$_s$ = retention time of substrate; t$_1$, t$_2$ = retention times of the products)

| Substrate | Oven Temp. (° C.) | t$_s$ (min) | t$_1$ (min) | t$_2$ (min) |
|---|---|---|---|---|
| Ph-CO-Me | 130 | 5.0 | 8.5 | 9.1 |
| (2'-Cl—C$_6$H$_4$)—CO-Me | 145 | 4.7 | 10.0 | 11.7 |
| (3'-Cl—C$_6$H$_4$)—CO-Me | 130 | 7.8 | 16.6 | 17.7 |
| (4'-Cl—C$_6$H$_4$)—CO-Me | 145 | 5.9 | 11.1 | 12.0 |
| (4'-Br—C$_6$H$_4$)—CO-Me | 155 | 6.5 | 11.4 | 12.1 |
| (4'-Me-C$_6$H$_4$)—CO-Me | 125 | 6.5 | 9.6 | 10.4 |
| (4'-OMe-C$_6$H$_4$)—CO-Me | 130 | 15.6 | 21.8 | 23.2 |
| Ph-CO-Et | 105 | 18.4 | 48.5 | 51.5 |
| C$_{10}$H$_7$—CO-Me[a] | 150 | 21.8 | 35.7 | 37.5 |
| C$_{10}$H$_7$—CO-Me[b] | 140 | 24.1 | 63.6 | 73.9 |
| Ph-CHO | 130 | 3.9 | 5.9 | — |
| Ph-CO-iPr | 114 | 11.0 | 37.2 | 37.8 |

TABLE 5-continued

GC analytical data for the reduced substrates (t$_s$ = retention time of substrate; t$_1$, t$_2$ = retention times of the products)

| Substrate | Oven Temp. (° C.) | t$_s$ (min) | t$_1$ (min) | t$_2$ (min) |
|---|---|---|---|---|
| Ph-CH$_2$—CH$_2$—CO-Me | 135 | 7.9 | 11.8 | 12.6 |
| Ph-CO-tBu | 140 | 5.9 | 11.6 | 12.2 |
| CH$_3$—CO—CH—(CH$_3$)$_2$ | 60 | 2.9 | 8.2 | 8.5 |

[a]2-acetonaphthone.
[b]1-acetonaphthone

Example 1

Preparation of the Catalyst (R,R)—[Fe(Ph$_2$PCH$_2$CH=NCH(Ph)CH(Ph)N=CHCH$_2$PPh$_2$)(CH$_3$CN)$_2$][BPh$_4$]$_2$, (i)

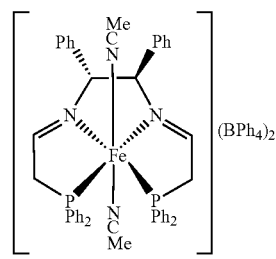

Synthesis of the diphenylphosphino-acetaldehyde hydrobromide Dimer

The procedure for the synthesis of the diphenylphosphino-acetaldehyde hydrobromide dimer has been previously reported by Matt et al. (Matt, D.; Ziessel, R.; De Cian, A.; Fischer, J. New J. Chem. 1996, 20, 1257-1263) and was used in this study with modifications. Potassium hydride (413 mg, 10.3 mmol) was partially dissolved in 10 mL of dry THF. Diphenylphosphine (1.60 g, 8.58 mmol) was added to the resulting mixture to give a purple solution. After 30 min the solution was cooled to −78° C. and bromoacetaldehyde diethyl acetal (1.691 g, 8.58 mmol) was added over the course of 15 min. The mixture was brought to room temperature to give a yellow solution. A diluted hydrobromic acid (10 mL, 1.17 mol_L−1) were added and the mixture was heated at 40° C. overnight. The solvent volume was reduced by one half. The white precipitate was recovered by filtration and washed with 20 mL of water and 20 mL cyclohexane:ethyl acetate (1:1 by volume). Drying in vacuo yielded 4 (2.51 g, 4.06 mmol) as a white powder. Analytical data were the same as those that have been reported by Matt et al.

Synthesis of the Catalyst (R,R)—[Fe(Ph$_2$PCH$_2$CH=NCH(Ph)CH(Ph)N=CHCH$_2$PPh$_2$)(CH$_3$CN)$_2$][BPh$_4$]$_2$, (i)

The diphenylphosphino-acetaldehyde hydrobromide dimer (200 mg, 0.324 mmol) was completely dissolved in MeOH (6 mL). [Fe(H$_2$O)$_6$][BF$_4$]$_2$ (164 mg, 0.485 mmol) was added to the reaction mixture. NaOMe (34.9 mg, 0.647 mmol) was added as a MeOH (1 mL) solution and the color of the solution changed from colorless to clear yellow. After 10 min of stirring, 1 mL of acetonitrile was added. To this solution was added, over the course of 20 min, a solution of (1R,2R)-(+)-1,2-diphenylethylenediamine (R,R-dpen, 69 mg, 0.323 mmol) in 0.5 mL of acetonitrile. The solution changed color to purple after the addition. After 20 h the resulting solution was added to a solution of NaBPh$_4$ (250 mg, 0.658 mmol) in 1 mL of MeOH to cause the formation of the precipitate. A pink solid was recovered by filtration and dried under vacuum. Yield of (i): 83% (380 mg); $^1$H NMR (400 MHz, CD$_3$CN) δ: 1.54 (s, 6H, CH$_3$CN), 3.95-4.15 (m, 2H, HCP), 4.26-4.38 (m, 2H, HCP), 5.43 (m, 2H, HC—N), 6.80-7.75 (m, 70H, ArH), 8.10-8.27 (m, 2H, HC=N). $^{31}$P {$^1$H} NMR (121 MHz; CD$_3$CN): 72.63 ppm (s). Anal. Calcd for C$_{94}$H$_{84}$N$_4$P$_2$FeB$_2$: C, 80.14; H, 6.01; N, 3.98. Found: C, 79.20; H, 6.08; N, 4.65. MS (ESI$^+$) Calcd for [C$_{46}$H$_{44}$N$_4$P$_2$Fe-2(CH$_3$CN)]$^{2+}$: 344.3 m/z. Found: 344.1 m/z. MS (ESI$^-$) Calcd for [B(Ph)$_4$]$^-$: 319.2 m/z. Found: 319.2 m/z.

Example 2

Preparation of the Catalyst (R,R)—[Fe(Ph$_2$PCH$_2$CH=NCH(Ph)CH(Ph)N=CHCH$_2$PPh$_2$)(CH$_3$CN)(CO)][BPh$_4$]$_2$, (ii)

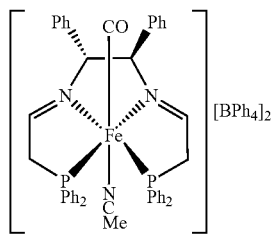

The tetraphenylborate salt of the bisacetonitrile complex (i) (200 mg, 0.142 mmol) was dissolved in (10 mL) of degassed acetone under inert atmosphere. Resulting solution was placed in the CO high pressure reactor and was stirred under 5 atmosphere of CO for 12 hours at room temperature. Solvent was evaporated under reduced pressure and resulting solid was washed with diethyl ether (5 mL) three times. Yellow solid was dried under vacuum. Yield of (ii): 75% (149 mg); $^1$H NMR (400 MHz, acetone-d$_6$) δ: 1.54 (s, 3H, CH$_3$CN), 4.42-4.57 (m, 2H, HC—N), 5.58-5.76 (m, 4H, HCP), 6.80-7.75 (m, 70H, ArH), 8.14-8.23 (m, 2H, HC=N); $^{31}$P {$^1$H} NMR (121 MHz; acetone-d$_6$): 69.3 ppm (d, J$_{P-P}$=30 Hz); 65.7 ppm (d, J$_{P-P}$=30 Hz); MS (ESI$^+$) Calcd for [C$_{46}$H$_{44}$N$_4$P$_2$Fe—(CO+CH$_3$CN)]$^{2+}$: 344.3 m/z. Found: 344.1 m/z. MS (ESI–) Calcd for [B(Ph)$_4$]$^-$: 319.2 m/z. Found: 319.2 m/z, IR (KBr) 2294 cm$^{-1}$ (υC≡N, MeCN), 2001 cm$^{-1}$ (υCO).

Example 3

Preparation of the Complex [Fe(NCMe)$_2${9}]][BF$_4$]$_2$

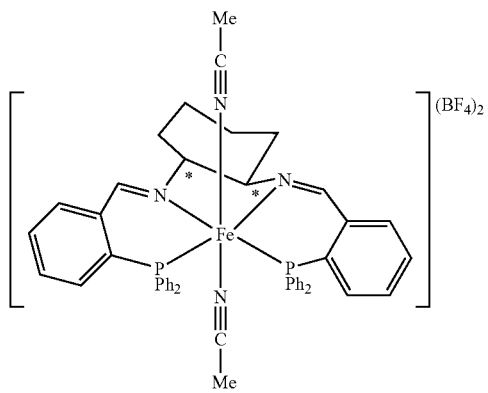

* = R configuration

A suspension of (R,R)-cyP$_2$N$_2$ (9) (317 mg, 0.48 mmol) in 7 mL of MeCN was added dropwise to a solution of [Fe(H$_2$O)$_6$][BF$_4$]$_2$ (162 mg, 0.48 mmol) in MeCN (12 mL). After stirring for 20 min at room temperature, the red solution was concentrated to 1 mL and 10 mL of Et$_2$O were added. A red-orange powder precipitated and was isolated by filtration and washed with Et$_2$O. Recrystallization of [Fe(NCMe)$_2${9}][BF$_4$]$_2$ from a CHCl$_3$/ether solution gave the product (435 mg, 92% yield). A CDCl$_3$ solution in a NMR tube yielded red crystals suitable for X-ray diffraction studies and elemental analysis. 1H NMR (400 MHz, CDCl$_3$) δ=9.26 (s, HC=N), 8.06-6.63 (m, ArH), 3.68 (s, CH), 2.70-2.13 (m, CH2), 1.75 (s, CH$_3$CN). $^{13}$C{$^1$H} NMR (100 MHz, CDCl$_3$) δ: 172.45 (s, HC=N), 138.66-124.84 (m, C$_{aromatic}$ and C≡N), 71.52, 66.05 (s, CH), 31.54, 29.26, 24.16, 22.82 (s, CH$_2$), 1.22 (s, CH$_3$CN). $^{31}$P{$^1$H} NMR (161 MHz, CDCl$_3$) δ: 53.4 (s) ppm. $^{31}$P{$^1$H} NMR (161 MHz, CD$_3$CN) δ: 52.6 (s) ppm. Anal. Calcd. for C$_{48}$H$_{46}$N$_4$B$_2$F$_8$P$_2$Fe$_1$.0.5CHCl$_3$: C, 56.55; H, 4.55; N, 5.44. Found: C, 56.45; H, 4.91; N, 5.04. IR (KBr) 2284 cm$^{-1}$ (υC≡N, MeCN). MS (ESI$^+$, MeOH) for [Fe(9)]$^{2+}$ (m/z=357.1).

Example 4

Preparation of the Catalyst [Fe(NCMe)(CO){9}][BF$_4$]$_2$, (iii)

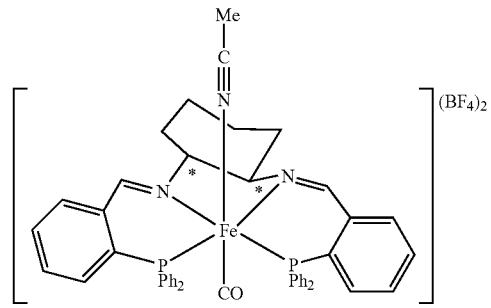

* = R configuration

Method A. A solution of [Fe(MeCN)$_2${9}][BF$_4$]$_2$ (Example 3, 200 mg, 0.21 mmol) in acetone (10 mL) was stirred under 2 atm CO overnight at room temperature. The resulting orange-yellow solution was evaporated to dryness to give an orange powder (quantitative yield).

Method B. A solution of [Fe(MeCN)$_2${9}][BF$_4$]$_2$ (Example 3, 160 mg, 0.17 mmol) in CHCl$_3$ (3 mL) was refluxed under 2 atm CO for 48 hours. The resulting orange-yellow solution was evaporated to dryness to give an orange powder (iii) (quantitative yield).

1H NMR (400 MHz, CDCl$_3$) δ: 9.11 (s, CH=N), 8.21-6.35 (m, ArH), 3.53-3.32 (m, CH), 2.77-1.21 (m, CH$_2$), 1.75 (s, CH$_3$CN). $^{13}$C{$^1$H} NMR (100 MHz, CDCl$_3$) δ: 213.75 (t, $^2$J$_{C-P}$=27.2 Hz, CO), 171.87 (d, $^3$J$_{C-P}$=25.3 Hz, HC=N), 139.42-123.85 (m, Caromatic and C≡N), 70.56, 65.99 (s, CH), 32.22, 30.89, 24.36, 23.71 (s, CH$_2$), 1.03 (s, CH$_3$CN). $^{31}$P{$^1$H} NMR (161 MHz, CDCl$_3$) δ: 51.82 (d, $^2$J$_{P-P}$=40.6 Hz), 48.03 (d, $^2$J$_{P-P}$=40.6 Hz). Anal. Calcd. for C$_{47}$H$_{43}$N$_3$OB$_2$F$_8$P$_2$Fe.0.25CHCl$_3$: C, 57.49; H, 4.42; N, 4.26. Found: C, 57.36; H, 4.99; N, 4.10. IR (KBr) 2294 cm$^{-1}$ (υC≡N, MeCN), 1999 cm-1 (υCO). MS (ESI$^+$, MeOH) for [Fe{9}]$^{2+}$ (m/z=357.1).

Example 5

Preparation of the Catalyst [Fe(NCMe)(CN$^t$Bu){9}][BF$_4$]$_2$, (iv)

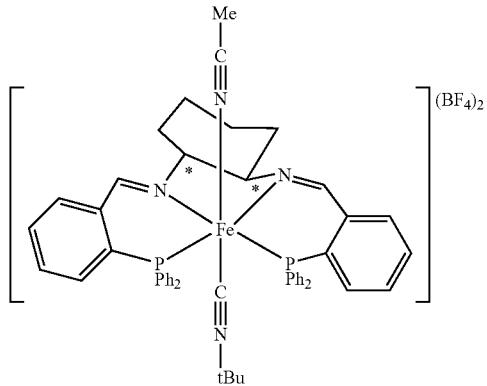

* = R configuration

A solution of [Fe(MeCN)$_2${9}][BF$_4$]$_2$ (Example 3; 95 mg, 0.098 mmol) and tBuNC (22 μL, 0.196 mmol) in acetone (3 mL) was stirred for 2 h at room temperature. The resulting orange-yellow solution was evaporated to dryness to give an orange powder of (iv). (quantitative yield). $^1$H NMR (400 MHz, CDCl$_3$) δ: 9.27, 8.87 (s, CH=N), 8.30-6.55 (m, ArH), 3.71-1.58 (m, CH and CH$_2$), 2.17 (s, CH$_3$CN), 1.21 (s, (CH$_3$)$_3$CNC). $^{13}$C{$^1$H} NMR (100 MHz, CDCl$_3$) δ: 173.47, 171.62 (s, HC=N), 139.60-125.38 (m, C$_{aromatic}$, C≡N and N=C), 75.8, 73.61 (s, CH), 32.38, 31.76, 24.76, 23.90 (s, CH$_2$), 29.45 (s, (CH$_3$)$_3$CNC), 1.03 (s, CH$_3$CN). $^{31}$P{$^1$H} NMR (161 MHz, CDCl$_3$) δ: 58.22 (d, $^2$J$_{P-P}$=51 Hz), 48.48 (d, $^2$J$_{P-P}$=51 Hz). IR (KBr) 2151, 2173 cm$^{-1}$ (υC≡N, MeCN and tBuNC).

Example 6

Preparation of trans-[Fe(NCMe)$_2${(R,R)—PPh$_2$C$_6$H$_4$CHNCHPhCHPhNCHC$_6$H$_4$PPh$_2$}][BF$_4$]$_2$ A solution of (R,R)—PPh$_2$C$_6$H$_4$CHNCHPhCHPhNCHC$_6$H$_4$PPh$_2$ (510 mg, 0.78 mmol) and [Fe(H$_2$O)$_6$][BF$_4$]$_2$ (260 mg, 0.78 mmol) in MeCN (10 mL) was stirred for 1 h at ambient temperature. The solution was evaporated and the remaining red residue was washed with pentane. The analytically pure product was obtained after crystallization from MeCN/Et2O as dark red crystals (510 mg, 64%). Recrystallization from a MeCN/MeOH/Et2O solution yielded crystals suitable for X-ray diffraction studies. 1H NMR (400 MHz, CD3CN): 9.32 (s, CH=N), 7.82-7.21 (m, Ar—H), 6.94 (m, Ar—H), 6.85 (m, Ar—H, 5.97 (s, N—CH), 1.96 (s, CH3CN). 31P{$^1$H} NMR (161 MHz, CDCl$_3$): δ1.8 (s). Anal. Calcd for C56H48N4B2F8P2Fe: C, 62.95; H, 4.53; N, 5.24. Found: C, 62.69; H, 4.79; N, 5.81.

Example 7

Preparation of Catalyst (v): trans-[Fe(NCMe)(CO){(R,R)—PPh$_2$C$_6$H$_4$CHNCHPhCHPhNCHC$_6$H$_4$PPh$_2$}][BF$_4$]$_2$

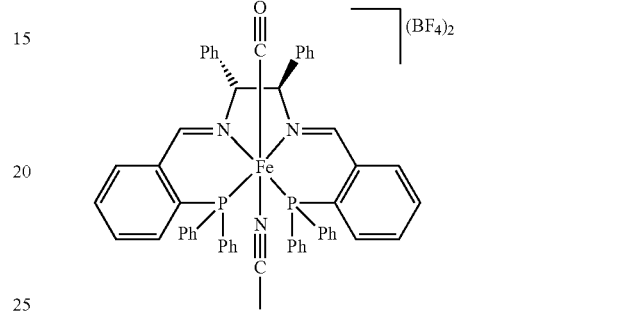

A solution of trans-[Fe(NCMe)$_2${(R,R)—PPh$_2$C$_6$H$_4$CHNCHPhCHPhNCHC$_6$H$_4$PPh$_2$}][BF$_4$]$_2$ (0.51 g, 0.5 mmol) in acetone was stirred under a 5 atm of CO at room temperature for 6 h. The solvents were evaporated, to obtain an orange powder. The powder was again dissolved in acetone and stirred under two atm of CO atmosphere for 12 h at room temperature. The solvents were evaporated and the remaining orange residue was washed with toluene and ether. Crystallization from acetone/CH$_2$Cl$_2$/Et$_2$O gave the analytical pure compound as an orange solid. Yield: 0.47 g (0.4 mmol, 80%). $^1$H NMR (d$^3$-MeCN, 300 MHz, 25° C.): 6.05 (br s, 2H, CH), 6.69-8.06 (several m, 30H, Ph), 9.43 (br s, 2H, CH=N). $^{31}$P NMR (CD$_2$Cl$_2$, 121 MHz): 49.9 (d, J$_{P,P}$=39 Hz), 53.0 (d, J$_{P,P}$=39 Hz). Anal. Calcd. for C$_{55}$H$_{45}$B$_2$F$_8$N$_3$P$_2$Fe$_1$: C, 62.59; H, 4.30; N, 3.98. Found: C, 61.93; H, 4.96; N, 3.67.

Example 8

Preparation of Catalyst (vi): Fe(Ph$_2$PCH$_2$CH=NC$_2$H$_4$N=CHCH$_2$PPh$_2$)(CH$_3$CN)$_2$(BPh$_4$)$_2$]

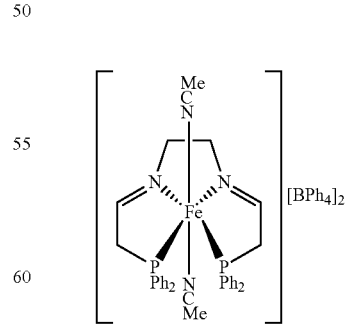

Preparation of precursor solution (A): The reaction was performed in the glove-box under N$_2$ atmosphere at room temperature. The diphenylphosphino-acetaldehyde hydrobromide dimer from Example 1 (200 mg, 0.324 mmol) was partially dissolved in CH₃CN (6 mL). After 5 min of stirring [Fe(H₂O)₆][BF₄]₂ (164 mg, 0.485 mmol) was added to the reaction mixture. t-BuOK (74.0 mg, 0.645 mmol) was added to the reaction mixture and the color of the solution changed from white to yellow. The mixture was stirred at room temperature for 30 min without any observable changes.

A stock solution of the diamine was prepared by dissolving 85.5 mg of 1,2-ethylenediamine in 1.1 mL of acetonitrile. A portion (0.250 mL) of stock solution was added to the precursor solution (A) over the course of 20 min at room temperature. The solution changed color to red-orange after the addition. After 3 h the solution became deep orange. The solution was added to a solution of NaBPh₄ (250 mg, 0.658 mmol) in 1.5 mL of MeOH to cause the formation of the precipitate. The orange-pink solid was filtered and washed with 0.35 mL of MeOH three times and dried under vacuum. Yield: 82% (0.33 mg); ¹H NMR (400 MHz, CD₃CN) J: 1.36 (s, 6H, CH₃CN), 4.10-4.25 (m, 4H, HCP), 4.10-4.25 (m, 4H, HC—N), 6.80-7.55 (m, 60H, ArH), 8.65-8.80 (m, 2H, HC═N). ³¹P {H} NMR (121 MHz; CD₃CN): 74.01 ppm (s). Anal. Calcd for C₈₂H₇₆N₄P₂FeB₂: C, 78.38; H, 6.08; N, 4.46. Found: C, 77.58; H, 6.03; N, 4.26. MS (ESI+) Calcd. for [C₃₄H₃₆N₄P₂Fe-2(CH₃CN)]²⁺: 268.2 m/z. Found: 268.1 m/z. MS (ESI−) Calcd for [B(Ph)₄]−: 319.2 m/z. Found: 319.2 m/z. The crystals were obtained by diffusion of Et₂O (1.0 mL) into the deep orange solution (1 mL) obtained as above but before the addition of NaBPh₄.

Example 9

Preparation of Catalyst (vii): [Fe(Ph₂PCH₂CH═NC₂H₄N═CHCH₂PPh₂)(CH₃CN)(CO)](BPh₄)₂

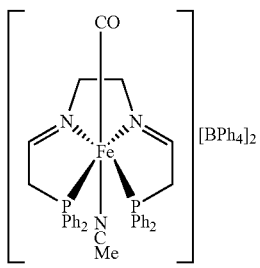

The complex [Fe(Ph₂PCH₂CH═NC₂H₄N═CH—CH₂PPh₂)(CH₃CN)₂](BPh₄)₂ (vi) (200 mg, 0.159 mmol) was dissolved in (10 mL) of degassed acetone under inert atmosphere. Resulting solution was placed in the CO high pressure reactor and was stirred under 5 atmosphere of CO for 12 hours at room temperature. Solvent was evaporated under reduced pressure and resulting solid was washed with diethyl ether (5 mL) three times. Yellow solid was dried under vacuum. Yield of (vii): 80% (158 mg); ¹H NMR (400 MHz, acetone-d₆) δ: 1.72 (s, 3H, CH₃CN), 3.95-4.50 (m, 4H, HC—N), 3.95-4.50 (m, 4H, HCP), 6.55-7.89 (m, 60H, ArH), 8.18-8.46 (m, 2H, HC═N); ³¹P {H} NMR (121 MHz; acetone-d₆): 69.1 ppm (s).

Example 10

Preparation of trans-[Fe(MeCN)₂(6)](BF₄)₂, wherein 6 is

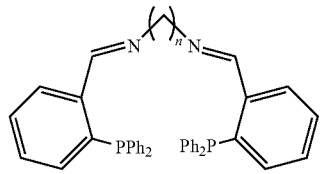

where n = 2

This ligand 6 was prepared as described in Jeffery, J. C.; Rauchfuss, T. B.; Tucker, P. A. *Inorg. Chem.* 1980, 19, 3306-3316. The complex trans-[Fe(MeCN)₂(6)](BF₄)₂ was prepared as follows. A suspension of 6 (149 mg, 0.25 mmol) in 5 mL of MeCN was added to a solution of [Fe(H₂O)₆][BF₄]₂ (84 mg, 0.25 mmol) in MeCN (10 mL). After stirring for 1 h, the red solution was concentrated to 1 mL and 10 mL of Et₂O was added. A purple powder precipitated. The powder was isolated and washed with hexane. (200 mg, 87%). Crystals suitable for X-ray diffraction studies were obtained from a MeCN/Et₂O solution. ¹H NMR (400 MHz, CDCl₃): 9.46 (s, CH═N), 8.07-6.71 (m, ArH), 4.35 (s, CH₂), 2.00 (s, CH₃CN); ³¹P{¹H} NMR (161 MHz, CDCl₃) δ4.4 (s). Anal. Calcd for C₄₄H₄₀N₄B₂F₈P₂Fe: C, 57.68; H, 4.40; N, 6.12%. Found: C, 57.16; H, 4.40; N, 5.86%.

Example 11

Preparation of Catalyst (viii): trans-[Fe(MeCN)(CO)(6)](BF₄)₂

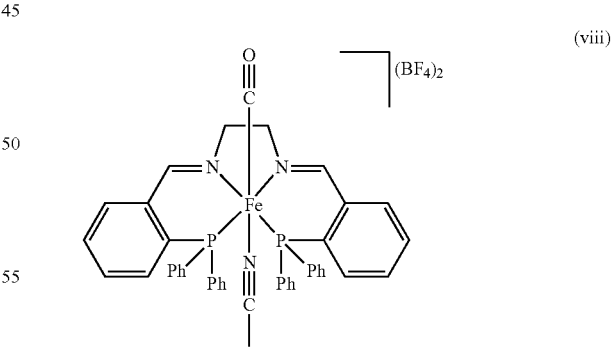

Complex trans-[Fe(MeCN)₂(6)](BF₄)₂ was reacted with CO (2 atm) in acetone at room temperature to produce complex (viii). Yield: 1.14 g (1.3 mmol, 87%.). 1H NMR (d3-MeCN, 300 MHz): 1H NMR 4.01 (br s, 4H, CH2), 7.20-7.98 (several m, 20H, Ph), 9.21 (br s, 2H, CH═N). ³¹P NMR (CD2C12, 121 MHz): 50.8 (s). Anal. Calcd. for C43H37B2F8N3P2Fe1: C, 57.18; H, 4.13; N, 4.65. Found: C, 56.12; H, 4.15; N, 4.83.

Example 12

Preparation of Complex: trans-(R,R)—[Fe(MeCN)$_2$(PPh$_2$CH$_2$CHNC$_6$H$_{10}$NCHCH$_2$PPh$_2$)](BF$_4$)$_2$

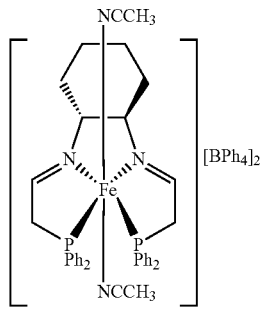

The diphenylphosphino-acetaldehyde hydrobromide dimer from Example 1 (200 mg, 0.324 mmol) was completely dissolved in MeOH (6 mL). [Fe(H$_2$O)$_6$][BF$_4$]$_2$ (164 mg, 0.485 mmol) was added to the reaction mixture. NaOMe (34.9 mg, 0.647 mmol) was added as a MeOH (1 mL) solution and the color of the solution changed from colorless to clear yellow. After 10 min of stirring, 1 mL of acetonitrile was added to give precursor solution B.

(1R,2R)-(−)-1,2-diaminocyclohexane (37 mg, 0.32 mmol) was dissolved in 0.5 mL of acetonitrile and was added to the precursor solution over the course of 20 min. The solution changed color to purple after addition. The resulting solution was heated at 40° C. for 20 h to give a deep orange solution. The solvent volume was reduced by one half and the resulting solution was added to a solution of NaBPh$_4$ (250 mg, 0.658 mmol) in 1.5 mL of MeOH to cause the formation of a precipitate. An orange-red solid was recovered by filtration and washed with 0.15 mL of MeOH three times and dried with vacuum. Yield: 54% (0.23 mg); $^1$H NMR (400 MHz, CD$_3$CN) δ: 1.33 (s, 6H, CH$_3$CN), 1.29-1.39 (m, 2H, H of C$_6$H$_{10}$), 1.68-1.76 (m, 2H, H of C$_6$H$_{10}$), 1.98-2.28 (m, 2H, H of C$_6$H$_{10}$), 2.70-2.78 (m, 2H, H of C$_6$H$_{10}$), 3.54-3.58 (m, 2H, HC—N), 3.88-4.01 (m, 2H, HCP), 4.34-4.49 (m, 2H, HCP), 6.8-7.5 (m, 60H, ArH), 8.60-8.74 (m, 2H, HC=N). $^{31}$P {H} NMR (121 MHz; CD$_3$CN): 73.96 ppm (s). Anal. Calcd for C$_{86}$H$_{82}$N$_4$P$_2$FeB$_2$: C, 78.78; H, 6.31; N, 4.27. Found: C, 77.00; H, 5.99; N, 4.34. MS (ESI$^+$) Calcd for [C$_{38}$H$_{42}$N$_4$P$_2$Fe-2(CH$_3$CN)]$^{2+}$: 268.1 m/z. Found: 268.1 m/z. MS (ESI$^-$) Calcd for [B(Ph)$_4$]$^-$: 319.2 m/z. Found: 319.2 m/z.

Example 13

Preparation of trans-(R,R)—[Fe(CO)(NCMe)(PPh$_2$CH$_2$CHNC$_6$H$_{10}$NCHCH$_2$PPh$_2$)](BF$_4$)$_2$

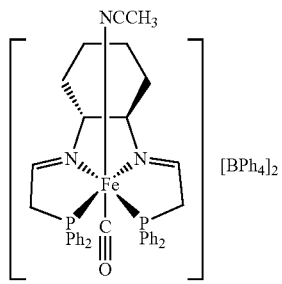

The complex was prepared according to the method of example 9. $^{31}$P NMR (1H) d (66.78, 67.05) and d(70.52, 70.79) J=81 Hz.

Example 14

Preparation of Complex: trans-[Fe(MeCN)$_2$(PPh$_2$CH$_2$CHNC$_6$H$_4$NCHCH$_2$PPh$_2$)](BF$_4$)$_2$

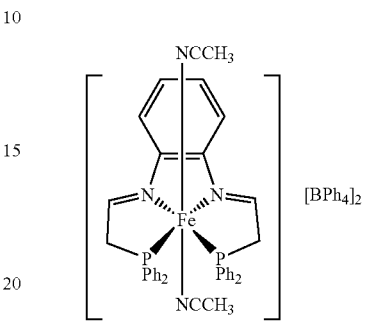

Ortho-phenylenediamine (35 mg, 0.32 mmol) was dissolved in 0.5 mL of acetonitrile and was added to the precursor solution (A) of Example 8 over the course of 20 minutes at 22° C. The solution changed color to orange after the addition. The resulting residue was added to the solution of NaBPh$_4$ (250 mg, 0.658 mmol) in 1 mL of MeOH to cause the formation of the precipitate. The red-orange solid was isolated by filtration and washed with 0.15 mL of MeOH three times and dried under vacuum. Yield: 86% (0.36 mg); $^1$H NMR (400 MHz, CD$_3$CN) δ: 2.10 (s, 6H, CH$_3$CN), 4.52-4.60 (m, 4H, HCP), 6.80-8.20 (m, 64H, HAr), 9.32-9.44 (m, 2H, HC=N). $^{31}$P {H} NMR (121 MHz; CD$_3$CN): 68.33 ppm (s). Anal. Calcd for C$_{38}$H$_{36}$N$_4$P$_2$FeB$_2$: C, 79.19; H, 5.87; N, 4.29. Found: C, 76.83; H, 5.80; N, 4.15. MS (ESI$^+$) Calcd for [C$_{86}$H$_{76}$N$_4$P$_2$Fe-2(CH$_3$CN)]$^{2+}$: 292.2 m/z. Found: 292.1 m/z. MS (ESI$^-$) Calcd for [B(Ph)$_4$]$^-$: 319.2 m/z. Found: 319.2 m/z.

Example 15

Preparation of the dicyclohexylphosphino-acetaldehyde hydrobromide Dimer

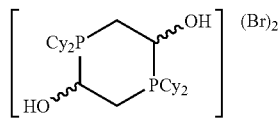

meso- and rac-

A Schlenk flask was charged with dicyclohexylphosphine (2.53 g, 0.013 mol) and dry THF (10 mL). Bromoacetaldehyde diethyl acetal (2.50 g, 0.013 mol) was added over the course of 15 min. The mixture was stirred for 1 hour, at which time a white precipitate was evident. An excess amount of degassed water (1 mL) was added and the mixture was allowed to reflux overnight to yield a pristine white sludge. The solid was collected by filtration under air and washed with water (2×3 mL) and diethyl ether (2×3 mL). Drying in vacuo yielded the phosphonium dimer as an air-stable white powder. Yield: 3.25 g (80%); $^1$H NMR (400 MHz, CD$_3$CN) δ: 1.42-2.19 (m, HCy), 2.80 (q), 3.08 (m), 5.39 (dd, J$_{HP}$=26 Hz, J$_{HH}$=4 Hz), 5.23 (dd, J$_{HP}$=22 Hz, J$_{HH}$=4 Hz). $^{31}$P {$^1$H} NMR (121 MHz; CD$_3$CN) δ: 27.2 (s), 28.1 (s). Anal. Calcd for C$_{28}$H$_{52}$O$_2$P$_2$Br$_2$: C, 52.35; H, 8.16. Found: C, 51.93; H, 8.46. MS (ESI, methanol/water; m/z$^+$): 241.2 [C$_{28}$H$_{52}$O$_2$P$_2$]$^{2+}$.

Example 16

Preparation of Complex: [Fe(Cy$_2$PCH$_2$CH=NC$_2$H$_4$N=CHCH$_2$PCy$_2$)(CH$_3$CN)$_2$](BPh$_4$)$_2$]

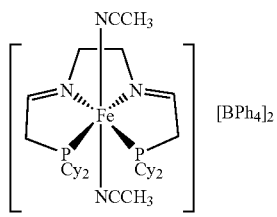

A vial was charged with the dicyclohexylphosphino-acetaldehyde hydrobromide dimer (200 mg, 0.311 mmol), KOtBu (70 mg, 0.623 mmol) and CH$_3$CN (4 mL). After stirring for 5 minutes, [Fe(H$_2$O)$_6$][BF$_4$]$_2$ (158 mg, 0.467 mmol) in CH$_3$CN (2 mL) was added to the white slurry. The solution turned grey-yellow after 5 minutes; ethylenediamine (0.34 mL from a stock solution of 200 mg in 4 mL CH$_3$CN) was added. The mixture turned pink immediately. After the reaction has gone to completion overnight, the mixture was filtered through a pad of Celite to remove a grey-white precipitate. Solvent was removed under reduced pressure to give a red-pink residue. The solid was dissolved in MeOH (2 mL) and added to a solution of NaBPh$_4$ (234 mg, 0.685 mmol) in MeOH (1 mL) to cause precipitation of a pale pink solid. The solid was filtered and washed with MeOH (2×1 mL) and dried under vacuum. Yield: 80% (319 mg). Single crystals suitable for an X-ray diffraction study were obtained by slow diffusion of pentane into CH$_3$CN/CH$_2$Cl$_2$ (1:1 by volume) at −40° C. $^1$H NMR (400 MHz, CD$_3$CN) δ: 1.11-1.95 (m, HCy, CH$_3$), 3.31 (d, 4H, H$_2$CP), 3.95 (s, 4H, H$_2$C—N), 6.8-7.3 (m, HAr), 8.41 (m, 2H, HC=N). $^{13}$C{$^1$H} NMR (100 MHz, CD$_3$CN) δ: 26.58 (C$_{Cy}$), 27.63 (t, J$_{CP}$=5.1 Hz, C$_{Cy}$), 27.82 (t, J$_{CP}$=5.1 Hz, C$_{Cy}$), 29.87 (C$_{Cy}$), 30.04 (C$_{Cy}$), 35.72 (t, J$_{CP}$=6.9 Hz, C$_{Cy}$P), 36.92 (dd, J$_{CP}$=15, 10 Hz, CH$_2$P), 61.10 (CH$_2$N), 122.61 (C$_{Ph}$B), 126.43 (q, J$_{CB}$=2.7 Hz, C$_{Ph}$B), 136.58 (q, J$_{CB}$=1.4 Hz, C$_{Ph}$B), 164.62 (m, J$_{CB}$=49 Hz, C$_{Ph}$B), 177.86 (HC=N). $^{31}$P{$^1$H} NMR (161 MHz, CD$_3$CN) δ: 68.5 (s). Anal. Calcd for C$_{82}$H$_{100}$N$_4$P$_2$FeB$_2$: C, 76.88; H, 7.87; N, 4.37. Found: C, 71.23; H, 7.51; N, 4.47. MS (ESI, methanol/water; m/z$^+$): 505.4 [C$_{30}$H$_{55}$N$_2$P$_2$—(Fe(NCCH$_3$)$_2$)]$^+$.

Example 17

Preparation of Catalyst Precursor: [Fe(Cy$_2$PCH$_2$CH=NC$_2$H$_4$N=CHCH$_2$PCy$_2$)(Br)(CO)][BPh$_4$]

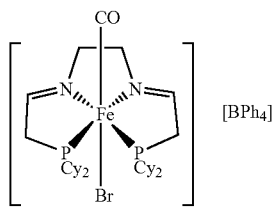

A vial was charged with the dicyclohexylphosphino-acetaldehyde hydrobromide dimer (200 mg, 0.311 mmol), KOtBu (70 mg, 0.623 mmol) and CH$_3$CN (4 mL). After stirring for 5 minutes, [Fe(H$_2$O)$_6$][BF$_4$]$_2$ (158 mg, 0.467 mmol) in CH$_3$CN (2 mL) was added to the white slurry. The solution turned grey-yellow after 5 minutes; ethylenediamine (0.34 mL from a stock solution of 200 mg in 4 mL CH$_3$CN) was added. The mixture turned pink immediately. After the reaction has gone to completion overnight, the mixture was filtered through a pad of Celite to remove a grey-white precipitate and then transferred to a Shlenk flask. Solvent was removed under reduced pressure to give a red-pink residue. Acetone (15 mL) was added and the solution was stirred under constant flow of CO overnight. The resulting yellow-brown solution was evaporated to dryness, dissolved in MeOH (2 mL) and added to a solution of NaBPh$_4$ (94 mg, 0.274 mmol) in 1 mL of MeOH to cause formation of a yellow precipitate. Yield: 63% (150 mg). Single crystals suitable for an X-ray diffraction study were obtained by slow diffusion of hexanes into THF. $^1$H NMR (400 MHz, CD$_2$Cl$_2$) δ: 1.20-1.39 (m, HCy), 2.50 (br. m, 2H, HCyP) 2.86 (dd, J$_{HP}$=19.0 Hz, 2H, HCP), 3.27 (dd, J$_{HP}$=20.0 Hz, 2H, HCP), 3.44 (m, J$_{HH}$=6.2 Hz, 2H, HCN), 3.81 (m, J$_{HH}$=5.6 Hz, 2H, HCN), 6.88-7.39 (m, HAr), 7.49 (m, 2H, HC=N). $^{13}$C{$^1$H} NMR (100 MHz, CD$_2$Cl$_2$) δ: 26.34 (d), 27.80 (m), 29.47 (t), 30.24, 30.75 (d), 38.29 (q), 39.73 (dd), 60.93, 105.35, 122.65, 126.52, 136.71, 164.01-165.68 (m, J$_{C—B}$ 49 Hz), 174.42. $^{31}$P{$^1$H} NMR (161 MHz, CD$_2$Cl$_2$) δ: 69.78 ppm. IR (KBr) 1948 cm$^{-1}$ (ν$_{C=O}$). Anal. Calcd for C$_{55}$H$_{74}$BBrFeN$_2$OP$_2$: C, 66.88; H, 7.55; N, 2.84. Found: C, 65.30; H, 7.89; N, 3.15.

Example 18

Preparation of the di(p-tolyl)phosphino-acetaldehyde hydrobromide Dimer

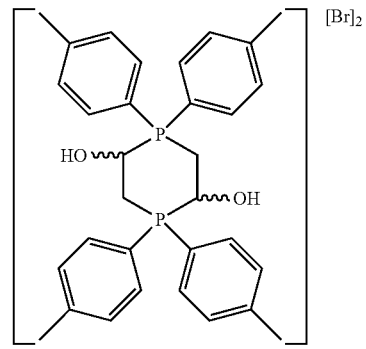

A Schlenk flask was charged with KH (0.524 g, 13.1 mmol), and dry THF (13 mL). Di(p-tolyl)phosphine (2.331 g, 10.9 mmol) was added, and the solution turned red in colour. The solution was stirred for 30 min, and then cooled to −78° C. Bromoacetadehyde diethyl acetate (1.68 mL, 10.9 mmol) was added over 20 min, and the solution turned yellow. The solution was warmed to room temperature and 48% HBr (2.5 g, 14.8 mmol) was added. A white precipitate formed, and the solution turned colourless. The mixture was heated at 45° C. for 2 hours, and then left in the freezer overnight. The precipitate was filtered off and washed with 15 mL cold H$_2$O, as well as 15 mL of a 1:1 mixture of cyclohexanol:ethyl acetate. The precipitate was then recrystallized in MeOH and ether, and dried under high vacuum. Yield: 2.698 g, 87.8%. Diastereomer 1: 1H NMR (CD$_3$OD, 400 MHz, δ): 8.06 (dd, J=8.2, 12.3, aromatic CH, 4H), 7.63-7.58 (m, aromatic CH, 8H), 7.48 (dd, J=2.5, 8.2, aromatic CH, 4H), 6.19 (dd, J=6.8, 21.5, PCH(OH), 2H), 4.37-4.15 (m, H1 of PCH(OH)CH$_2$, 2H), 3.99-3.81 (m, H2 of PCH(OH)CH$_2$, 2H), 2.53 (s, CH3, 6H), 2.44 (s, CH3, 6H). $^{31}$P NMR (CD$_3$OD, 400 MHz, δ): 11.12. $^{13}$C NMR (CD$_3$OD, 400 MHz, δ): 146.8 (aromatic C—P), 146.7 (aromatic C—P), 133.7 (aromatic CH), 133.1 (aromatic CH), 130.6 (aromatic CH), 130.4 (aromatic CH), 113.9 (CH$_3$C), 113.0 (CH$_3$C), 61.1 (PCHOH), 22.1 (PCH$_2$), 20.5 (CH$_3$), 20.3 (CH$_3$). Diastereomer 2: 1H NMR (CD$_3$OD, 400 MHz, δ): 7.96 (dd, J=8.3, 12.5, aromatic CH, 4H), 7.86 (dd, J=8.3, 12.0, aromatic CH, 4H), 7.63-7.58 (m, aromatic CH, 4H), 7.56 (dd, J=3.2, 8.3, aromatic CH, 4H), 5.80 (ddd, J=2.5, 9.4, 16.3, PCH(OH), 2H), 4.37-4.15 (m, H1 of PCH(OH) CH$_2$, 2H), 3.99-3.81 (m, H2 of PCH(OH)CH$_2$, 2H), 2.50 (s, CH3, 6H), 2.49 (s, CH3, 6H). $^{31}$P NMR (CD$_3$OD, 400 MHz, δ): 16.06. $^{13}$C NMR (CD3OD, 400 MHz, δ): 147.5 (aromatic C—P), 146.9 (aromatic C—P), 133.3 (aromatic CH), 132.9 (aromatic CH), 131.3 (aromatic CH), 130.5 (aromatic CH), 112.5 (CH$_3$C), 111.7 (CH$^3$C), 62.2 (PCHOH), 23.6 (PCH$_2$), 20.4 (CH3). Anal. Calcd for [C$_{32}$H$_{36}$P$_2$O$_2$][Br]$_2$[CH$_3$OH][H$_2$O]: C, 54.71; H, 5.84. Found: C, 54.65; H, 6.04. MS (ESI, methanol/water; m/z+): 257.1 [C$_{32}$H$_{36}$O$_2$P$_2$]$^{2+}$. The diastereomeric excess was found to be 13%, as determined by $^1$H NMR, and $^{31}$P NMR.

Example 19

Preparation of Catalyst Precursor:
[Fe((C$_7$H$_7$)$_2$PCH$_2$CH=NCHPhCHPhN=CHCH$_2$P(C$_7$H$_7$)(CH$_3$CN)$_2$](BPh$_4$)$_2$]

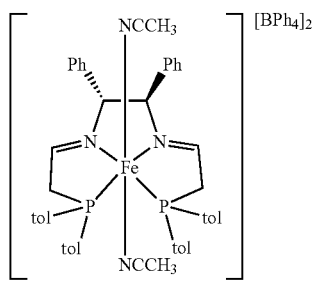

A vial was charged with the di(p-tolyl)phosphino-acetaldehyde hydrobromide dimer (235 mg, 0.324 mmol), and CH$_3$CN (4 mL). A yellow solution of [Fe(H$_2$O)$_6$][BF$_4$]$_2$ (164 mg, 0.485 mmol) in CH$_3$CN (2 mL) was added to the white slurry, followed by NaOMe (34.9 mg, 0.647 mmol) in MeOH (1 mL). The color of the solution changed from yellow to colourless. After 20 min of stirring (1R,2R)-(+)-1,2-diphenylethylenediamine (69 mg, 0.323 mmol) in 0.5 mL of acetonitrile was added over 5 min, and the solution turned deep purple. After 48 h the mixture was filtered to remove a white precipitate. The solvent was removed under reduced pressure to give a red-pink residue. The residue was dissolved in MeOH (2 mL) and added to a solution of NaBPh$_4$ (250 mg, 0.658 mmol) in MeOH (1 mL) to cause precipitation of a pale pink solid. The product was filtered and washed with MeOH (2×5 mL) and dried under vacuum. Yield: 26.3% (120 mg). Crystals suitable for X-ray diffraction studies were obtained by slow diffusion of Et$_2$O into CH$_3$CN/MeOH (1:5 by volume). $^1$H NMR (400 MHz, CD$_3$CN) δ: 2.20 (s, 6H, CH$_3$CN), 3.90-4.03 (m, 2H, HCP), 4.15-4.30 (m, 2H, HCP), 5.42 (m, 2H, HC—N), 6.80-7.75 (m, 74H, aromatic H), 8.90-8.20 (m, 2H, HC=N). $^{31}$P {1H} NMR (121 MHz; CD3CN) δ: 70.52 ppm (s). Anal. Calcd for [C$_{98}$H$_{92}$N$_4$P$_2$FeB$_2$]: C, 80.33; H, 6.33; N, 3.82. Found: C, 76.31; H, 6.71; N, 3.77. MS (ESI, methanol/water; m/z+): 372.1 [C$_{50}$H$_{52}$N$_4$P$_2$Fe]$^{2+}$.

Example 20

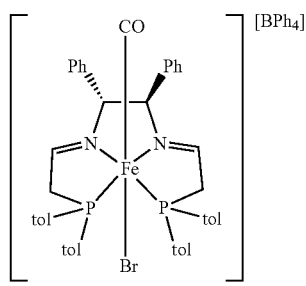

Following the same steps as in the synthesis of Example 19, the reaction mixture that was stirred for 48 h was filtered and transferred to a Schlenk flask. The solvent was removed under pressure, and acetone (9 mL) was added. The solution was stirred under a constant flow of CO overnight. The resulting yellow-brown solution was evaporated to dryness, dissolved in MeOH (4 mL) and added to a solution of NaBPh$_4$ (125 mg, 0.329 mmol) in MeOH (1 mL) to cause formation of a yellow precipitate. Yield: 22.2% (108 mg). $^{31}$P {$^1$H} NMR (121 MHz; C$_6$D$_6$ insert) δ: 65.96 (d, J=39.5 Hz), 67.93 ppm (d, J=39.5 Hz).

General Procedure for Examples 21 and 22

In an Ar-filled glovebox diisopropylphosphine (for Example 21) or diethylphosphine (for Example 22) (15 mmol) was dissolved in 20 mL of dry THF. Bromoacetadehyde diethyl acetal (15 mmol) was added to the resulting mixture on Ar line and resulting solution was stirred for 4 h. The reaction was quenched with degassed H$_2$O (8 mL) and heated for over night at 45° C. The solvent was partially removed under vacuum and to give colorless solution with white precipitate. The solution was stored for 3 h at 5° C. The precipitate then was filtered and washed with pre-cooled water (15 mL) and diethyl ether (10 mL) to give an analytically pure sample. Crystals suitable for X-ray diffraction experiments were obtained by slow diffusion of diethyl ether into a saturated solution of Example 22 in methanol.

Example 21

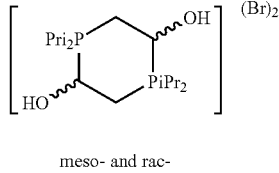

meso- and rac-

Properties of the di(i-propyl)phosphino-acetaldehyde hydrobromide Dimer

Yield: 2.93 g, 81%. The diastereomeric ratio was found to be 1:2, as determined by $^1$H NMR. $^1$H NMR (400 MHz, CD$_3$OD, resonances of two diastereomers overlap in region δ 3.50-1.40; see below): δ 5.60 (pseudo ddd, $^3J_{HH}$=6.4 Hz, $^2J_{HP}$=22.3 Hz, 2H, CH(OH), major diastereomer; $^{31}$P{$^1$H}, 5.60 (pseudo d, $^3J_{HH}$=6.5 Hz)), 5.44 (ddd, 1H, $^3J_{HH}$=3.0 Hz, $^3J_{HH}$=9.3 Hz, $^2J_{HP}$=12.0 Hz, 2H, CH(OH), minor diastereomer; $^1$H{$^{31}$P}, 5.44 (dd, $^3J_{HH}$=3.0 Hz, $^3J_{HH}$=9.3 Hz)), 3.50-2.85 (m, overlap of 4H, CH(OH)CH$_2$P and 4H, (CH$_3$)$_2$CHP (both diastereomers); $^1$H{$^{31}$P}, same), 1.60-1.40 (m, 12H, (CH$_3$)$_2$CHP, (both diastereomers); $^1$H{$^{31}$P}, same). $^{31}$P{$^1$H} NMR (161 MHz, CD$_3$OD): δ 36.81 (s, minor diastereomer), 34.54 (s, major diastereomer). $^{13}$C{$^1$H} NMR (100 MHz, CD$_3$OD, signals of carbon atoms appear as a multiplets with complex splitting patterns that arise from coupling to two magnetically inequivalent phosphorus atoms in the structure): δ 58.61 (m, CH(OH), minor diastereomer), 57.69 (m, CH(OH), major diastereomer), 22.93 (m, CH$_2$P, major diastereomer), 22.93 (m, CH$_2$P, minor diastereomer), 21.23 (m, CH$_2$P, major diastereomer), 21.62 (d, $^2J_{CP}$=21.8 Hz, C(CH$_3$)$_2$P, minor diastereomer) 19.71 (d, $^2J_{CP}$=40.5 Hz, C(CH$_3$)$_2$P, major diastereomer), 16.45-15.35 (m, overlapping peaks of isopropyl methyl groups, both diastereomers). Anal. Calcd for C$_{16}$H$_{36}$P$_2$O$_2$Br$_2$: C, 39.85; H, 7.52. Found: C, 39.35; H, 7.32.

Example 22

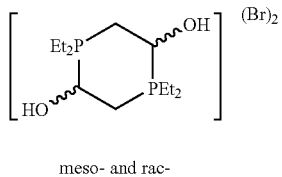

meso- and rac-

Properties of the di(ethyl)phosphino-acetaldehyde hydrobromide Dimer

Yield: 1.28 g, 40%. The diastereomeric ratio was found to be 1:2, as determined by $^1$H NMR. $^1$H NMR (400 MHz, CD$_3$OD, resonances of two diastereomers overlap; see below): δ 5.45-510 (m, 2H, CH(OH), diastereomers overlap; $^1$H{$^{31}$P}, 5.36 (pseudo d, 2H, CH(OH), $^2J_{H-P}$=5.8 Hz, major diastereomer), 5.29 (pseudo dd, 2H, CH(OH), $^3J_{H-H}$=3.4 Hz, $^2J_{H-P}$=9.2 Hz, minor diastereomer)), 3.31-2.87 (m, 4H, CH(OH)CH$_2$P, overlap of diastereomers; $^1$H{$^{31}$P}, same), 2.58-2.08 (m, 8H, (CH$_3$CH$_2$P, overlap of diastereomers; $^1$H{$^{31}$P}; same), 1.32-0.90 (m, 12H, CH$_3$CH$_2$P, overlap of diastereomers; $^1$H{$^{31}$P}, same). $^{31}$P{$^1$H} NMR (161 MHz, CD$_3$OD): δ 35.59 (s, minor diastereomer), 32.72 (s, major diastereomer). $^{13}$C{$^1$H} NMR (100 MHz, CD$_3$OD, complex coupling of several carbon atoms results from coupling to two magnetically unequivalent phosphorus atoms in the structure): δ 58.10 (m, CH(OH), minor diastereomer), 57.85 (m, CH(OH), major diastereomer), 19.54 (m, CH$_2$P, minor diastereomer), 18.35 (m, CH$_2$P, major diastereomer), 12.50-9.12 (m, CH$_3$CH$_2$P, overlap of diastereomer), 5.42-3.72 (m, CH$_3$CH$_2$P, overlap of diastereomer). Anal. Calcd for C$_{12}$H$_{28}$P$_2$O$_2$Br$_2$: C, 33.82; H, 6.62. Found: C, 33.92; H, 6.38.

While the present invention has been described with reference to examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

What is claimed is:
1. A hexa-coordinate iron (II) complex comprising a compound of formula (I):

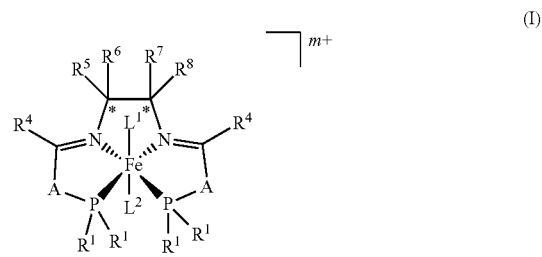

wherein
each R$^1$ is independently selected from the group consisting of aryl, heteroaryl, C$_1$-C$_8$ alkyl, C$_2$-C$_8$ alkenyl, C$_1$-C$_8$ alkoxy, aryloxy, and cycloalkyl, all of which may be optionally substituted; two geminal R$^1$ groups may combine to form a C$_2$-C$_4$ linear alkyl diradical or C$_3$-C$_8$ branched alkyl diradical, each of which may be optionally substituted, to form a ring together with the phosphorus atom to which they are attached; or two R$^1$ groups, each of which is located on a different phosphorus atom, may combine to form a linker M, wherein M is selected from the group consisting of C$_2$-C$_4$ linear alkyl diradical and C$_3$-C$_8$ branched alkyl diradical, each of which may be optionally substituted, or M may be a diradical ligand with a wide bite angle;
A is selected from:

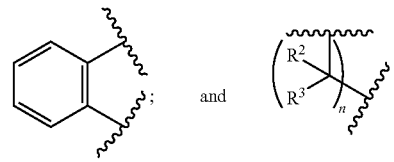

wherein each of R$^2$ and R$^3$ is independently selected from the group consisting of H, substituted or unsubstituted C$_1$-C$_8$ alkyl, substituted or unsubstituted C$_2$-C$_8$ alkenyl, substituted or unsubstituted aryl, and substituted or unsubstituted cycloalkyl, and each n is an integer independently selected from 1, 2, and 3;
each R$^4$ is independently selected from the group consisting of H, substituted or unsubstituted C$_1$-C$_8$ alkyl, substituted or unsubstituted C$_2$-C$_8$ alkenyl, substituted or unsubstituted aryl, and substituted or unsubstituted cycloalkyl;
each R$^5$, R$^6$, R$^7$ and R$^8$ is independently selected from the group consisting of H, substituted or unsubstituted C$_1$-C$_8$ alkyl, substituted or unsubstituted C$_2$-C$_8$ alkenyl, substituted or unsubstituted aryl, and substituted or unsubstituted cycloalkyl; $R^5$ and $R^6$, together with the carbon atom to which they are attached, may combine to form a substituted or unsubstituted cycloalkyl ring of size from 5-8 carbons; $R^7$ and $R^8$, together with the carbon atom to which they are attached, may combine to form a substituted or unsubstituted cycloalkyl ring of size from 5-8 carbons; or $R^5$, $R^6$, $R^7$ and $R^8$, together with the carbon atoms to which they are attached, may combine to form a group selected from

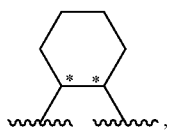, and 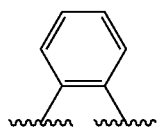

each of which may be optionally substituted with one or more substituents selected from the group consisting of $C_1$-$C_8$ alkyl, $C_1$-$C_8$ alkoxy, and halogen atoms;

$L^1$ and $L^2$ are independently selected from the group consisting of CO; hydride; pyridine and derivatives thereof; imidazole and derivatives thereof; halide ion; NCR, CNR and $^-$OR, wherein R is independently selected from the group consisting of aryl, heteroaryl, $C_1$-$C_8$ alkyl, $C_2$-$C_8$ alkenyl and cycloalkyl, all of which may be optionally substituted; $R^a R^b R^c N$ wherein $R^a$, $R^b$, and $R^c$ are independently selected from the group consisting of H and $C_1$-$C_2$ alkyl; and $R^c(CO)R^d$ wherein $R^c$ and $R^d$ are independently selected from the group consisting of $C_1$-$C_8$ alkyl, aryl, and heteroaryl;

m represents the charge of the compound of formula (I) and is 0, +1, or +2; and when m is +1 or +2, the iron (II) complex comprises at least one counter ion to counterbalance the charge of the compound of formula (I);

with the following provisos:

(a) when A is

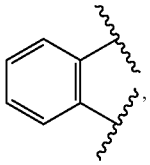 [SMILES: *c1ccccc1*]

then at least one of $L^1$ and $L^2$ must be selected from the group consisting of CO and CNR, wherein R is as defined above;

(b) when each $R^1$ is phenyl:

A is not

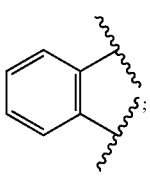 [SMILES: *c1ccccc1*]

each $R^4$ is not H;

$R^5$, $R^6$, $R^7$ and $R^8$, together with the carbon atoms to which they are attached, do not combine to form a group selected from

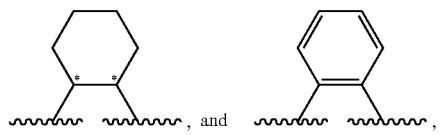 [SMILES: *C1CCCCC1* ; *c1ccccc1*], and 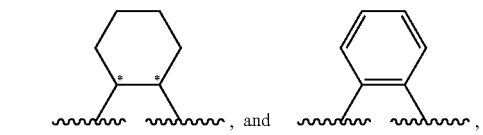, each of which is unsubstituted or is substituted with one or more substituents selected from the group consisting of $C_1$-$C_8$ alkyl, $C_1$-$C_8$ alkoxy, and halogen atoms;

$L^1$ is not $CH_3CN$;

$L^2$ is not selected from the group consisting of $CH_3CN$, CO and CNtBu; and m is not +2;

(c) when each $R^1$ is phenyl:

A is not

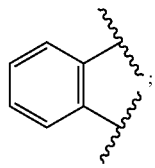 [SMILES: *c1ccccc1*]

each $R^4$ is not H;

each $R^5$, $R^6$, $R^7$ and $R^8$ is not H;

$L^1$ is not $CH_3CN$;

$L^2$ is not selected from the group consisting of $CH_3CN$, CO and CNtBu; and m is not +2; and and the iron(II) complex does not comprise $BF_4^-$;

(d) when each $R^1$ is phenyl:

A is not

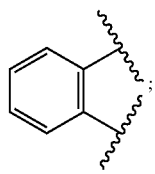 [SMILES: *c1ccccc1*]

each $R^4$ is not H;

each of $R^5$ and $R^8$ is not phenyl, and each of $R^6$ and $R^7$ is not H;

$L^1$ is not $CH_3CN$;

$L^2$ is not selected from the group consisting of $CH_3CN$, CO, and CNtBu; and m is not +2; and and the iron (II) complex does not comprise the anion $BPh_4^-$;

(e) when each $R^1$ is alkyl:

A is not

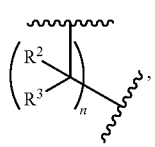

wherein each R² and R³ is H, and n is the integer 1;
each R⁴ is not H;
each R⁵, R⁶, R⁷ and R⁸ is not hydrogen, alkenyl, substituted or unsubstituted aryl, and substituted or unsubstituted cycloalkyl; R⁵ and R⁶, together with the carbon atom to which they are attached, may not combine to form a substituted or unsubstituted cycloalkyl ring of size from 5-8 carbons; R⁷ and R⁸, together with the carbon atom to which they are attached, may not combine to form a substituted or unsubstituted cycloalkyl ring of size from 5-8 carbons; or R⁵, R⁶, R⁷ and R⁸, together with the carbon atoms to which they are attached, may not combine to form a group selected from

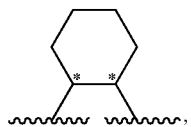 and 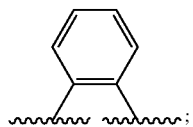;

each of which is unsubstituted or substituted with one or more substituents selected from the group consisting of $C_1$-$C_8$ alkyl, $C_1$-$C_8$ alkoxy, and halogen atoms;
$L^1$ is not $CH_3CN$;
$L^2$ is not selected from the group consisting of $CH_3CN$, CO, and CNtBu;
m is not +2; and
the iron (II) complex does not comprise the anion $BF_4^-$;
(f) when each $R^1$ is phenyl;
A is not

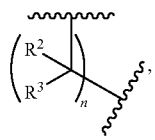, wherein each R² and R³ is H and each n is the integer 1;
each R⁴ is not H;
each R⁵, R⁶, R⁷ and R⁸ is not H, or R⁵ and R⁷ are not H and R⁶ and R⁸ are not phenyl in one of the (R,R) or (S,S) configurations, or R⁵, R⁶, R⁷ and R⁸, together with the carbon atoms to which they are attached, may not combine to form a group selected from

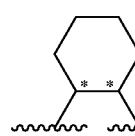, and 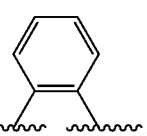;

$L^1$ is not $CH_3CN$;
$L^2$ is not selected from the group consisting of CO, $CH_3CN$ and CNtBu;
m is not +2;

and the iron (II) complex does not comprise the anion $BF_4^-$

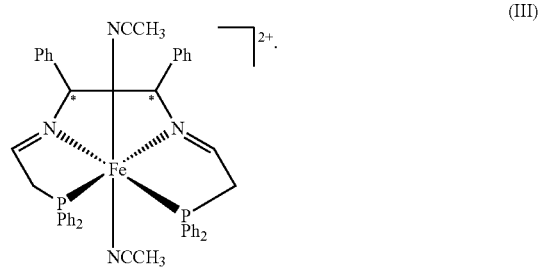

2. The hexa-coordinate iron (II) complex of claim 1, wherein a trans coordination geometry is achieved at iron through nitrogen and phosphorus donor bonds of a tetradentate diimino-diphosphine templated ligand of the formula (II):

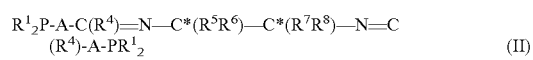

and $L^1$ and $L^2$ are in an axial coordination above and below the templated ligand, respectively.

3. The hexa-coordinate iron (II) complex of claim 1, wherein the at least one counter ion is selected from the group consisting of $BF_4^-$; $PF_6^-$; $SbF_6^-$; $ClO_4^-$; $CH_3SO_3^-$; $CF_3SO_3^-$; $C_6H_5SO_3^-$; p-$CH_3C_6H_4SO_3^-$; $FeCl_4^{2-}$; $FeBr_4^{2-}$; $B(R^*)_4^-$, wherein R* is selected from the group consisting of phenyl, $C_6H_3(CF_3)_2$ and $C_6F_5$; halides; pseudohalides; $C_1$-$C_8$ alkoxides; and aryloxides.

4. The hexa-coordinate iron (II) complex of claim 3, wherein $R^1$ is phenyl.

5. A hexa-coordinate iron (II) complex comprising a compound of formula (I):

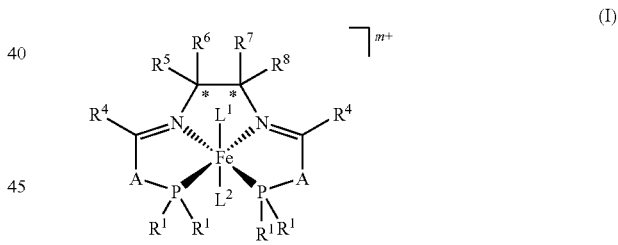

wherein
each $R^1$ is phenyl;
A is

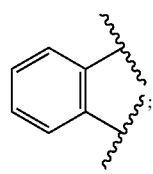 [SMILES: *c1ccccc1*];

each $R^4$ is H;
$R^5$=$R^6$=$R^7$=$R^8$=H;
$L^1$ is $CH_3CN$;
$L^2$ is selected from the group consisting of CO and CNtBu;
m is +2; and
the iron (II) complex comprises $BF_4^-$.

6. A hexa-coordinate iron (II) complex, comprising a compound of formula (I):

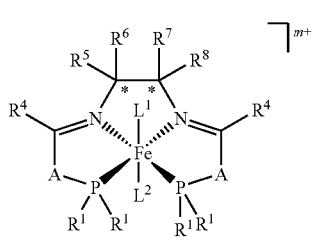

wherein
each $R^1$ is alkyl;
A is

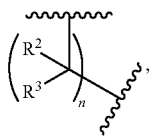

wherein $R^2=R^3=H$, and n=1;
each $R^4$ is H;
each $R^5$, $R^6$, $R^7$ and $R^8$ is hydrogen, alkenyl, substituted or unsubstituted aryl, and substituted or unsubstituted cycloalkyl; $R^5$ and $R^6$, together with the carbon atom to which they are attached, may combine to form a substituted or unsubstituted cycloalkyl ring of size from 5-8 carbons; $R^7$ and $R^8$, together with the carbon atom to which they are attached, may combine to form a substituted or unsubstituted cycloalkyl ring of size from 5-8 carbons; or $R^5$, $R^6$, $R^7$ and $R^8$, together with the carbon atoms to which they are attached, may combine to form a group selected from

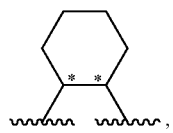 , and 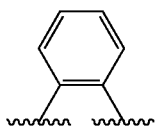 ;

each of which is unsubstituted or substituted with one or more substituents selected from the group consisting of $C_1$-$C_8$ alkyl, $C_1$-$C_8$ alkoxy, and halogen atoms;
$L^1$ is $CH_3CN$;
$L^2$ is selected from the group consisting of $CH_3CN$, CO, and CNtBu;
m is +2; and
and the iron (II) complex comprises the anion $BPh_4^-$.

7. The hexa-coordinate iron (II) complex of claim 6, wherein the chiral carbon atoms denoted by asterisks: both have an R configuration, or both have an S configuration.

8. A hexa-coordinate iron (II) complex comprising a compound of formula (I):

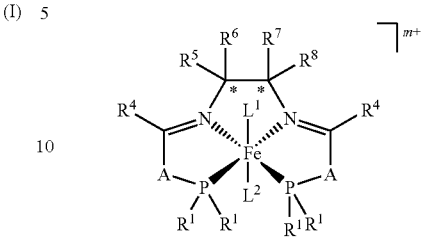

wherein
each $R^1$ is phenyl;
A is

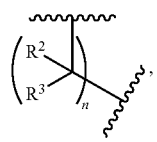

wherein $R^2=R^3=H$ and each n=1;
each $R^4$ is H;
$R^5=R^6=R^7=R^8=H$, or $R^5$ and $R^7$ are H and $R^6$ and $R^8$ are phenyl in one of the (R,R) or (S,S) configurations, or $R^5$, $R^6$, $R^7$ and $R^8$, together with the carbon atoms to which they are attached, may not combine to form a group selected from

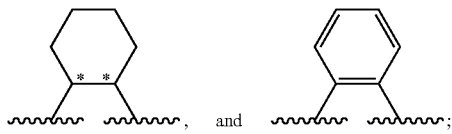 [SMILES: *C1CCCCC1* ; *c1ccccc1*]

$L^1$ is $CH_3CN$;
$L^2$ is selected from the group consisting of CO, $CH_3CN$ and CNtBu; and
m is +2.

9. A hexa-coordinate iron (II) complex of the structure of formula (I):

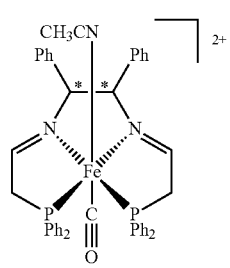

10. The hexa-coordinate iron (II) complex of claim 9, wherein the chiral carbon atoms denoted by asterisks: both have an R configuration, or both have an S configuration.

11. A process for the preparation of a hexa-coordinate iron (II) complex of claim 1, the process comprising reacting a phosphinaldehyde precursor of formula (V):

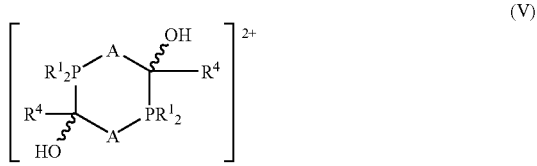

(V)

wherein
each $R^1$ is independently selected from the group consisting of aryl, heteroaryl, $C_1$-$C_8$ alkyl, $C_2$-$C_8$ alkenyl, $C_1$-$C_8$ alkoxy, aryloxy, and cycloalkyl, all of which may be optionally substituted; two geminal $R^1$ groups may combine to form a $C_2$-$C_4$ linear alkyl diradical or $C_3$-$C_8$ branched alkyl diradical, each of which may be optionally substituted, to form a ring together with the phosphorus atom to which they are attached; or two $R^1$ groups, each of which is located on a different phosphorus atom, may combine to form a linker M, wherein M is selected from the group consisting of $C_2$-$C_4$ linear alkyl diradical and $C_3$-$C_8$ branched alkyl diradical, each of which may be optionally substituted, or M may be a diradical ligand with a wide bite angle;
A is

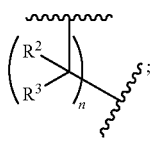

wherein each $R^2$ and $R^3$ are independently selected from the group consisting of H, substituted or unsubstituted $C_1$-$C_8$ alkyl, substituted or unsubstituted $C_2$-$C_8$ alkenyl, substituted or unsubstituted aryl, and substituted or unsubstituted cycloalkyl, and each n is an integer independently selected from 1, 2, and 3;
each $R^4$ is independently selected from the group consisting of H, substituted or unsubstituted $C_1$-$C_8$ alkyl, substituted or unsubstituted $C_2$-$C_8$ alkenyl, substituted or unsubstituted aryl, and substituted or unsubstituted cycloalkyl;
with a diamine of formula (VI):

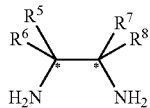

(VI)

wherein
each $R^5$, $R^6$, $R^7$ and $R^8$ is independently selected from the group consisting of H, substituted or unsubstituted $C_1$-$C_8$ alkyl, substituted or unsubstituted $C_2$-$C_8$ alkenyl, substituted or unsubstituted aryl, and substituted or unsubstituted cycloalkyl; $R^5$ and $R^6$, together with the carbon atom to which they are attached, may combine to form a substituted or unsubstituted cycloalkyl ring of size from 5-8 carbons; $R^7$ and $R^8$, together with the carbon atom to which they are attached, may combine to form a substituted or unsubstituted cycloalkyl ring of size from 5-8 carbons; or $R^5$, $R^6$, $R^7$ and $R^8$, together with the carbon atoms to which they are attached, may combine to form a group selected from

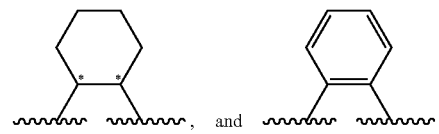 [SMILES: *C1CCCCC1* ; *c1ccccc1*]

, and each of which may be optionally substituted with one or more substituents selected from the group consisting of $C_1$-$C_8$ alkyl, $C_1$-$C_8$ alkoxy, and halogen atoms;
in the presence of:
an iron (II) salt;
a ligand selected from the group consisting of $CH_3CN$; pyridine and derivatives thereof; and imidazole and derivatives thereof; and
a strong base;
to form the compound of formula (I)

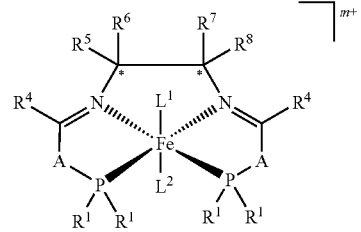

(I)

wherein A, $R^1$-$R^8$, and n are as defined above,
m is +2,
$L^1$ and $L^2$ are both $CH_3CN$; pyridine or a derivative thereof; or imidazole or a derivative thereof;
and adding at least one counter ion to counterbalance the charge of the compound of formula (I);
with the proviso that when $R^1$ is $C_1$-$C_8$ alkyl, $L^1$ is not $CH_3CN$, and $L^2$ is $CH_3CN$.

12. The process of claim 11 wherein the compound of formula (I) is further reacted with CO; hydride; halide ion; NCR, CNR or $^-$OR, wherein R is independently selected from the group consisting of aryl, heteroaryl, $C_1$-$C_8$ alkyl, $C_2$-$C_8$ alkenyl and cycloalkyl, all of which may be optionally substituted; $R^aR^bR^cN$ wherein $R^a$, $R^b$, and $R^c$ are independently selected from the group consisting of H and $C_1$-$C_2$ alkyl; or $R^c(CO)R^d$ wherein $R^c$ and $R^d$ are independently selected from the group consisting of $C_1$-$C_8$ alkyl, aryl, and heteroaryl, to produce a compound of formula (VIIIa):

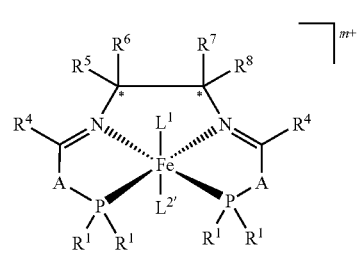

(VIIIa)

wherein A, $R^1$-$R^8$, and n are as defined for formula (I),
$L_1$ is $CH_3CN$; pyridine or a derivative thereof; or imidazole or a derivative thereof; and L$^{2'}$ is selected from the group consisting of CO; hydride; halide ion; NCR, NCR or $^-$OR, wherein R is independently selected from the group consisting of aryl, heteroaryl, C$_1$-C$_8$ alkyl, C$_2$-C$_8$ alkenyl and cycloalkyl, all of which may be optionally substituted; R$^a$R$^b$R$^c$N wherein R$^a$, R$^b$, and R$^c$ are independently selected from the group consisting of H and C$_1$-C$_2$ alkyl; or R$^c$(CO)R$^d$ wherein R$^c$ and R$^d$ are independently selected from the group consisting of C$_1$-C$_8$ alkyl, aryl, and heteroaryl, and m is +1 or +2.

13. The process of claim 12 wherein the phosphinaldehyde precursor is:

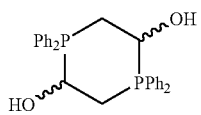

the diamine is:

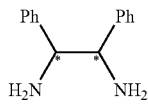

and the product is a compound of formula (I) having the structure:

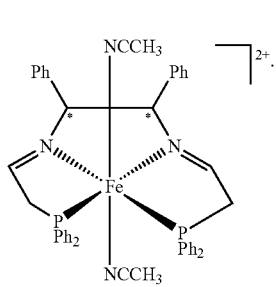

(III)

14. The process of claim 13, wherein the chiral carbon atoms denoted by asterisks:
both have an R configuration, or
both have an S configuration.

15. A process for the preparation of a hexa-coordinate iron (II) complex of claim 1, the process comprising reacting a phosphinaldehyde precursor of formula (V):

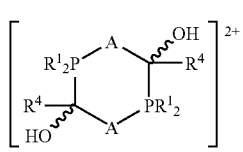

(V)

wherein
each R$^1$ is independently selected from the group consisting of aryl, heteroaryl, C$_1$-C$_8$ alkyl, C$_2$-C$_8$ alkenyl, C$_1$-C$_8$ alkoxy, aryloxy, and cycloalkyl, all of which may be optionally substituted; two geminal R$^1$ groups may combine to form a C$_2$-C$_4$ linear alkyl diradical or C$_3$-C$_8$ branched alkyl diradical, each of which may be optionally substituted, to form a ring together with the phosphorus atom to which they are attached; or two R$^1$ groups, each of which is located on a different phosphorus atom, may combine to form a linker M, wherein M is selected from the group consisting of C$_2$-C$_4$ linear alkyl diradical and C$_3$-C$_8$ branched alkyl diradical, each of which may be optionally substituted, or M may be a diradical ligand with a wide bite angle;

A is

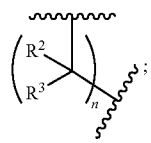

wherein each R$^2$ and R$^3$ are independently selected from the group consisting of H, substituted or unsubstituted C$_1$-C$_8$ alkyl, substituted or unsubstituted C$_2$-C$_8$ alkenyl, substituted or unsubstituted aryl, and substituted or unsubstituted cycloalkyl, and each n is an integer independently selected from 1, 2, and 3;

each R$^4$ is independently selected from the group consisting of H, substituted or unsubstituted C$_1$-C$_8$ alkyl, substituted or unsubstituted C$_2$-C$_8$ alkenyl, substituted or unsubstituted aryl, and substituted or unsubstituted cycloalkyl;

with a diamine of formula (VI):

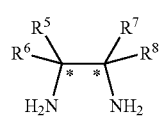

(VI)

wherein
each R$^5$, R$^6$, R$^7$ and R$^8$ is independently selected from the group consisting of H, substituted or unsubstituted C$_1$-C$_8$ alkyl, substituted or unsubstituted C$_2$-C$_8$ alkenyl, substituted or unsubstituted aryl, and substituted or unsubstituted cycloalkyl; R$^5$ and R$^6$, together with the carbon atom to which they are attached, may combine to form a substituted or unsubstituted cycloalkyl ring of size from 5-8 carbons; R$^7$ and R$^8$, together with the carbon atom to which they are attached, may combine to form a substituted or unsubstituted cycloalkyl ring of size from 5-8 carbons; or R$^5$, R$^6$, R$^7$ and R$^8$, together with the carbon atoms to which they are attached, may combine to form a group selected from

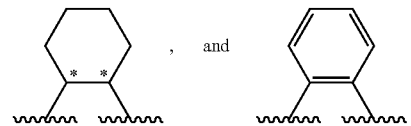 [SMILES: *C1CCCCC1* ; *c1ccccc1*]

each of which may be optionally substituted with one or more substituents selected from the group consisting of C$_1$-C$_8$ alkyl, C$_1$-C$_8$ alkoxy, and halogen atoms;
in the presence of:
an iron (II) salt;
a ligand selected from the group consisting of CH$_3$CN; pyridine and derivatives thereof; and imidazole and derivatives thereof; and a strong base;

and further reacting the reaction product of the foregoing steps with CO to produce a compound of formula (VIIIa):

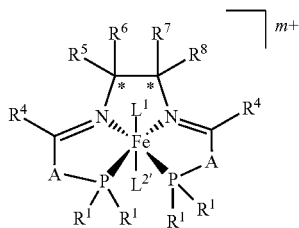

wherein A, $R^1$-$R^8$, and n are as defined above, $L_1$ is CO, $L^{2'}$ is Br, and m is +1;

and adding a counter ion to counterbalance the charge of the compound of formula (VIIIa).

16. A process for the preparation of a hexa-coordinate iron (II) complex of claim 1, the process comprising reacting a phosphinaldehyde precursor of formula (V):

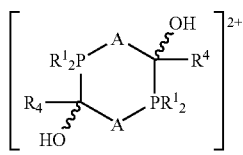

wherein
each $R^1$ $C_1$-$C_8$ alkyl;
A is

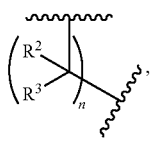

wherein each $R^2$ and $R^3$ are independently selected from the group consisting of H, substituted or unsubstituted $C_1$-$C_8$ alkyl, substituted or unsubstituted $C_2$-$C_8$ alkenyl, substituted or unsubstituted aryl, and substituted or unsubstituted cycloalkyl, and each n is an integer independently selected from 1, 2, and 3;

each $R^4$ is independently selected from the group consisting of H, substituted or unsubstituted $C_1$-$C_8$ alkyl, substituted or unsubstituted $C_2$-$C_8$ alkenyl, substituted or unsubstituted aryl, and substituted or unsubstituted cycloalkyl;

with a diamine of formula (VI):

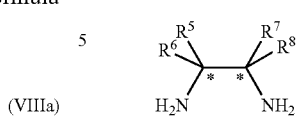

wherein
each $R^5$, $R^6$, $R^7$ and $R^8$ is independently selected from the group consisting of H, substituted or unsubstituted $C_1$-$C_8$ alkyl, substituted or unsubstituted $C_2$-$C_8$ alkenyl, substituted or unsubstituted aryl, and substituted or unsubstituted cycloalkyl; $R^5$ and $R^6$, together with the carbon atom to which they are attached, may combine to form a substituted or unsubstituted cycloalkyl ring of size from 5-8 carbons; $R^7$ and $R^8$, together with the carbon atom to which they are attached, may combine to form a substituted or unsubstituted cycloalkyl ring of size from 5-8 carbons; or $R^5$, $R^6$, $R^7$ and $R^8$, together with the carbon atoms to which they are attached, may combine to form a group selected from

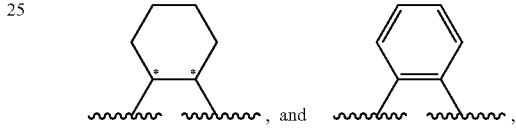

each of which may be optionally substituted with one or more substituents selected from the group consisting of $C_1$-$C_8$ alkyl, $C_1$-$C_8$ alkoxy, and halogen atoms;
  in the presence of:
    an iron (II) salt;
    a ligand selected from the group consisting of $CH_3CN$; pyridine and derivatives thereof; and imidazole and derivatives thereof; and
    a strong base;
    to form the compound of formula (I)

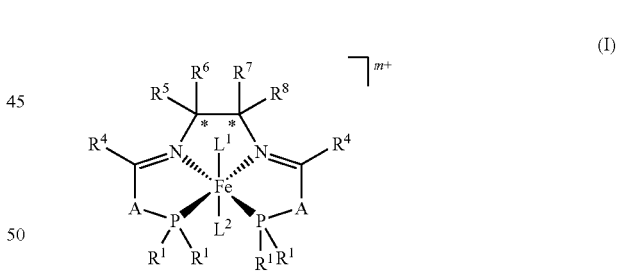

wherein A, $R^1$-$R^8$, and n are as defined above,
m is +2,
$L^1$ is Br or $CH_3CN$, and $L^2$ is CO or $CH_3CN$; and
when $R^1$ is $C_1$ to $C_8$ alkyl, $L^1$ and $L^2$ may both be $CH_3CN$;
and adding at least one counter ion to counterbalance the charge of the compound of formula (I).

* * * * *